(12) United States Patent
Law et al.

(10) Patent No.: US 12,420,093 B2
(45) Date of Patent: Sep. 23, 2025

(54) WEARABLE NEUROMODULATOR DEVICES

(71) Applicant: Thync Global, Inc., Los Gatos, CA (US)

(72) Inventors: Wing Law, Cupertino, CA (US); Isy Goldwasser, Los Gatos, CA (US); Remi Demers, Saint-Nicolas (CA); Sumon K. Pal, Boston, MA (US)

(73) Assignee: Thync Global, Inc., Los Gatos, CA (US)

( * ) Notice: Subject to any disclaimer, the term of this patent is extended or adjusted under 35 U.S.C. 154(b) by 0 days.

(21) Appl. No.: 18/497,198

(22) Filed: Oct. 30, 2023

(65) Prior Publication Data
US 2024/0058606 A1     Feb. 22, 2024

Related U.S. Application Data

(63) Continuation of application No. 17/696,788, filed on Mar. 16, 2022, now Pat. No. 11,833,352, which is a
(Continued)

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01); *A61N 1/0496* (2013.01)

(58) Field of Classification Search
CPC .... A61N 1/0404; A61N 1/042; A61N 1/0444; A61N 1/0452; A61N 1/0456; A61N 1/0492; A61N 1/0496; A61N 1/36034
See application file for complete search history.

(56) References Cited

U.S. PATENT DOCUMENTS 3,255,753 A   6/1966 Wing
3,388,699 A   6/1968 Webb et al.
(Continued)

FOREIGN PATENT DOCUMENTS

CN   1204268 A   1/1999
CN   1607970 A   4/2005
(Continued)

OTHER PUBLICATIONS

Aston-Jones et al.; An integrative theory of locus coeruleus-norepinephrine function: adaptive gain and optimal performance; Annu. Rev. Neurosci.; 28: pp. 403-450; Jul. 21, 2005.
(Continued)

*Primary Examiner* — Tammie K Marlen
(74) *Attorney, Agent, or Firm* — Shay Glenn LLP

(57) ABSTRACT

Wearable neuromodulator devices. The devices may include a first electrode and a second electrode on a flexible substrate. A first hydrogel layer may be in electrical communication with the first electrode and a second hydrogel layer may be in electrical communication with the second electrode. A third hydrogel layer may be in electrical communication with the first hydrogel layer. The first hydrogel layer may be separated from the third hydrogel layer by a removable release layer. A circuit interrupt may be removably coupled with control circuitry. The circuit interrupt may be interposed between a battery and the control circuitry so that removing the circuit interrupt powers the control circuitry. The control circuitry may be configured to deliver a first predefined waveform between the first and second electrodes after the circuit interrupt is removed, and a second predefined waveform between the first and second electrodes after the release layer is removed.

16 Claims, 48 Drawing Sheets

Related U.S. Application Data continuation of application No. 16/393,590, filed on Apr. 24, 2019, now Pat. No. 11,278,724.

(60) Provisional application No. 62/818,098, filed on Mar. 13, 2019, provisional application No. 62/662,057, filed on Apr. 24, 2018.

(56) References Cited

U.S. PATENT DOCUMENTS

| | | |
|---|---|---|
| 3,620,219 A | 11/1971 | Barker |
| 3,648,708 A | 3/1972 | Haeri |
| 3,762,396 A | 10/1973 | Ballentine et al. |
| 4,418,687 A | 12/1983 | Matsumoto et al. |
| 4,431,000 A | 2/1984 | Butler et al. |
| 4,541,432 A | 9/1985 | Molina-Negro et al. |
| 4,646,744 A | 3/1987 | Capel |
| 4,664,117 A | 5/1987 | Beck |
| 4,865,048 A | 9/1989 | Eckerson |
| 5,144,952 A | 9/1992 | Frachet et al. |
| 5,183,041 A | 2/1993 | Toriu et al. |
| 5,222,494 A | 6/1993 | Baker |
| 5,335,657 A | 8/1994 | Terry et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,738,647 A | 4/1998 | Bernhard et al. |
| 5,792,067 A | 8/1998 | Karell |
| 6,066,163 A | 5/2000 | John |
| 6,280,454 B1 | 8/2001 | Wang |
| 6,324,432 B1 | 11/2001 | Rigaux et al. |
| 6,445,955 B1 | 9/2002 | Michelson et al. |
| 6,463,328 B1 | 10/2002 | John |
| 6,516,227 B1 | 2/2003 | Meadows et al. |
| 6,526,318 B1 | 2/2003 | Ansarinia |
| 6,567,702 B1 | 5/2003 | Nekhendzy et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,263,501 B2 | 8/2007 | Tirinato et al. |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,801,600 B1 | 9/2010 | Carbunaru et al. |
| 7,891,615 B2 | 2/2011 | Bevirt |
| 7,949,403 B2 | 5/2011 | Palermo et al. |
| 8,029,431 B2 | 10/2011 | Tonont |
| 8,034,294 B1 | 10/2011 | Goldberg |
| 8,086,318 B2 | 12/2011 | Strother et al. |
| 8,097,926 B2 | 1/2012 | De Graff et al. |
| 8,116,875 B2 | 2/2012 | Osypka et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 | 6/2012 | Egloff et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,346,337 B2 | 1/2013 | Heller et al. |
| 8,380,315 B2 | 2/2013 | DeGiorgio et al. |
| 8,428,738 B2 | 4/2013 | Valencia |
| 8,463,383 B2 | 6/2013 | Sakai et al. |
| 8,494,625 B2 | 7/2013 | Hargrove |
| 8,494,627 B2 | 7/2013 | Bikson et al. |
| 8,506,469 B2 | 8/2013 | Dietrich et al. |
| 8,532,758 B2 | 9/2013 | Silverstone |
| 8,560,075 B2 | 10/2013 | Covalin |
| 8,571,651 B2 | 10/2013 | Ben-Ezra et al. |
| 8,583,238 B1 | 11/2013 | Heldman et al. |
| 8,583,256 B2 | 11/2013 | Tracey et al. |
| 8,612,005 B2 | 12/2013 | Rezai et al. |
| 8,639,343 B2 | 1/2014 | De Vos |
| 8,660,644 B2 | 2/2014 | Jaax et al. |
| 8,688,239 B2 | 4/2014 | Hartlep et al. |
| 8,843,210 B2 | 9/2014 | Simon et al. |
| 8,874,219 B2 | 10/2014 | Trier et al. |
| 8,903,494 B2 | 12/2014 | Goldwasser et al. |
| 8,983,621 B2 | 3/2015 | Hou et al. |
| 9,002,458 B2 | 4/2015 | Pal et al. |
| 9,014,811 B2 | 4/2015 | Pal et al. |
| 9,067,054 B2 | 6/2015 | Simon et al. |
| 9,168,374 B2 | 10/2015 | Su |
| 9,205,258 B2 | 12/2015 | Simon et al. |
| 9,233,244 B2 | 1/2016 | Pal et al. |
| 9,248,292 B2 | 2/2016 | Trier et al. |
| 9,333,334 B2 | 5/2016 | Jeffery et al. |
| 9,364,674 B2 | 6/2016 | Cook et al. |
| 9,393,401 B2 | 7/2016 | Goldwasser et al. |
| 9,393,430 B2 | 7/2016 | Demers et al. |
| 9,399,126 B2 | 7/2016 | Pal et al. |
| 9,415,219 B2 | 8/2016 | Simon et al. |
| 9,440,070 B2 | 9/2016 | Goldwasser et al. |
| 9,446,242 B2 | 9/2016 | Griffith |
| 9,474,891 B2 | 10/2016 | Demers et al. |
| 9,474,905 B2 | 10/2016 | Doan et al. |
| 9,517,351 B2 | 12/2016 | Charlesworth et al. |
| 9,655,772 B2 | 5/2017 | Smith et al. |
| 9,656,076 B2 | 5/2017 | Trier et al. |
| 9,700,725 B2 | 7/2017 | Zhu |
| 9,731,116 B2 | 8/2017 | Chen |
| 9,744,347 B2 | 8/2017 | Chen et al. |
| 9,764,133 B2 | 9/2017 | Thomas et al. |
| 9,782,587 B2 | 10/2017 | Trier et al. |
| 9,956,405 B2 | 5/2018 | Goldwasser et al. |
| 9,968,780 B2 | 5/2018 | Pal et al. |
| 10,258,788 B2 | 4/2019 | Jeffery |
| 10,293,161 B2 | 5/2019 | Charlesworth et al. |
| 10,426,945 B2 | 10/2019 | Tyler et al. |
| 10,485,972 B2 | 11/2019 | Pal et al. |
| 10,537,703 B2 | 1/2020 | Tyler et al. |
| 10,646,708 B2 | 5/2020 | Goldwasser et al. |
| 10,814,131 B2 | 10/2020 | Goldwasser et al. |
| 11,033,731 B2 | 6/2021 | Jeffery et al. |
| 11,235,148 B2 | 2/2022 | Charlesworth et al. |
| 11,278,724 B2 | 3/2022 | Law et al. |
| 11,833,352 B2 | 12/2023 | Law et al. |
| 12,201,834 B2 | 1/2025 | Charlesworth et al. |
| 2001/0000187 A1 | 4/2001 | Peckham et al. |
| 2002/0116036 A1 | 8/2002 | Daignault et al. |
| 2003/0088279 A1 | 5/2003 | Rissmann et al. |
| 2003/0134545 A1 | 7/2003 | McAdams et al. |
| 2003/0171685 A1 | 9/2003 | Lesser et al. |
| 2003/0225323 A1 | 12/2003 | Kiani et al. |
| 2004/0019370 A1 | 1/2004 | Gliner et al. |
| 2004/0098065 A1 | 5/2004 | Hagglof et al. |
| 2004/0158305 A1 | 8/2004 | Axelgaard |
| 2004/0267333 A1 | 12/2004 | Kronberg |
| 2005/0165460 A1 | 7/2005 | Erfan |
| 2005/0267388 A1 | 12/2005 | Hanna |
| 2005/0283259 A1 | 12/2005 | Wolpow |
| 2006/0047215 A1 | 3/2006 | Newman et al. |
| 2006/0064139 A1 | 3/2006 | Chung et al. |
| 2006/0149119 A1 | 7/2006 | Wang |
| 2006/0190057 A1 | 8/2006 | Reese |
| 2006/0195159 A1 | 8/2006 | Bradley et al. |
| 2006/0206163 A1 | 9/2006 | Wahlstrand et al. |
| 2006/0247985 A1 | 11/2006 | Liamos et al. |
| 2007/0053466 A1 | 3/2007 | Klostermann |
| 2007/0088419 A1 | 4/2007 | Fiorina et al. |
| 2007/0097593 A1 | 5/2007 | Armstrong |
| 2007/0100275 A1 | 5/2007 | Fischer et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0015641 A1 | 1/2008 | Armstrong et al. |

(56) References Cited

U.S. PATENT DOCUMENTS

| | | |
|---|---|---|
| 2008/0045882 A1 | 2/2008 | Finsterwald |
| 2008/0071626 A1 | 3/2008 | Hill |
| 2008/0097564 A1 | 4/2008 | Lathrop |
| 2008/0132974 A1 | 6/2008 | Strother et al. |
| 2008/0207985 A1 | 8/2008 | Farone |
| 2008/0208266 A1 | 8/2008 | Lesser et al. |
| 2008/0215113 A1 | 9/2008 | Pawlowicz |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0054952 A1 | 2/2009 | Glukhovsky et al. |
| 2009/0076559 A1 | 3/2009 | Libbus et al. |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0145428 A1 | 6/2010 | Cameron et al. |
| 2010/0152817 A1 | 6/2010 | Gillbe |
| 2010/0222734 A1 | 9/2010 | Jayes et al. |
| 2010/0256436 A1 | 10/2010 | Partsch et al. |
| 2010/0318168 A1 | 12/2010 | Bignetti |
| 2011/0029045 A1 | 2/2011 | Cevette et al. |
| 2011/0034756 A1 | 2/2011 | Hacking et al. |
| 2011/0077660 A1 | 3/2011 | Janik et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0301683 A1 | 12/2011 | Axelgaard |
| 2011/0307029 A1 | 12/2011 | Hargrove |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1 | 7/2012 | Simon et al. |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0155561 A1 | 6/2013 | Chein-Feng |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2013/0333094 A1 | 12/2013 | Rogers et al. |
| 2014/0031895 A1 | 1/2014 | Rahimi et al. |
| 2014/0128939 A1 | 5/2014 | Embrey et al. |
| 2014/0128944 A1 | 5/2014 | Stern et al. |
| 2014/0163645 A1 | 6/2014 | Dinsmoor et al. |
| 2014/0182350 A1 | 7/2014 | Bhavaraju et al. |
| 2014/0186807 A1 | 7/2014 | Rastatter et al. |
| 2014/0222102 A1 | 8/2014 | Lemus et al. |
| 2014/0257449 A1 | 9/2014 | Helmer |
| 2014/0275933 A1 | 9/2014 | Meyer et al. |
| 2014/0277324 A1 | 9/2014 | DiUbaldi et al. |
| 2014/0309709 A1 | 10/2014 | Gozani et al. |
| 2014/0324138 A1 | 10/2014 | Wentz et al. |
| 2014/0336728 A1 | 11/2014 | Franke et al. |
| 2014/0371814 A1 | 12/2014 | Spizzirri et al. |
| 2015/0066104 A1 | 3/2015 | Wingeier et al. |
| 2015/0224310 A1 | 8/2015 | Sharma et al. |
| 2015/0230863 A1 | 8/2015 | Youngquist et al. |
| 2015/0257970 A1 | 9/2015 | Mucke et al. |
| 2015/0335877 A1 | 11/2015 | Jeffery et al. |
| 2015/0360038 A1 | 12/2015 | Zottola et al. |
| 2016/0008632 A1 | 1/2016 | Wetmore et al. |
| 2016/0074657 A1 | 3/2016 | Kwan et al. |
| 2016/0279435 A1 | 9/2016 | Hyde et al. |
| 2017/0076414 A1 | 3/2017 | Egnal et al. |
| 2017/0290546 A1 | 10/2017 | Antonio et al. |
| 2018/0036533 A1 | 2/2018 | Yoo et al. |
| 2020/0147340 A1 | 5/2020 | Tyler et al. |
| 2020/0155790 A9 | 5/2020 | Tyler et al. |
| 2020/0297999 A1 | 9/2020 | Pal |
| 2022/0273947 A1 | 9/2022 | Law et al. |
| 2025/0108215 A1 | 4/2025 | Charlesworth et al. |

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49061984 A | 6/1974 |
| JP | 05031197 A | 2/1993 |
| JP | 06339531 A | 12/1994 |
| JP | 10108913 A | 4/1998 |
| JP | 2001129100 A | 5/2001 |
| JP | 2001293097 A | 10/2001 |
| JP | 2002306604 A | 10/2002 |
| JP | 200310230 A | 1/2003 |
| JP | 2006192302 A | 7/2006 |
| JP | 3129187 U | 1/2007 |
| JP | 2007535372 A | 12/2007 |
| JP | 200985901 A | 4/2009 |
| JP | 2009513248 A | 4/2009 |
| JP | 2011118293 A | 6/2011 |

(56) References Cited

FOREIGN PATENT DOCUMENTS

| | | |
|---|---|---|
| JP | 2011519654 A | 7/2011 |
| JP | 2013512076 A | 4/2013 |
| WO | WO90/09810 A1 | 9/1990 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/08071 A1 | 2/2001 |
| WO | WO01/78834 A1 | 10/2001 |
| WO | WO03/018120 A1 | 3/2003 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/022215 A1 | 2/2014 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |
| WO | WO2017/201525 A1 | 11/2017 |
| WO | WO2019/138407 A1 | 7/2019 |

OTHER PUBLICATIONS

Aston-Jones et al.; Role of locus coeruleus in attention and behavioral flexibility; Biological Psychiatry; 46(9); pp. 1309-1320; Nov. 1, 1999.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Backhaus et al.; Sleep disturbances are correlated with decreased morning awakening salivary cortisol; Psychoneuroendocrinology; 29(9): pp. 1184-1191; Oct. 31, 2004.

Basta et al.; Chronic Insomnia and the Stress System; Sleep Medicine Clinics; 2(2): pp. 279-291; (Author Manuscript, 20 pages); Jun. 30, 2007.

Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.

Berridge et al.; The locus coeruleus-noradrenergic system: modulation of behavioral state and state-dependent cognitive processes; Brain Research Reviews; 42(1); pp. 33-84; Apr. 30, 2003.

Brown et al.; Control of sleep and wakefulness; Physiological reviews; 92(3); pp. 1087-1187; Jul. 1, 2012.

Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.

Buchanan et al.; Salivary alpha-amylase levels as a biomarker of experienced fear; Communicative and Integrative Biology; 3(6); pp. 525-527; Nov. 1, 2010.

Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.

Buysse et al.; The Pittsburgh Sleep Quality Index: a new instrument for psychiatric practice and research; Psychiatric Research; 28(2); pp. 193-213; May 31, 1989.

Carter et al.; Tuning arousal with optogenetic modulation of locus coeruleus neurons; Nature Neuroscience; 13(12); pp. 1526-1533; Dec. 1, 2010.

Chaieb et al.; Transcranial alternating current stimulation in the low kHz range increases motor cortex excitability; Restor Neurol Neurosci; 29(3); pp. 167-175; Mar. 2011.

Cook et al.; Trigeminal nerve stimulation in major depressive disorder: acute outcomes in an open pilot study; Epilepsy and Behavior; 28(2): pp. 221-226; Aug. 31, 2013.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

DeGiorgio et al., Trigeminal nerve stimulation for epilepsy: long-term feasibility and efficacy; Neurology; 72(10): pp. 936-938; Mar. 10, 2009.

DeDiorgio et al.; Randomized controlled trial of trigeminal nerve stimulation for drug-resistant epilepsy; Neurology; 80(9); pp. 786-791; Feb. 26, 2013.

Digitimer Ltd.; DS2 and DS3 Isolated Stimulator (product information); 2 pgs.; downloaded from http://www.digitimer.com/research/stimulators/index.htm on Feb. 10, 2014.

Elder et al.; The cortisol awakening response—applications and implications for sleep medicine; Sleep Medicine Reviews; 18(3): pp. 215-224; Jun. 30, 2014.

Electozyme; Company and Product Information; 3 pgs.; printed Feb. 11, 2014 from http://electrozyme.com/applications/.

Eschenko et al.; Noradrenergic neurons of the locus coeruleus are phase locked to cortical up-down states during sleep; Cerebral Cortex; 22(2); pp. 426-435; Feb. 1, 2012.

Feurra et al.; Frequency specific modulation of human somatosensory cortex; Front Psychol; 2(13); 6 pgs.; Feb. 2011.

Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.

Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.

GoFlow; tDCS Kit; product information; 9 pgs..; printed Feb. 10, 2014 (http://flowstateengaged.com/).

Golestanirad et al; Analysis of fractal electrodes for efficient neural stimulation; Frontiers in Neurengineering; 6(3); 10 pages; Jul. 2013.

Gracenote; Timeline-metadata-api; 3 pages; retrieved from the internet Jul. 7, 2015; (https://github.com/gracenote/timeline-metadata-api/blob/master/README.md).

Granger et al.; Salivary alpha-amylase in biobehavioral research: recent developments and applications; Annals of the New York Academy of Sciences; 1098(1); pp. 122-144; Mar. 1, 2007.

Grindhouse Wetware; Thinking Cap; product information; 1 pg.; printed Feb. 10, 2014 (http://www.grindhousewetware.com/thinkingcap.html).

Gummadavelli et al.; Neurostimulation to improve level of consciousness in patients with epilepsy. Neurosurgical Focus; 38(6); pp. E10; (manuscript version, 14 pages); Jun. 2015.

Hajos et al.; Norepinephrine but not serotonin reuptake inhibitors enhance theta and gamma activity of the septo-hippocampal system; Neuropsychopharmacology; 28(5); pp. 857-864; May 1, 2003.

(56) References Cited

OTHER PUBLICATIONS

Hass et al.; Waking with the hypothalamus. Pflugers Arch R Eur. J. Physiol.; 463(1): pp. 31-42; Jan. 1, 2012.

Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.

Hirotsu et al.; Interactions between sleep, stress, and metabolism; From physiological to pathological conditions; Sleep Science; 8(3); pp. 143-152; Nov. 2015.

Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.

Just et al.; Bold responses to trigeminal nerve stimulation; Magnetic Resonance Imaging; 28(8): pp. 1143-1151; Oct. 31, 2010.

Kanai et al.; Frequency-dependent electrical stimulation of the visual cortex; Curr. Biol.; 18(23); pp. 1839-1843; Dec. 9, 2008.

Kubota et al.; Role of the brain stem in cardiovascular changes induced by stimulation of the trigeminal nerve; Anesthesia Progress; 36(4-5); pp. 236-237; Jul. 1989.

Lee et al.; Neuromodulation of Brain States; Neuron; 76(1): pp. 209-222. Oct. 4, 2012.

Leproult et al.; Sleep loss results in an elevation of cortisol levels the next evening; Sleep; 20(10): pp. 865-870; Oct. 1997.

Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.

Lu et al.; A putative flip-flop switch for control of REM sleep; Nature; 441(7093): pp. 589-594; Jun. 1, 2006.

Magis et al.; Safety and patients' satisfaction of transcutaneous supraorbital neurostimulation (tSNS) with the Cefaly(R) device in headache treatment: a survey of 2,313 headache sufferers in the general population; The Journal of Headache and Pain, 14(1); p. 95; (manuscript version, 8 pages) Dec. 1, 2013.

McGough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.

Meltzer et al; Direct comparison of two new actigraphs and polysomnography in children and adolescents; Sleep; 35(1); pp. 159-166; Jan. 1, 2012.

Nash et al.; Differential activation of the human trigeminal nuclear complex by noxious and non-noxious orofacial stimulation; Human Brain Mapping; 30(11); pp. 3772-3782; Nov. 1, 2009.

Nieuwenhuis et al.; Decision making, the P3, and the locus coeruleus-norepinephrine system; Psychological Bulletin; 131(4); pp. 510-532; Jul. 2005.

Parvizi et al.; Consciousness and the brainstem; Cognition; 79(1): pp. 135-160; Apr. 30, 2001.

Paulus, W.; Transcranial electrical stimulation (tES-tDCS; tRNS, tACS) methods; Neuropsychol Rehabil.; 21(5); pp. 602-617; Oct. 2011.

Penzel et al.; Dynamics of Heart Rate and Sleep Stages in Normals and Patients with Sleep Apnea; Neuropsychopharmacology; 28(S1); pp. S48-S53; Jul. 1, 2003.

Piquet et al.; Supraorbital transcutaneous neurostimulation has sedative effects in healthy subjects; BMC Neurology; 11(1); p. 135; (manual transcript, 8 pages); Oct. 28, 2011.

Plewnia et al.; Enhancement of human cortico-motoneuronal excitability by the selective norepinephrine reuptake inhibitor reboxetine; Neuroscience Letters; 330(3); pp. 231-234; Sep. 27, 2002.

Prausnitz; The effects of electric current applied to skin: a review for transdermal drug delivery; Advanced Drug Delivery Reviews; vol. 18; pp. 395-425; Feb. 8, 1996.

Pusch et al.; Electrical stimulation of the vestibular system prevents postoperative nausea and vomiting; Acta Annesthesiol Scand.; 44(9); pp. 1145-1148; Oct. 2000.

Riemann et al.; The hyperarousal model of insomnia: A review of the concept and its evidence; Sleep Medicine Reviews; 14(1); pp. 19-31; Feb. 28, 2010.

Rill et al.; Pedunculopontine arousal system physiology-implications for insomnia; Sleep Science; 8(2); pp. 92-99; Jun. 30, 2015.

Rohleder et al.; Psychosocial stress-induced activation of salivary alpha-amylase: an indicator of sympathetic activity; Annals of the New York Academy of Sciences; 1032(1); pp. 258-263; Dec. 1, 2004.

Saiote et al.; High-frequency TRNS reduces Bold activity during visuomotor learning; PLoS one; 8(3); e59669; 8 pgs.; Mar. 2013.

Sara; The locus coeruleus and noradrenergic modulation of cognition; Nature Reviews Neuroscience; 10(3): pp. 211-223. Mar. 1, 2009.

Schmidt et al.; Adrenaline rush: the role of adrenergic receptors in stimulant-induced behaviors; Molecular Pharmacology; 85(4): pp. 640-650; Apr. 1, 2014.

Schutter et al.; Brain oscillations and frequency-dependent modulation of cortical excitability; Brain Stimulation; 4(2); pp. 97-103; Apr. 2011.

Seugnet et al.; Identification of a biomarker for sleep drive in flies and humans; Proceedings of the National Academy of Sciences; 103(52); pp. 19913-19918; Dec. 26, 2006.

Shiozawa et al.; Transcutaneous vagus and trigeminal nerve stimulation for neuropsychiatric disorders: a systematic review, Arquivos de neuro-psiquiatria; 72(7): pp. 542-547; Jul. 2014.

Siegel; Brain mechanisms that control sleep and waking. Naturwissenschaften; 91(8); pp. 355-365; Aug. 1, 2004.

Somana et al.; Cerebellar afferents from the trigeminal sensory nuclei in the cat. Brain Res.; 38(1); pp. 57-64; Jan. 1980.

STD Pharmaceutical Products; Idrostar intophoresis machine (product and use information); 9 pgs.; Dec. 2011 (printed Feb. 11, 2014 from http://www.iontophoresis.info/instructions/).

Strassman et al; Response of brainstem trigeminal neurons to electrical stimulation of the dura; Brain Research; 379(2): pp. 242-250; Aug. 6, 1986.

Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.

Terney et al.; Increasing human brain excitability by transcranial high-frequency random noise stimulation; The Journal of Neuroscience; 28(52); pp. 14127-14155; Dec. 2008.

Thoma et al.; Acute stress responses in salivary alpha-amylase predict increases of plasma norepinephrine; Biological Psychology; 91(3): pp. 342-348; Dec. 31, 2012.

Tremblay et al.; Uncertain Outcome of Prefrontal tDCS; Brain Stimulation; 7(6): pp. 773-783; Dec. 31, 2014.

Trevizol et al.; Trigeminal Nerve Stimulation (TNS) for Generalized Anxiety Disorder: A Case Study; Brain Stimulation; 8(3): pp. 659-660; Jan. 1, 2015.

Trevizol et al.; Trigeminal Nerve Stimulation (TNS) for Post-traumatic Stress Disorder: A Case Study; Brain Stimulation; 8(3): pp. 676-678; Jan. 1, 2015.

Turi et al.; Both the cutaneous sensation and phosphene perception are modulated in a frequency-specific manner during transcranial alternating current stimulation; Restor. Neurol, Neurosci.; 31(3); pp. 275-285; Jan. 2013.

Tyler et al.; Transdermal neuromodulation of noradrenergic activity suppresses psychophysiological and biochemical stress responses in humans; Scientific Reports; 5; (manual transcript, 22 pages); Feb. 8, 2015.

Tyler et al.; U.S. Appl. No. 61/550,334 entitled "Improvement Of Direct Communication," filed Oct. 21, 2011.

Tyler et al.; U.S. Appl. No. 61/663,409 entitled "Device And Methods For Noninvasive Neuromodulation Using Targeted Transcranial Electrical Stimulation," filed Jun. 22, 2012.

Tyler et al.; U.S. Appl. No. 62/166,674 entitled "Systems And Methods For Suppression Of Stress Responses By Transdermal Electrical Neuromodulation," filed May 26, 2015.

(56) References Cited

OTHER PUBLICATIONS

Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Voisin et al.; Nociceptive stimulation activates locus coeruleus neurones projecting to the somatosensory thalamus in the rat; The Journal of Physiology; 566( 3), pp. 929-937; Aug. 1, 2005.
Voss et al.; Induction of self awareness in dreams through frontal low current stimulation of gamma activity; Nature Neuroscience; 17(6); pp. 810-812; Jun. 1, 2014.
Watson et al.; Development and validation of brief measures of positive and negative affect: the PANAS scales; Jouranl of Personality and Social Psychology; 54(6); pp. 1063-1070; Jun. 1988.
Weiss et al; Validity of Activity-Based Devices to Estimate Sleep; Journal of Clinical Sleep Medicine : 6(4); pp. 336-342; Aug. 2010.

| GEL THICKNESS | HIGH | DIMINISHED EFFECT DUE TO LOWER ELECTRIC FIELD | OPTIMAL EFFECT |
|---|---|---|---|
| | MEDIUM | OPTIMAL BALANCE OF COMFORT AND EFFECT | LESS THAN OPTIMAL |
| | LOW | DISCOMFORT DUE TO ACTIVATION OF SURFACE NERVE | DISCOMFORT DUE TO ACTIVATION OF SURFACE NERVE |
| | | SHORT | LONG |
| | | NERVE'S DISTANCE FROM SURFACE | |
FIG. 3
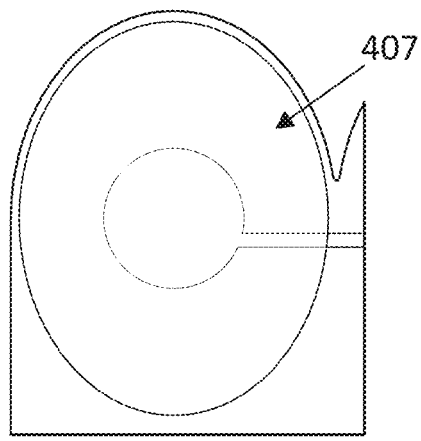
FIG. 4A
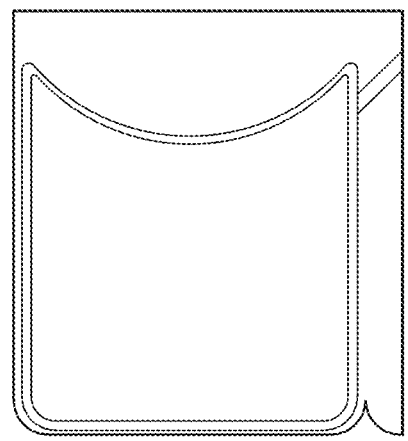
FIG. 4B

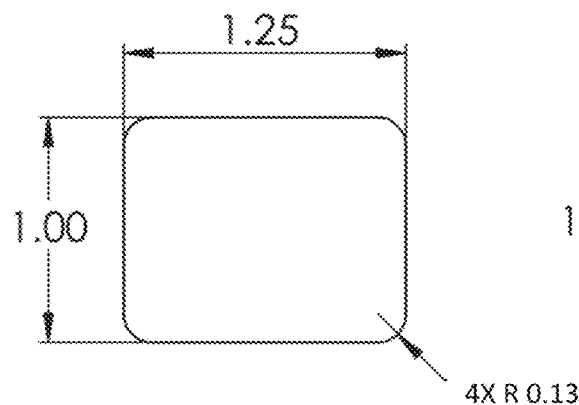
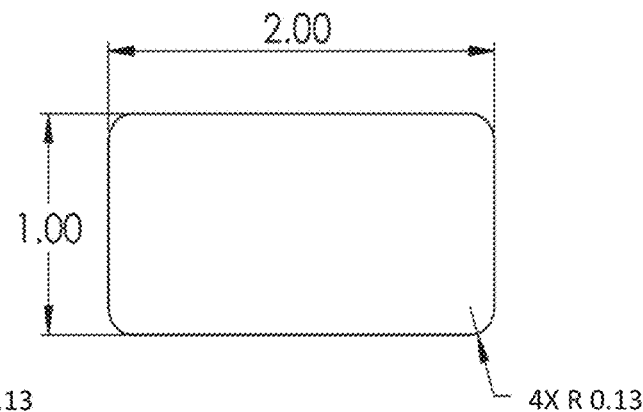
FIG. 5A              FIG. 5B
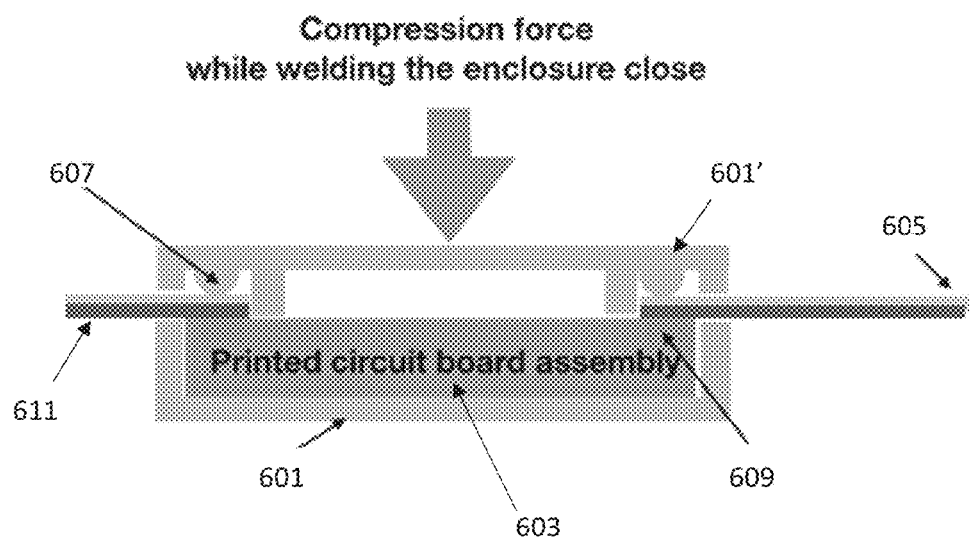
FIG. 6A

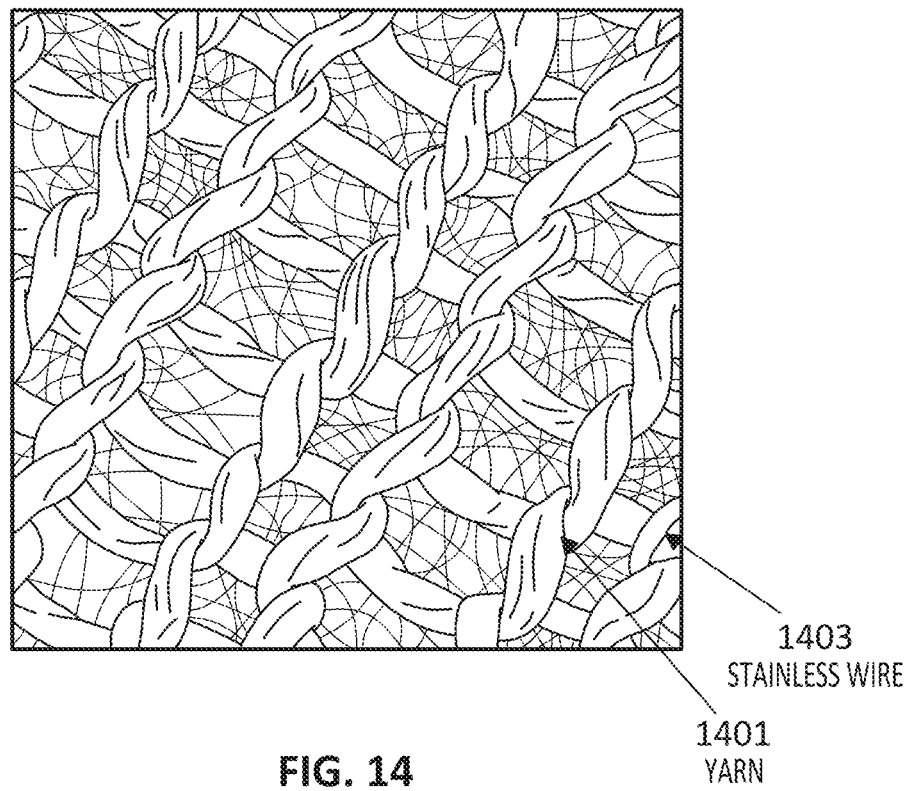
FIG. 14
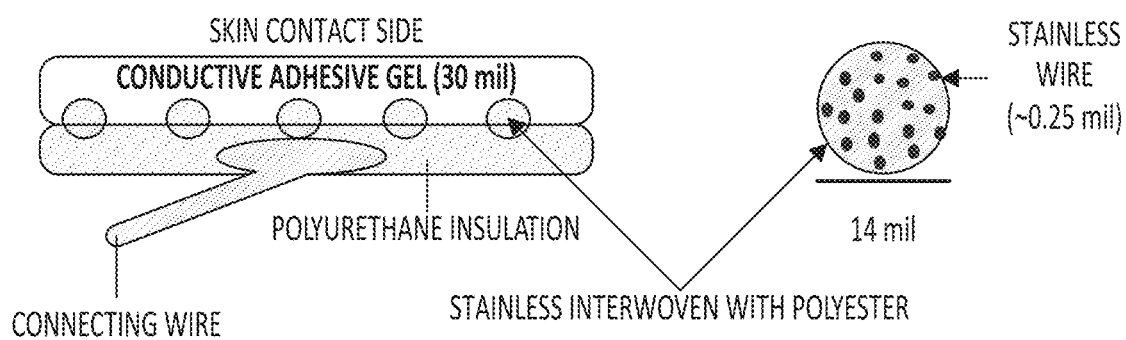
FIG. 15A  FIG. 15B

| INFORMATION | UNITY SIZE | UNIT | DATA (BYTES) | SPAWN (RAW) | MAX VALUE IN PHYSICAL UNIT | UNIT | COMMENT |
|---|---|---|---|---|---|---|---|
| BASE WAVEFORM | | | | | | | |
| PULSE A LENGTH | 5 | µS | 1 | 255 | 1275 | µS | LIMITED BY POWER DISSIPATION TO LESS |
| GAP A LENGTH | 1 | µS | 2 | 65535 | 65535 | µS | |
| PULSE B LENGTH | 5 | µS | 1 | 255 | 1275 | µS | LIMITED BY POWER DISSIPATION TO LESS |
| GAP B LENGTH | 1 | µS | 2 | 65535 | 65535 | µS | |
| TRAPEZOID MODULATION | | | | | | | |
| MIN AMPLITUDE A | 100 | µA | 1 | 255 | 25500 | µA | |
| MIN AMPLITUDE B | 100 | µA | 1 | 255 | 25500 | µA | |
| MIN AMPLITUDE DURATION | 1 | MS | 2 | 65535 | 65535 | MS | |
| RAMPING UP DURATION | 1 | MS | 2 | 65535 | 65535 | MS | |
| MAX AMPLITUDE A | 100 | µA | 1 | 255 | 25500 | µA | |
| MAX AMPLITUDE B | 100 | µA | 1 | 255 | 25500 | µA | |
| MAX AMPLITUDE DURATION | 1 | MS | 2 | 65535 | 65535 | MS | |
| RAMPING DOWN DURATION | 1 | MS | 2 | 65535 | 65535 | MS | |
| DURATION NB MODULATION CYCLES | 1 | CYCLE | 1 | 255 | 255 | CYCLE | |
| TOTAL | | | 19 | | | | |

EXAMPLE: WITH 1KB IT IS POSSIBLE TO STORE 53 DIFFERENT TRAPEZOID MODULATED WAVEFORM.

IT IS POSSIBLE TO SPLIT THE DATASET IN GROUPS AND REUSE MANY TIMES DIFFERENT COMBINATIONS OF THOSE GROUPS, WHICH WOULD INCREASE EVEN MORE THE COMPACTNESS OF THE INFORMATION.

IT IS POSSIBLE TO MODIFY THE CHOICE OF UNITS OF THIS TABLE TO TARGET DIFFERENT RANGES. BUT THE PULSE 5µS BASE UNIT CANNOT BE CHANGED.

FIG. 30A

| Waveform | Q (μcoulombs per phase) | F (Hz) | C (mA) | pDur (s) | PDC (%) |
|---|---|---|---|---|---|
| Core Psoriasis | 1.1 | 1560 | 12 | 23% | 60% |
| Transition Psoriasis | 0.7 | 580 | 7 | 20% | 30% |
| Sham Psoriasis | 0.1 | 3000 | 20 | 15% | 5% |
| Deep Relax Core | 0.8 | 3204 | 20 | 17% | 80% |
| Deep Relax light | 0.6 | 8162 | 20 | 33% | 80% |
| Deep Relax All Trills | 0.6 | 14060 | 20 | 46% | 92% |
| TENS but not biphasic | 0.1 | 3,570 | 20 | 2% | 100% |
| Base 450 Hz | 1.1 | 450 | 12 | 4% | 100% |
| Base 750 Hz | 1.1 | 750 | 5 | 17% | 100% |
| Base 330 Hz | 1.1 | 330 | 12 | 3% | 100% |
| Base 225 Hz | 1.1 | 225 | 12 | 2% | 100% |
| Base 105 Hz | 1.1 | 105 | 12 | 1% | 100% |
| Concept 1 balance | 1.1 | 450 | 3 | 16% | 100% |
| Base 1500 Hz | 1.1 | 1500 | 15 | 11% | 100% |

Table 3: examples of waveforms

FIG. 30B

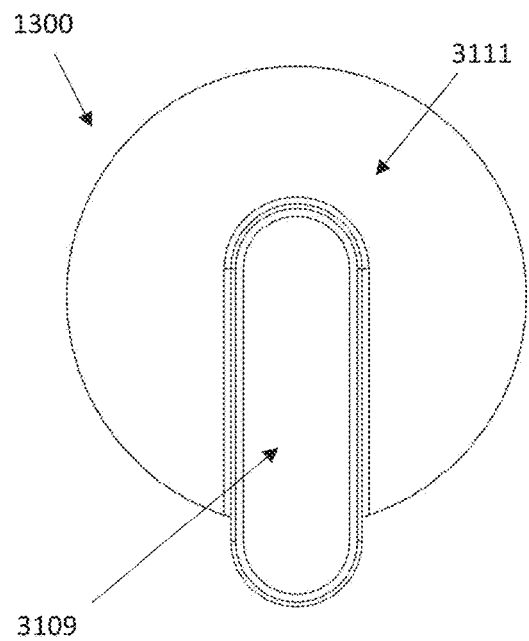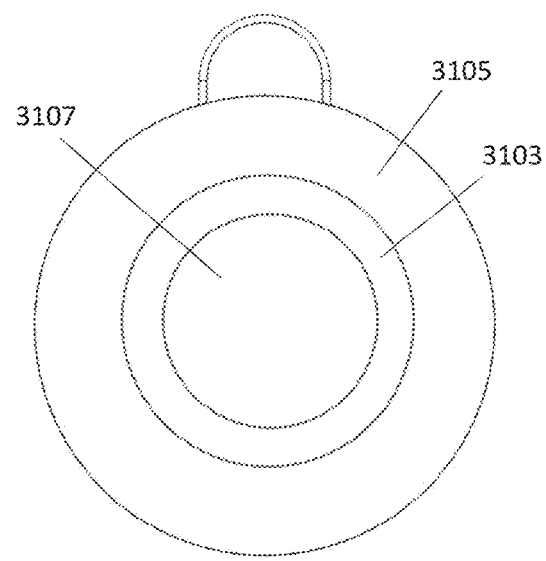
FIG. 31A  FIG. 31B
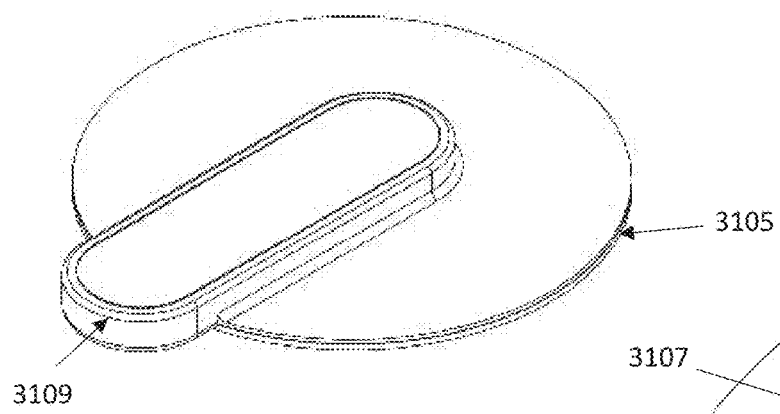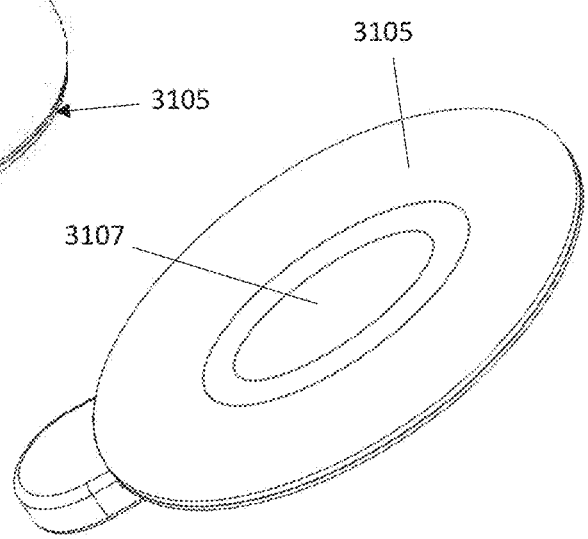
FIG. 31C  FIG. 31D

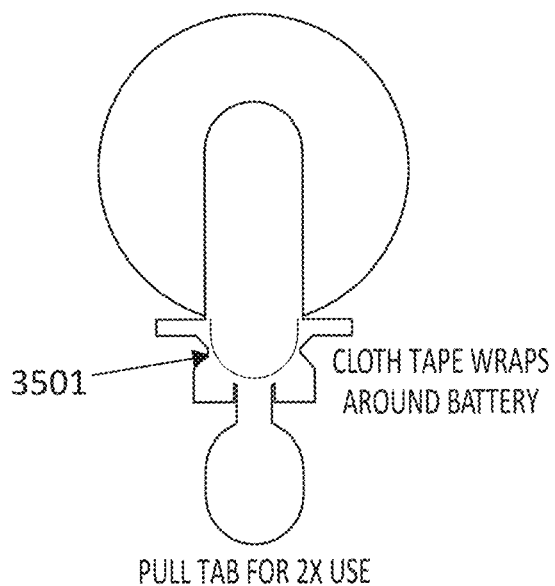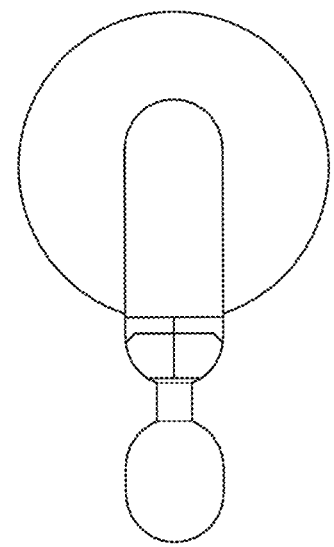
FIG. 35A  FIG. 35B
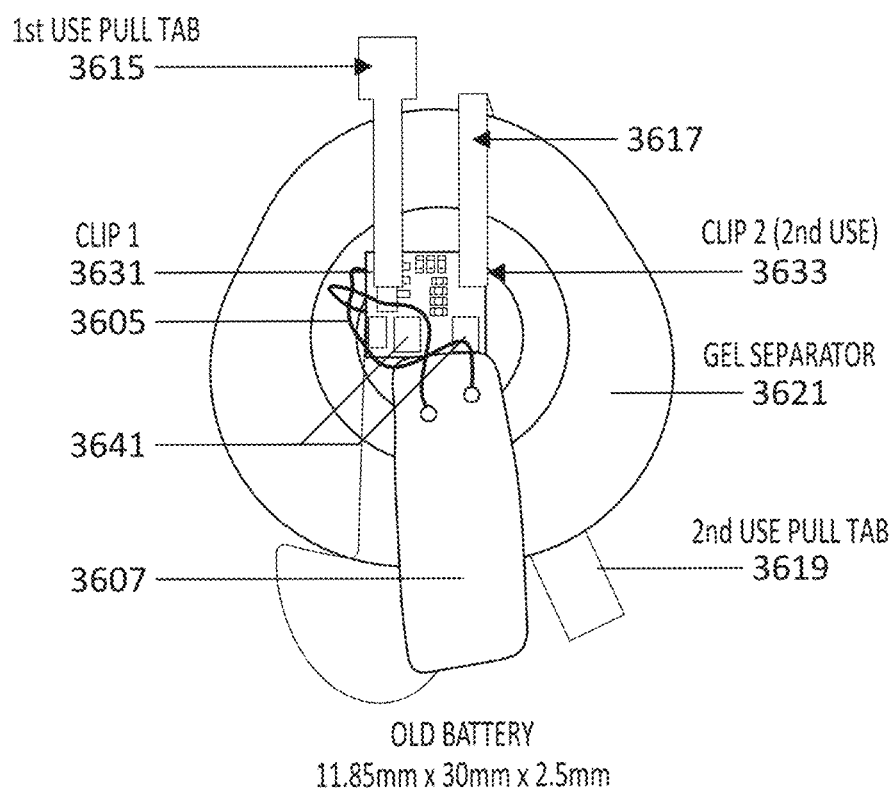
FIG. 36

9. PULL SEPARATOR FOR 2nd USE
PEEL MOTION

GEL FOR 1st USE

SEPARATOR

GEL FOR 2nd USE

4303

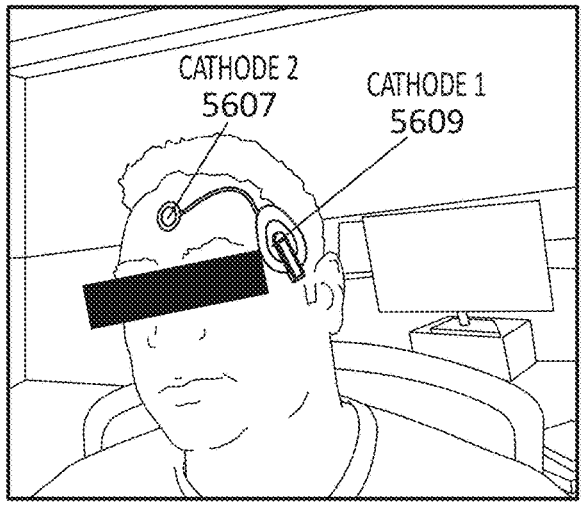
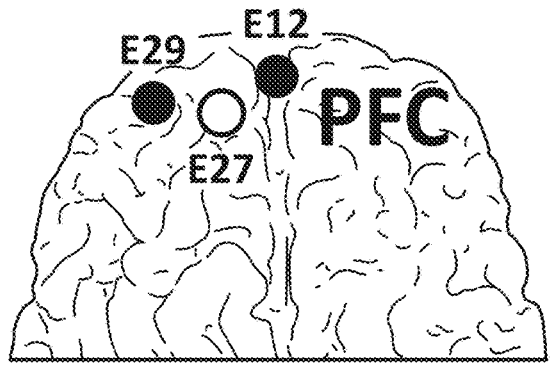
FIG. 57  FIG. 58
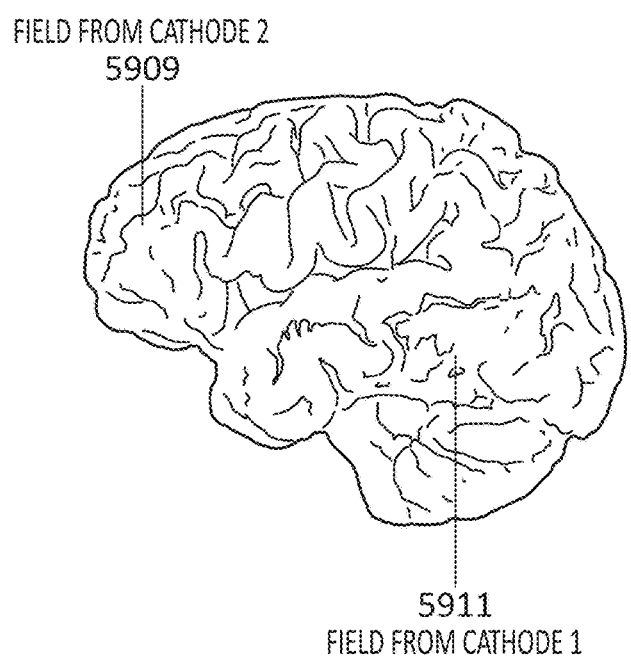
FIG. 59

WEARABLE NEUROMODULATOR DEVICES

CROSS REFERENCE TO RELATED APPLICATIONS

This patent application is a continuation of U.S. patent application Ser. No. 17/696,788, titled "STREAMLINED AND PRE-SET NEUROMODULATORS," filed Mar. 16, 2022, now U.S. Patent Application Publication No. 2022/0203092, which is a continuation of U.S. patent application Ser. No. 16/393,590, titled "STREAMLINED AND PRE-SET NEUROMODULATORS," filed Apr. 24, 2019, now U.S. Pat. No. 11,278,724, which claims priority to U.S. Provisional Patent Application No. 62/662,057, titled "SINGLE-USE NEUROSTIMULATORS," filed on Apr. 24, 2018, and U.S. Provisional Patent Application No. 62/818,098, titled "SINGLE-USE NEUROSTIMULATORS," filed on Mar. 13, 2019. Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are non-invasive neuromodulation apparatuses, including devices and systems, and methods of their use.

BACKGROUND

Noninvasive neuromodulation can effect nerves and neuronal activity (including modulating cognitive states, perception, and motor output) and have many other therapeutic effects, without requiring an invasive procedure. Transdermal electric stimulation (hereinafter "TES") using skin (e.g., scalp) electrodes has been used to affect brain function and nervous system function in humans and includes transcranial alternating current stimulation (hereinafter "tACS"), transcranial direct current stimulation (hereinafter "tDCS"), cranial electrotherapy stimulation (hereinafter "CES"), transcranial random noise stimulation (hereinafter "tRNS"), trigeminal nerve stimulation (hereinafter "TNS"), and vagal nerve stimulation ("VNS"), amongst other forms known to those skilled in the art.

TES has been used therapeutically in various clinical applications, including treatment of pain, depression, epilepsy, ADHD, and tinnitus. This neuromodulation has been demonstrated to lower physiological stress and anxiety, improve sleep, and has potential as a therapy for specific auto-immune disorders such as psoriasis. It has the potential to treat numerous neurogenic inflammatory conditions. Neuromodulation has been shown, for example, to result in increased energy and motivation. See, e.g., U.S. Pat. Nos. 9,014,811, 9,002,458, 9,233,244, 9,399,126 and 9,333,334. The effect is comparable to caffeine or energy drinks available in the market today, though the effect can be stronger in certain individuals.

Despite the research to date on TES neuromodulation, existing systems and methods for delivering TES are lacking. In particular, miniaturized systems that incorporate hardware components with a low profile, comfortable, and/or familiar form factor for convenient, intuitive, easy to use, comfortable, and on-the-go TES free from cumbersome electrical wires, have been lacking.

SUMMARY OF THE DISCLOSURE

Described herein are apparatuses, including devices (e.g., neuromodulators) and systems (e.g., neuromodulation systems) that are or include a limited-use (1, 2, 3, 4, etc. uses), entirely self-contained wearable neuromodulator. These devices are specifically configured using one or more of the features described herein to be lightweight (e.g., 20 g or less, such as 19 g or less, 18 g or less, 17 g or less, 16 g or less, 15 g or less, 14 g or less, etc.) and highly flexible, while resisting damage. The apparatuses may be thin (e.g., 1 cm thick or less, 0.9 cm thick or less, 0.8 cm thick or less, 0.7 cm thick or less, 0.6 cm thick or less, 0.5 cm thick or less, 0.4 cm thick or less, 0.3 mc thick or less, etc.) including the power source, circuitry and electrode(s). Finally, these apparatuses may reliably and robustly deliver a therapy waveform (electrical waveform) that is effective to provide the one or more neuromodulatory effects described explicitly herein, including inducing an energized state, inducing a sympathetic nervous system effect, enhancing relaxation, enhancing a cognitive effect (e.g., enhancing memory, etc.), and/or treating a disorder, including neurogenic inflammatory conditions and autoimmune disorders such as psoriasis.

In particular, these devices may be extremely simple and easy to use to lower the barrier of adoption. Any of these devices may be specifically configured to operate robustly without requiring a user to adjust any controls. The apparatus may automatically turn on/off and may run autonomously. In some variations the apparatus may be configured to turn on (or be placed into a 'ready' mode) when released from its packaging or when a circuit interrupt is removed after removing from its packaging. The circuit interrupt may be a pull tab, pin, deflectable contact, or the like that may make an electrical connection between the power supply (e.g., battery, capacitor, etc.) and the control circuitry. Upon removal from the skin, these devices may shut down automatically to preserve power and be ready for the next use without substantially draining the power source. Sensing and control circuits may eliminate factors such as skin capacitance and soft tissue resistance to provide a uniform amount of stimulation without regard to user-to-user variability, thus eliminating the complex "intensity adjust dial" that prior art stimulators used and thereby limited general adoption.

The neuromodulators (which may also be referred to equivalently herein as neuromodulators) may be useful for either medical use and/or for consumer applications; these apparatuses may be configured as limited-number-of-use (e.g., single-use, useable for 2 sessions, useable for 3 sessions, etc.), and may be disposable devices. The apparatuses descried herein may have significant cost and use/compliance advantages that may enhance user's adoption and experience with the apparatus. The neuromodulators described herein may be skin-wearable neuromodulation apparatuses that use very low power and are adapted for comfort. Thus, described herein are very low cost, limited-number-of-use/disposable product that are still capable of providing reliable and effective neuromodulation.

As mentioned above, the apparatuses described herein may be configured to avoid controls and improve usage and compliance. In any of the variations described herein, the apparatus may be configured so that it is adhesively secured to the skin via one or more regions of hydrogel material. The hydrogel may be in contact with an electrode. In general, the apparatus may be configured as a thin, flexible 'stack' of laminate components in which the electrodes (including the adhesive hydrogel) are on the substrate, while the power source and circuitry are positioned above the substrate. In any of these apparatuses, the power source and circuitry may be held between a flexible (e.g., fabric) cover that encloses the power source and circuitry and in some variations wraps around them. A frame may hold the power source and/or circuitry and may be attached to the substrate and/or it may be allowed to move (or 'float') within the fabric enclosure relative to the substrate, which may enhance flexibility.

The apparatus may be any shape, e.g., round, oval, triangular, rectangular, etc. and may have rounded edges, and may be thin, e.g., having thickness of less than about 1 cm (e.g., less than 0.8 cm, less than 0.7 cm, less than 0.5 cm, less than 0.4 cm, etc.) at the average or maximum height. In some variations the maximum diameter of the apparatus may be less than about 10 cm (e.g., less than about 9 cm, less than about 8 cm, less than about 7.5 cm, less than about 7 cm, less than about 6 cm, etc.). These dimensions, as well as the use of a fabric material as the cover, may allow the device to be sufficiently lightweight (e.g., less than 20 g, less than 18 g, less than 17 g, less than 15 g, less than 12 g, etc.) so that the electrodes, and particularly the hydrogel portion of the electrodes, may secure the apparatus to the subject's skin without requiring an additional support or adhesive.

As mentioned, any of these devices may be configured so that they include a circuit interrupt that prevents the power source from making electrical contact with the control circuitry until the circuitry interrupt is manually or automatically removed. For example, the apparatus may be stored (packaged) ready for use but with the circuit interrupt between the control circuit and the power source (e.g., battery). When the circuit interrupt is removed, the battery may be placed in electrical contact with the control circuit placing the apparatus into a 'ready' or standby mode, or in some variations may begin applying the waveform.

Any of the apparatuses described herein may be configured so that the apparatus enters a standby/ready mode in which the waveform is not applied until the apparatus confirms that the electrodes (e.g., the hydrogel) is in contact with skin, meaning it is safe to apply the energy. Skin contact may be detected by, for example, detecting an electrical property between the electrodes (e.g., anode and cathode) forming the apparatus. The electrical property may be (or may be related to or equivalent to) the impedance. The apparatus may periodically or continuously detect the electrical property (e.g., impedance) between the electrodes and may permit the delivery of the waveform only when the electrical property (e.g., impedance) is within a range of values that indicate contact with skin.

In any of the apparatuses described herein, the device may not include any other controls, and specifically may not have any controls for adjusting the applied waveform (including the intensity, frequency, duration, etc.). The waveform and it's time sequence of changes may be predetermined and configured to achieve the desired effect as described in greater detail below. The predetermined waveform may include operating for a predetermined time period (e.g., 4 minutes or more, 5 minutes or more, 10 minutes or more, 12 minutes or more, 15 minutes or more, 17 minutes or more, 20 minutes or more, etc.). Thus, the apparatus may be extremely simple to operate.

The apparatuses described herein may be configured to allow two uses, three uses, or in some variations more than three uses (e.g., four uses, 5 uses, etc.). Thus, the apparatus may be configured to be used once, then removed and used again later. For example, the apparatus may be configured to be removed from a packaging (e.g., a pouch, such as a foil pouch), and the circuit interrupt removed, peeled off of a liner so that the electrode(s) hydrogel is exposed and may be placed on the subject's skin (e.g., neck, head, etc.) and allowed to deliver the waveform. As mentioned above, the apparatus may detect that it's been placed on the skin and may operate autonomously to deliver the waveform until either the waveform is completed (e.g., after the pre-determined duration) or until it is removed from the skin, which may be automatically detected. The device may then be in a delayed mode, and can be removed from the skin for re-applying later for a second use. In some variations the device may enter into a sleep or dormant mode until it can again deliver a waveform. For example, the apparatus may enter into a dormant mode that lasts until it can be activated again (e.g., by detecting skin contact and/or automatically starting) after a predefined off-time, e.g., of 5 min or more, 10 min or more, 15 min or more, 20 min or more, 30 min or more, etc. After the dormant mode, the device may be re-activated to deliver a subsequent (e.g., second) waveform, e.g., after removal of a second circuit interrupt, such as a pull tab. The second circuit interrupt may trigger the delivery of the subsequent use waveform, which may be the same or different from the first use waveform.

In variations including a second (or more) use configuration, the apparatus may include a second or additional hydrogel that is exposed by removing all or part of the first set of electrode hydrogel. For example, a first outer layer of hydrogel may form part of a first electrode and a second outer layer of hydrogel may form part of a second electrode. Additional hydrogel layers may underlie the first and/or second hydrogel layers and may be separated by one or more release layers. After the outermost hydrogel layer(s) are used to deliver a waveform, the device may be removed from the skin and, before re-applying the device to the skin, the user may remove the release layer to remove the outer layer(s) of hydrogel, exposing one or more new, fresh hydrogel layers that are also in electrical contact with the rest of the electrode. Alternatively or additionally, in some variations the hydrogel may be reactivated by adding a few drops of water. Any of the hydrogels may have a thickness sufficient to retain the device to the uses but prevented from being too thick, which makes the device taller than desired and may reduce the electrical efficiency. For example, any of the hydrogel layers may have a thickness of the hydrogel of less than about 2 mm (e.g., less than about 1.75 mm, less than about 1.5 mm, less than about 1.25 mm, less than about 1 mm, etc.).

In variations in which a release liner is included, the release liner may be connected to or may form part of the second circuit interrupt (e.g., pull tab) for activating or re-setting the control circuitry so that it enters into the second standby mode and prepares to deliver the subsequent waveform when an electrical property detects the presence of skin contact, as described above. Thus, in some variations, removing the outer hydrogel layer(s) (e.g., by removing the release layer and/or hydrogel) may remove the second circuit interrupt and allow activation of the second or subsequent waveform. The second or subsequent waveform(s) may be different than first (or other predicate) waveform. For example the subsequent waveforms may be lower in one or more of: frequency and/or intensity. For example, the second waveform may have an amplitude that is between about 10-30% lower in amplitude compared to the first waveform.

The release liner may be formed of a generally non-conductive material (e.g., electrically insulating material), but may have openings through which the adjacent layers of hydrogel may be in contact.

In general the waveforms described herein may be configured so that they deliver a constant current and a variable voltage; the voltage may be scaled between the first and subsequent waveforms. Examples and characteristics of effective predetermined waveforms are described below; for example, a predefined waveform may have a frequency of between about 100 Hz and 15 KHz and/or a charge per phase of between 0.1-10 microCoulombs. In some variations the waveform may have a duty cycle of between 1% and 50%.

In general, the apparatuses and methods described herein may be configured to deliver a change per phase that is between about 0.1 microCoulombs per phase and about 20 μC/phase (e.g., between about 0.1 μC/phase and about 10 μC/phase, e.g. between about 0.2 μC/phase and about 7 μC/phase, between about 0.2 μC/phase and about 5 μC/phase, between about 0.2 μC/phase and about 4 μC/phase, etc.). In general, the frequency may be configured to be between about 100 Hz and about 16 KHz, the percent duty cycle (e.g., the ratio of on to off time for the waveform) may be between about 1% and about 50%, and the percent DC may be between about 5% and 100%. In any of the apparatuses and methods described herein the waveform parameters may be specific to the indication for which the apparatus is intended. For example, the apparatuses described herein may include a pre-defined waveform that is monophasic or biphasic; in some variations, such as the use of the apparatuses described herein to treat a dermatological or other therapeutic indication, a biphasic waveform may be used, and the charge per phase may be between about 0.1 μC/phase and 4 μC/phase; the frequency may be between about 400 Hz and about 5 KHz (e.g., between 500 Hz and 4 KHz). The percent duty cycle may be between about 10% and about 40%, and the DC percentage may be between about 1%-70% (e.g., 4%-65%). The device may be applied to the back/midline of the user's neck.

In some variations, for indications in which an energizing effect is intended, the charge per phase may be between about 0.5 μC/phase and about 2 μC/phase, and the frequency may be between about 100 Hz and about 1600 Hz. The percent duty cycle may be between about 1% and about 20%, and the DC percentage may be between about 90%-100%. The device may be applied slightly behind the user's ear (e.g., over the mastoid region).

Indications in which a relaxation effect is intended, the device may be applied to the back of the user's neck (e.g., on or near the midline) and the charge per phase may be between about 0.1 and about 5 μC/phase. (e.g., between about 0.2 and about 3 μC/phase), and the frequency may be between about 1 KHz to about 16 KHz (e.g. between about 2 KHz and about 15 KHz). The percent duty cycle may be between about 10% and about 50%, and the DC percentage may be between about 70%-100%.

In indications in which memory enhancements are intended, the device may be applied to the forehead and/or temple regions with a common reference electrode targeting the prefrontal cortex and other brain regions, a sinusoidal, theta-like wave with a frequency of between 4-8 Hz and a biphasic peak to peak intensity of 1.5 mA may be applied for a period of at least 5 minutes.

The methods and apparatuses described herein may, in particular, be configured so that the waveforms shift (or oscillate) around one or more of frequency, center amplitude or center duty cycle by between 2% and 30% during the course of the application of the waveform. The oscillation can be variable or constant. Such waveforms may be referred to as pendulum waveforms. For example, a pendulum waveform 'swings' back and forth around a center frequency, center amplitude, or center duty cycle. In some variations the frequency is oscillated about a center frequency and the oscillations do not have to be symmetric. The pendulum cycle may take, e.g., 2 to 20 seconds (e.g. about 7-9 seconds, such as about 8 seconds) for the full cycle. The oscillation may be stepped (e.g., changed abruptly) or smooth (e.g., changed in a sinusoidal manner).

Pendulum waveforms may provide an improvement because the change or oscillation in parameters are generally better since they prevent adaptation. By sweeping over a range, the sensation and effect may be more likely to work for a larger number of different people, who may otherwise vary anatomically and biologically in that particular region with respect to nerve anatomy/physiology and sensory responses.

As mentioned above, any of the apparatuses described herein may include a fabric, and in particular an elastomeric fabric, material. The use of an elastomeric fabric as part of the body of the device (including the cover, and/or in some variations the substrate) may enhance the flexibility, reduce the profile/size, and may reduce the weight of the apparatus. As used herein a fabric may include woven and non-woven fabrics, including fabrics formed of sheets or layers of synthetic material (e.g., plastics, polymers, etc.). In some variations the fabric may be a highly compliant material. Examples of appropriate fabrics may include, but are not limited to: elastomeric polymers, elastomeric cotton (e.g., cotton/nylon blends, such as 95% cotton, 5% nylon, etc.), synthetic fibers, nylon fabrics, etc.

The fabric material may be used to wrap and/or cover the power source and/or control circuitry, and may be coupled to (e.g., adhesively bonded to) the substrate for the electrodes. In any of these variations the fabric may include an adhesive on one side, such as an acrylic adhesive. The fabric may form a cover that is compliant, and encloses all or part of the power supply and/or the circuitry. The fabric material may be woven, knitted, braided, or the like.

Any of the apparatuses described herein may include one or more pairs of electrodes (anode/cathode), and/or may have a three-electrode configuration (e.g., two cathodes, one anode). The electrodes may include a hydrogel that is electrically conductive and configured to contact the subject's skin. In general, the electrodes (including the hydrogel) may be arranged on a substrate so that they do not require a particular orientation. For example, the electrode may be arranged concentrically, so that a first electrode at least partially (e.g., 75% or more, 80% or more, 85% or more, 90% or more, 95% or more, etc.) surrounds the second electrode. Thus, the first and second electrodes (e.g., cathode and anode, or anode and cathode) may be configured as a bullseye pattern; the outer ring may be complete or interrupted (e.g., allowing electrical connection to the control circuitry). Thus, the first (outer ring) electrode may have a much larger area as compared to the second (inner shape) electrode, such as 2× or more, 3× or more, 3.5× or more, 4× or more, etc. the area of the second electrode. This concentric arrangement, in conjunction with the small maximum diameter of the device, may allow the apparatus to be applied in any orientation.

A wearable neuromodulation apparatus may include: a flexible (e.g., fibrous) substrate. The fibrous substrate may be a woven (e.g., formed of yarn or other fibers of material) or non-woven (e.g., paper) materials. In some variations, these fibrous substrates may have a shape memory wherein the flexible fibrous substrate is configured to return to a set shape after being folded or bent. Any of these apparatuses may also include: a control circuit attached to the fibrous substrate; a power source attached to the fibrous substrate in electrical communication with the control circuit; a first electrode on a first region of the fibrous substrate, wherein the first electrode comprises a first conductive gel pad over a first plurality of conductive filaments attached to the fibrous substrate; a second electrode on a second region of the fibrous substrate, wherein the second electrode comprises a second conductive gel pad over a second plurality of conductive filaments attached to the fibrous substrate; a first electrical connector coupling the first plurality of conductive filaments to the control circuit; and a second electrical connector coupling the second plurality of conductive filaments to the control circuit.

The flexible fibrous substrate may be a fibrous polyethylene terephthalate. In some variations, the flexible fibrous substrate comprises a woven material.

Any of these apparatuses may include a housing enclosing the control circuit and coupling the control circuit to the fibrous substrate. The housing may mechanically connect a first electrical contact for the control circuit to the first electrical connector and a second electrical contact for the control circuit to the second electrical connector.

Any of these apparatuses may include a control input electrically coupled to the control circuit and configured to control one or more of: power and intensity of the neuromodulation apparatus.

An outer surface area of the first electrode may be larger than an outer surface area of the second electrode (e.g., the anode may be larger than the cathode, or vice-versa).

The plurality of conductive filaments may comprise a mesh of conductive filaments. For example, the plurality of conductive filaments may be interwoven into the fibrous substrate. In some variations, the plurality of conductive filaments comprises a yarn with conductive filaments and insulating filaments. The plurality of conductive filaments may be stainless steel filaments.

The plurality of conductive filaments may be coupled to the substrate in any appropriate manner, including interweaving, and in some variations, adhesively attaching to the fibrous substrate.

Any appropriate electrical connector may be used. For example, the electrical connector(s) may comprise one or more of: a conductive yarn, a wire, or a printed electrical trace.

Any of these devices may include a flexible cover over the control circuitry. The cover may be formed of the substrate.

For example, described herein are wearable neuromodulation devices that include: a flexible woven substrate; a control circuit attached to the woven substrate; a power source attached to the woven substrate in electrical communication with the control circuit; a first electrode on a first region of the woven substrate, wherein the first electrode comprises a first conductive gel pad over a first plurality of conductive filaments attached to the woven substrate; a second electrode on a second region of the woven substrate, wherein the second electrode comprises a second conductive gel pad over a second plurality of conductive filaments attached to the woven substrate; a first electrical connector coupling the first plurality of conductive filaments to the control circuit; and a second electrical connector coupling the second plurality of conductive filaments to the control circuit.

The woven substrate may comprise a woven insulating material. For example, the woven substrate may be woven from a polymeric yarn. In some variations, the woven substrate is knitted.

The plurality of conductive filaments may comprises a mesh of conductive filaments; this mesh may be interwoven into the woven substrate and/or attached to the woven substrate. For example, the plurality of conductive filaments may comprise a yarn with conductive filaments and insulating filaments.

Any of the apparatuses described herein may be configured as limited-number-of-use, wearable neuromodulation device that provide a predetermined waveform having a very high electrical efficiency, so that the power requirements may be minimized. The limited-number-of-use applicator apparatus may be configured to provide over x minutes of electrical neuromodulation (e.g., 5 min, 7 min, 10 min, 15 min, 20 min, etc.) without requiring recharging, and may include one or more sensors (e.g., impedance sensing circuitry and/or logic) to determine when the device is in contact with the skin and ready to apply energy. For example, a limited-number-of-use wearable device may include: a flexible (in some variations, fibrous) substrate; a power source above substrate; a control circuit in electrical communication with the power source and configured to provide constant current pulsing, further wherein the control circuit comprise a switch configured to generate a DC voltage that changes amplitude over time to maintain constant current pulsing, the control circuit further comprising an accumulator configured to store energy from the power source and provide energy for the constant current pulsing; a pair of electrodes on the substrate. In some variations each electrode may have a conductive gel pad over a plurality of conductive filaments attached to the substrate. Each electrode may be electrically coupled to the control circuit via an electrical conductor. The control circuitry and/or power source may float relative to the substrate (e.g., may not be rigidly connected to it, but allowed to move (though constrained by a cover, such as a fabric cover).

In any of the apparatuses described herein, the power source may be a battery having less than a 50 milliamp hour capacity. For example, the power source may be one or more alkaline batteries in series having an instantaneous current output of less than 20 milliamps. In some variations, the maximum voltage output for the device is between 10 V and 50 V. In some variations, the power source is a 30 mA*hr (e.g., 30 C, 3.7 V) source.

In some variations, the control circuit may be configured to provide an amplitude-modulated carrier waveform having a trapezoidal envelope, wherein the carrier waveform comprises a pair of repeating pulses.

In any of these apparatuses, energy may be accumulated from the battery and boosted in voltage to provide the constant current pulsing for neuromodulation. For example, the switch may be a switching transistor that is configured to generate a plurality of kick-up pulses feeding into an inductor (e.g., accumulator). The inductor may be in communication with one of the electrodes of the pair of electrodes. The control circuitry may also include smoothing circuitry to smooth the ripples from the kick-up pulsing.

Described herein are wearable neuromodulator apparatuses (e.g., devices) that include: a flexible substrate; a first electrode; a second electrode on the flexible substrate; a battery; a control circuitry in communication with the first electrode and the second electrode; a circuit interrupt removably coupled with the control circuitry, wherein the circuit interrupt is interposed between the battery and the control circuitry so that removing the circuit interrupt powers the control circuitry, further wherein the control circuitry is configured to deliver a predefined waveform between the first and second electrodes after the circuit interrupt is removed, wherein the device weighs 20 g or less.

A wearable neuromodulator device may include a flexible substrate, a first electrode; a second electrode on the flexible substrate; a battery; a control circuitry, wherein the control circuitry has a first mode of operation in which the battery is disengaged from the control circuitry and a second mode of operation in which the battery is engaged with the control circuitry, further wherein the control circuitry is configured to deliver a predefined waveform between the first and second electrodes when the battery is engaged with the control circuitry, wherein the waveform has a frequency of between 100 Hz and 15 KHz and delivers a charge per phase of between 0.1-10 microCoulombs; and a circuit interrupt removably coupled with the control circuitry and configured to switch the control circuitry from the first mode to the second when the circuit interrupt is removed.

In any of the apparatuses described herein the circuit interrupt may be a pull tab, pull pin, etc. and may be formed of a material that is electrically insulating and prevents electrical contact between the battery and the control circuitry. For example, the pull tab or pin may interrupt the circuitry by holding apart a biased contact that is released when the interrupt is pulled out, allowing the circuit to close and power to be applied to the control circuit.

In any of these apparatuses, the first electrode may comprise a first adhesive hydrogel and the second electrode may comprise a second adhesive hydrogel.

As mentioned above, any of these apparatuses may weight 20 g or less (e.g., 15 g or less, 10 g or less, etc.) which may allow the device to be worn just by the adhesive properties of the standard electrically conductive hydrogel without disrupting the electrical contact between the skin and the hydrogel. Any of these apparatuses may have a maximum diameter of 10 cm or less (e.g., 9 cm or less, 8 cm or less, 7 cm or less, 6 cm or less, etc.), and an average or maximum thickness of 1 cm or less (e.g., 0.8 cm or less, 0.7 cm or less, 0.6 cm or less, 0.5 cm or less, etc.).

As mentioned, any of these apparatuses may include a flexible cover wherein the battery and control circuitry are between the flexible cover and the flexible substrate. The flexible cover may be a fabric.

In any of these apparatuses, the control circuitry may be configured to generate and deliver the pre-defined waveform between the first and second electrodes when the battery is engaged with the control circuitry and an impedance between the first and second electrodes is within a pre-defined range (e.g., indicating that the device is being worn on skin). The predefined waveform is configured to run for 25 minutes or less (e.g., 20 min or less, 15 min or less, 10 min or less, 5 min or less, between 3-25 min, between 3-20 min, between 3-15 min, between 3-10 min, etc.).

As discussed above, in general, any of these apparatuses may not include any user inputs or controls other than the circuit interrupt. Specifically, and of these apparatuses may not include a control (e.g. knob, dial, button, slider, etc.) or input for adjusting the waveform. The waveform may be preloaded into the apparatus.

As mentioned above, the waveform may have a frequency of between about 100 Hz and 1.6 KHz; the waveform may have a charge per phase of between about 0.1-5 μC/phase; and the waveform may have a DC percentage of between 80-100%. In any of these apparatuses and methods the waveform may have a current of between about 1 and 20 mA.

In any of these apparatuses, the circuit interrupt may be removable from the apparatus. For example, the circuit interrupt may be a pull tab or pin that is removable from the apparatus after it is removed from the packaging but before it is applied to the skin.

For example, a wearable neuromodulator device may include: a flexible substrate; a first electrode on the flexible substrate; a second electrode on the flexible substrate; a battery; a control circuitry, wherein the control circuitry has a first mode of operation in which the battery is disengaged from the control circuitry and a second mode of operation in which the battery is engaged with the control circuitry, further wherein the control circuitry is configured to deliver a pre-defined waveform between the first and second electrodes when the battery is engaged with the control circuitry and an impedance between the first and second electrodes is within a pre-defined range, wherein the waveform has a frequency of between 100 Hz and 15 KHz and delivers a charge per phase of between 0.1-10 microCoulombs; and a pull tab removably coupled with the control circuitry and configured to switch the control circuitry from the first mode to the second when the pull tab is pulled, wherein the device weighs 20 g or less.

A wearable neuromodulator device, the device comprising: a flexible substrate; a first electrode on the flexible substrate; a second electrode on the flexible substrate; a battery; a control circuitry, wherein the control circuitry has a first mode of operation in which the battery is disengaged from the control circuitry and a second mode of operation in which the battery is engaged with the control circuitry, further wherein the control circuitry is configured to deliver a pre-defined waveform between the first and second electrodes when the battery is engaged with the control circuitry and an impedance between the first and second electrodes is within a predefined range, wherein the waveform has a frequency of between 100 Hz and 15 KHz and delivers a charge per phase of between 0.1-10 microCoulombs; a cover covering the flexible substrate so that the battery and control circuitry are enclosed between the cover and the flexible substrate, wherein the thickness of the device between the cover and the flexible substrate is less than 5 mm; and a pull tab removably coupled with the control circuitry and configured to switch the control circuitry from the first mode to the second when the pull tab is pulled, wherein the device has a principle diameter that is between 2 cm and 10 cm.

Any of these apparatuses (limited-number-of-use apparatuses) may be configured for two or more uses. For example, a wearable neuromodulator device may include: a flexible substrate; a first electrode and a second electrode on the flexible substrate; a first hydrogel layer in electrical communication with the first electrode and a second hydrogel layer in electrical communication with the second electrode; a third hydrogel layer in electrical communication with the first hydrogel layer; a removable release layer, wherein the first hydrogel layer is separated from the third hydrogel layers by the release layer; a battery; a control circuitry; and a circuit interrupt removably coupled with the control circuitry, wherein the circuit interrupt is interposed between the battery and the control circuitry so that removing the circuit interrupt powers the control circuitry, further wherein the control circuitry is configured to deliver a first predefined waveform between the first and second electrodes after the circuit interrupt is removed, and a second predefined waveform between the first and second electrodes after the release layer is removed. As mentioned above, the release layer may be coupled to the control circuitry.

In any of these apparatuses, the control circuitry may be configured to deliver the first predefined waveform between the first and second electrodes after the circuit interrupt is removed and an impedance between the first and second electrodes is within a predefined range, and the second predefined waveform between the first and second electrodes after the release layer is removed and the impedance between the first and second electrodes is within the predefined range.

In some variations the first predefined waveform is the same as the second predefined waveform. Alternatively, in some variations, the second predefined waveform has an intensity that is between 5-50% lower than the first predefined waveform. The first predefined waveform may be configured to run for between 4-25 minutes.

In any of these apparatuses, the control circuitry may be configured to stop delivering the first or second predefined waveform if the impedance between the first and second electrode is outside of the predefined range. Thus, the apparatus may be configured to periodically and/or continuously monitor the impedance between the electrodes to confirm that the device is on the skin (e.g., every 1 ms, every 5 ms, every 10 ms, every 20 ms, every 50 ms, every 100 ms, etc.).

The control circuitry may be configured so that the first predefined waveform and the second predefined waveform each comprise a constant current and a variable voltage.

As mentioned above, the release layer may comprise a plurality of openings therethrough to permit electrical contact between the first hydrogel and the third hydrogel. These openings may be shaped (e.g., round, triangular, etc.) and may be oriented to assist in removing the release layer from an underlying layer of hydrogel. The release layer may be an insulating material; in some variations the release layer is instead an electrically conductive material (e.g., the release layer may be formed of an electrical insulating material impregnated with conductive particles, etc.). Typically, the release layer comprises a non-stick or low-stick material (e.g., a waxed material, etc.).

For example, a wearable neuromodulator device may include: a flexible substrate; a first electrode and a second electrode on the flexible substrate; a first hydrogel layer in electrical communication with the first electrode and a second hydrogel layer in electrical communication with the second electrode; a third hydrogel layer in electrical communication with the first hydrogel layer; a fourth hydrogel layer in electrical communication with the second hydrogel layer; a removable release layer, wherein the first and second hydrogel layers are separated from the third and fourth hydrogel layers by the release layer; a battery; a control circuitry; and a pull tab removably coupled with the control circuitry, wherein the pull tab is interposed between the battery and the control circuitry so that removing the pull tab powers the control circuitry, further wherein the control circuitry is configured to deliver a first predefined waveform between the first and second electrodes after the pull tab is removed, and a second predefined waveform between the first and second electrodes after the release layer is removed, wherein the second predefined waveform has an intensity that is between 5-50% lower than the first predefined waveform.

Any of these apparatuses may include a fabric cover material, as described above. For example, a wearable neuromodulator device may include: a flexible substrate; a first electrode; a second electrode on the flexible substrate; a battery; a control circuitry coupled to the first electrode and the second electrode, wherein the control circuitry is configured to deliver a predefined waveform between the first and second electrodes when the battery is powering the control circuitry; and an elastic cover wherein the battery and control circuitry are between the cover and the flexible substrate, further wherein the device weighs 20 g or less, has a maximum thickness of 7 mm or less, and a maximum diameter of 10 cm or less. The elastic cover may comprise an elastomeric fabric, e.g., an elastomeric cotton. The elastic cover may comprise a nonwoven elastomeric material. In some variations the battery and control circuitry are at least partially wrapped in the elastic cover.

The elastic cover may be secured over the flexible substrate, e.g., the elastic cover may be adhesively secured to the flexible substrate. Any of these apparatuses may include a frame securing the battery and the control circuitry, wherein the frame is covered by the elastic cover.

A wearable neuromodulator device may include: a flexible substrate; a first electrode on the flexible substrate; a second electrode on the flexible substrate; a battery; a control circuitry coupled to the first electrode and the second electrode, wherein the control circuitry is configured to deliver a predefined waveform between the first and second electrodes when the battery is powering the control circuitry; and an elastic cover comprising an elastomeric fabric that is adhesively secured to the flexible substrate wherein the battery and control circuitry are at least partially wrapped in the cover. The device may weighs 20 g or less, have a maximum thickness of 7 mm or less, and a maximum diameter of 10 cm or less.

A wearable neuromodulator device may include: a flexible substrate; a first electrode that is concentrically arranged around a second electrode, wherein the first and second electrodes are on the flexible substrate; a battery; a control circuitry coupled to the first electrode and the second electrode, wherein the control circuitry is configured to deliver a predefined waveform between the first and second electrodes when the battery is powering the control circuitry; and an elastic cover attached to the flexible substrate, wherein the battery and control circuitry are between the cover and the flexible substrate, further wherein the device weighs 20 g or less.

The first electrode may completely surround the second electrode; in some variations the first electrode surrounds more than 75% (e.g., 80%, 85%, 90%, etc.) of the second electrode, as described above. The first electrode may be configured as a cathode and the second electrode may be configured as an anode. The predefined waveform may be configured to run for 15 minutes or less.

A wearable neuromodulator device may include: a flexible substrate; a first electrode comprising a first hydrogel; a second electrode comprising a second hydrogel, wherein the first electrode is concentrically arranged around the second electrode, further wherein the first and second electrodes are on the flexible substrate; a battery; a control circuitry coupled to the first electrode and the second electrode, wherein the control circuitry is configured to deliver a predefined waveform between the first and second electrodes when the battery is powering the control circuitry and an impedance between the first and second electrodes is within a predefined range, further wherein the waveform has a frequency of between 100 Hz and 15 KHz and delivers a charge per phase of between 0.1-10 microCoulombs; and an elastic cover attached to the flexible substrate, wherein the battery and control circuitry are between the cover and the flexible substrate, further wherein the device weighs 20 g or less.

Any of these methods and apparatuses may be configured to deliver a pendulum waveform, as described above. For example, a wearable neuromodulator device may include: a flexible substrate; a first electrode; a second electrode on the flexible substrate; a battery; a control circuitry coupled to the first electrode and the second electrode, wherein the control circuitry is configured to deliver a predefined waveform between the first and second electrodes when the battery is powering the control circuitry, further wherein the predefined waveform has a frequency of between 100 Hz and 15 KHz, a duty cycle of between 1% and 50% and a charge per phase of between 0.1-10 microCoulombs, further wherein the waveform oscillates one or more of frequency, center amplitude or center duty cycle with an oscillation frequency of between about 2-20 seconds; and a cover wherein the battery and control circuitry are between the cover and the flexible substrate. The predefined waveform may be biphasic or monophasic.

A wearable neuromodulator device may include: a flexible substrate; a first electrode on the flexible substrate; a second electrode on the flexible substrate; a battery; a control circuitry coupled to the first electrode and the second electrode, wherein the control circuitry is configured to deliver a predefined waveform between the first and second electrodes when the battery is powering the control circuitry, further wherein the predefined waveform has a frequency of between 100 Hz and 2 KHz, a duty cycle of between 1% and 50% and a charge per phase of between 0.4-4 microCoulombs, further wherein the waveform oscillates one or more of frequency, center amplitude or center duty cycle with an oscillation frequency of between about 2-20 seconds; and a cover wherein the battery and control circuitry are between the cover and the flexible substrate.

Also described herein are methods of using any of the apparatuses described herein, including methods of using them for one or more indications, such as to induce a energized state in the user, to induce a relaxed state in the user, to improve a cognitive state (e.g., to enhance or improve memory), to treat a disorder, including ADHD, neurogenic inflammation, autoimmune disorders such as psoriasis, general anxiety disorders, sleep-related disorders (e.g. insomnia, etc.) and/or improving sleep (including but not limited to increasing sleep duration, reducing sleep onset, etc.).

For example described herein are methods of operating or applying a neuromodulator (neuromodulator) as described herein. A method may include: engaging a battery of a wearable neuromodulator device with a control circuitry of the wearable neuromodulator device when a circuit interrupt of a wearable neuromodulator device is removed; delivering a pre-defined waveform between a first electrode and a second electrode when the battery is engaged with the control circuitry and an impedance between the first and second electrodes is within a pre-defined range indicating that the device is place on a skin surface; and stopping delivery of the pre-defined waveform when the impedance between the first and second electrodes is outside of the pre-defined range or when the waveform is complete. The method may include a method of inducing an energized cognitive state in the subject, a method of enhancing the subject's sympathetic nervous system, a method of relaxing the subject/inducing relaxation, a method of enhancing cognition (e.g., memory), a method of treating a disorder such as general anxiety disorder, ADHD, rheumatoid arthritis, psoriasis, a method of treating a sleep-related disorder, etc.

Any of these methods may include removing the apparatus from a packaging (e.g., a foil package), removing an adhesive backing over the hydrogel portion of the electrodes, and/or placing the wearable neuromodulator device onto a subject's skin. For example, placing the device on the subject's neck (e.g., on a central region of the subject's neck, on a side of the subject's neck/behind the subject's ear), or on the subject's forehead. The device may be configured to be retained on the skin by just the electrode hydrogel (without requiring any additional adhesive or securement such as a strap, etc.). For example, the device may weigh 20 g or less, have a maximum diameter of 10 cm or less, and/or a maximum thickness of 1 cm or less. Placing the device may comprises bending the device to fit the subject's skin, further wherein the device may include a flexible cover over a battery and the control circuitry, so that the battery and control circuitry are between the flexible cover and a flexible substrate holding the first electrode and the second electrode (e.g., the flexible cover may be a fabric, as described above). The predefined waveform may be configured to run for 25 min or less (e.g., 20 minutes or less, 15 minutes or less, 10 minutes or less, 7 minutes or less or 5 minutes or less, 4 minutes or less etc.). As mentioned, the device may not include any user inputs or controls other than the circuit interrupt. Any of these methods may include removing the circuit interrupt from the device. Removing the device from the skin may cause the device to go into a standby mode or a locked mode in which the waveform is not applied.

For example, a method of inducing an energized state in a subject may include: placing a wearable neuromodulator device onto the subject's neck so that a first electrode and a second electrode contact the subject's skin, wherein the wearable neuromodulator device weights 20 g or less; engaging a battery of the wearable neuromodulator device with a control circuitry of the wearable neuromodulator device when a circuit interrupt of a wearable neuromodulator device is removed; delivering a pre-defined waveform between the first and second electrodes when the battery is engaged with the control circuitry and an impedance between the first and second electrodes is within a pre-defined range indicating that the device is place on a skin surface, wherein the waveform has a frequency of between 100 Hz and 15 KHz and delivers a charge per phase of between 0.1-5 microCoulombs; and automatically stopping delivery of the pre-defined treatment plan when the impedance between the first and second electrodes is outside of the pre-defined range or when the waveform is complete.

Any of these methods may include using pendulum waveforms. For example, a method may include: placing a wearable neuromodulator device onto a subject's skin; delivering a pre-defined waveform between the first and second electrodes when an impedance between a first electrode and a second electrode is within a pre-defined range indicating that the device is place on a skin surface, wherein the waveform has a frequency of between 100 Hz and 15 KHz, a duty cycle of between 1% and 50% and a charge per phase of between 0.1-5 microCoulombs, further wherein the waveform oscillates one or more of frequency, center amplitude or center duty cycle with an oscillation frequency of between about 2-20 seconds; and automatically stopping delivery of the pre-defined treatment plan when the impedance between the first and second electrodes is outside of the pre-defined range or when the waveform is complete.

A method of inducing an energized state in a subject may include: placing a wearable neuromodulator device onto the subject's neck so that a first electrode and a second electrode contact the subject's skin; delivering a pre-defined waveform between the first and second electrodes when an impedance between the first and second electrodes is within a pre-defined range indicating that the device is place on a skin surface, wherein the waveform has a frequency of between 100 Hz and 15 KHz, a duty cycle of between 1% and 50% and a charge per phase of between 0.1-5 microCoulombs, further wherein the waveform oscillates one or more of frequency, center amplitude or center duty cycle with an oscillation frequency of between about 2-20 seconds; and automatically stopping delivery of the pre-defined treatment plan when the impedance between the first and second electrodes is outside of the pre-defined range or when the waveform is complete.

A method of inducing a relaxed cognitive state in a subject may include: placing a wearable neuromodulator device onto the subject's neck so that a first electrode and a second electrode contact the subject's skin; delivering a pre-defined waveform between the first and second electrodes when an impedance between the first and second electrodes is within a pre-defined range indicating that the device is place on a skin surface, wherein the waveform has a frequency of between 1 KHz and 15 KHz, a duty cycle of between 1% and 50% and a charge per phase of between 0.1-5 microCoulombs, further wherein the waveform oscillates one or more of frequency, center amplitude or center duty cycle with an oscillation frequency of between about 2-20 seconds; and automatically stopping delivery of the pre-defined treatment plan when the impedance between the first and second electrodes is outside of the pre-defined range or when the waveform is complete.

A method of enhancing relaxation may include: placing a wearable neuromodulator onto a back of a subject's neck; removing a circuit interrupt of the wearable neuromodulator to engage a battery of a wearable neuromodulator with a control circuitry of the wearable neuromodulator; delivering a pre-defined waveform between a first electrode and a second electrode when the battery is engaged with the control circuitry and an impedance between the first and second electrodes is within a pre-defined range indicating that the device is place on a skin surface, wherein the pre-defined waveform has charge per phase of between 0.1-10 microCoulombs; and stopping delivery of the pre-defined waveform when the impedance between the first and second electrodes is outside of the pre-defined range or when the waveform is complete. Placing the wearable neuromodulator may comprise placing the device on central region of the back of the subject's neck. The pre-defined waveform may have a frequency of between 1 KHz and 18 KHz. The pre-defined waveform may have a charge per phase of between 0.1-1.2 µC. The pre-defined waveform may have a DC percentage of between 70-100%.

As mentioned, also described herein are techniques for enhancing sleep (reducing sleep latency, increasing time asleep, etc.), as well as methods of treating certain autoimmune disorders such as psoriasis. For example, described herein are method of enhancing sympathetic nervous system activity to treat psoriasis, the method comprising: placing a wearable neuromodulator on a the subject having psoriasis; removing a circuit interrupt of the wearable neuromodulator to engage a battery of a wearable neuromodulator with a control circuitry of the wearable neuromodulator; reducing the subject's psoriasis by automatically delivering a pre-defined waveform between a first electrode and a second electrode when the battery is engaged with the control circuitry and an impedance between the first and second electrodes is within a pre-defined range indicating that the device is place on a skin surface, wherein the pre-defined waveform has charge per phase of between 0.1-10 microCoulombs; and stopping delivery of the pre-defined waveform when the impedance between the first and second electrodes is outside of the pre-defined range or when the waveform is complete.

Also described herein are methods and apparatuses of enhancing or improving memory. Any of the apparatuses and features described above may be adapted as described herein for enhancing memory. For example, any of these apparatuses may include an additional electrode that may be separately positioned relative to the first and second electrode. In particular the first and second electrode of the body of the apparatus may be positioned over the subject's temple (on the side of the forehead) while the third electrode, e.g., cathode, may be positioned over the midline of the forehead. Thus the apparatus may include an extension arm that is between about 1-4 inches (e.g., between about 1-3 inches, between about 1-2.2 inches) from the edge of the concentric electrodes on the substrate. The extension arm may be formed of the substrate, which may be a flexible material (e.g., a flexible polymer, fabric, etc., as described herein). The control circuitry may apply the same pre-defined waveform to both the first and second and third (or third and second) electrodes, in a synchronous manner.

For example, a method of enhancing cognition may include: placing a wearable neuromodulator device weighing 20 g or less onto a subject's head; delivering, from a processor within the wearable device, a pre-defined waveform between a first electrode and a second electrode when an impedance between the first electrode and the second electrode is within a pre-defined range indicating that the device is on a skin surface, wherein the waveform has charge per phase of between 0.1-10 microCoulombs; and automatically stopping delivery of the pre-defined treatment plan when the impedance between the first and second electrodes is outside of the pre-defined range or when the waveform is complete.

As in any of the methods of use described herein, placing may comprise conforming the wearable neuromodulator device to the subject's head by allowing a flexible fabric cover over the wearable device to stretch. Similarly, delivering may comprise automatically delivering the predefined waveform without the subject operating a control or adjusting the predefined waveform. The method of enhancing cognition may comprise enhancing memory. Placing may comprise placing the first and second electrode over the subject's temple and placing a third electrode in a middle portion of the subject's forehead. The first and second electrodes may be placed on the subject's temple and forehead. The waveform may comprises a frequency of between about 4-8 Hz.

For example, a method of enhancing cognition, including memory may include: placing a wearable neuromodulator device weighing 20 g or less onto a subject's temple and forehead; automatically delivering, from a processor within the wearable device, a pre-defined waveform from a first electrode on the subject's temple and second electrode on the subject's forehead, when an impedance measured at either or both the first and second electrodes is within a pre-defined range indicating that the device is on a skin surface, wherein the pre-defined waveform has charge per phase of between 0.1-10 microCoulombs and comprises a frequency of between about 4-8 Hz; and automatically stopping delivery of the pre-defined treatment plan when the impedance is outside of the pre-defined range or when the waveform is complete.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3 is a table illustrating the relationship between gel pad thickness and distance to a target nerve within the body.

FIGS. 4A-4B illustrate examples of electrodes (e.g., anode and cathode, primary and return) including a gel pad region overlaying a plurality of current-distributing conductive fibers (e.g., stainless steel fibers) between the substrate and the conductive gel pads.

FIGS. 5A and 5B illustrate another example of a pair of electrodes (e.g., (e.g., anode and cathode, primary and return) that may be used, e.g., as part of a limited-number-of-use, wearable neuromodulator configured to be worn on a user's neck.

FIG. 6A is an exemplary schematic section through a protective frame (e.g., housing) for a control circuit and/or battery of a limited-number-of-use, wearable neuromodulator.

In FIG. 7, the wearable neuromodulator may be worn on the back of the user's neck.

In FIG. 12, a plurality of adjacent wearable devices are fabricated in a single layer that is then cut or otherwise divided into separate devices.

FIG. 14 illustrates an example of a woven material (e.g., woven polymeric material) to which a plurality of conductive filaments (e.g., stainless steel filaments) is coupled.

FIG. 15A is a sectional view through a portion of an electrode of a limited-number-of-use, wearable neuromodulator having a flexible substrate.

FIG. 15B show an enlarged view through a section of a conductive yarn including stainless steel fibers that may form part of an electrode, such as the one shown in FIG. 15A.

In FIG. 25A the apparatus is folded/bent, while in FIG. 25B the apparatus is shown returning to its shape.

FIG. 30A is a table illustrating exemplary descriptors for an amplitude-modulated carrier waveform having a trapezoidal envelope, wherein the carrier waveform comprises a pair of repeating pulses; these waveforms may be delivered by a limited-number-of-use wearable neuromodulator as described herein.

FIG. 30B is a table (table 3) illustrating parameters for exemplary neuromodulation as described herein.

FIGS. 31A-31H illustrate one example of a limited-number-of-use wearable neuromodulator as described herein. FIG. 31A is a top view, FIG. 31B is a bottom view, FIG. 31C is a top perspective view, FIG. 31D is a bottom perspective, FIG. 31E is a left side view, FIG. 31F is a front view, FIG. 31G is a right side view, FIG. 31H is a left side view, and FIG. 31I is a back view.

FIG. 32A is a top view, FIG. 32B is a bottom view, FIG. 32C is a top perspective view, FIG. 32D is a bottom perspective, FIG. 32E is a left side view, FIG. 32F is a front view, FIG. 32G is a right side view, FIG. 32H is a left side view, and FIG. 32I is a back view.

FIGS. 35A and 35B illustrates one method of wrapping a fabric cover over a battery and control circuitry.

FIG. 36 is an example of one variation of a limited-number-of-use neuromodulator apparatus as described herein, including two layers of hydrogel separated by a release layer (shown without a fabric cover).

FIG. 42 shows placement of a first release layer on the second (inner) electrode; FIGS. 43 and 44 show placement of the outer release layer on the first (outer) electrode that is concentrically around the second electrode. FIG. 45 illustrates placement of a second gel layer for the second (inner) electrode. FIG. 46 shows placement of the second gel layer for the first (outer) electrode.

FIG. 56A shows the neuromodulator from the front (showing the fabric cover wrapping around and covering the battery and control circuitry, while FIG. 56B shows the neuromodulator from the back, showing the electrodes (including the hydrogel forming the electrodes).

FIG. 57 shows one example of a subject wearing a neuromodulator such as the one shown in FIGS. 56A-56B for enhancing memory.

FIG. 58 illustrates the approximate placement of the electrodes over the target brain regions for enhancing memory as described herein.

FIG. 59 illustrate brain regions corresponding to the application of electrical energy received by the subject using the neuromodulator apparatus shown in FIGS. 56A-56B and 57 when a waveform configured for enhancing memory (e.g., having a frequency component between about 4-8 Hz) is applied.

DETAILED DESCRIPTION

The apparatuses described herein include limited-number-of-use neuromodulators that may be comfortably worn on the skin of a user to non-invasively apply transdermal electrical stimulation (TES). These apparatuses may be formed of a soft, compliant material, and may have a simplified user interface, which may not include any buttons or controls; these apparatuses (e.g., devices and systems, including neuromodulators) may be configured to run autonomously once applied. These apparatuses may also include improved power management features.

For example, any of these apparatuses may be configured to provide neuromodulation by applying a series of constant-current electrical pulses that change as a function of time to modulate the neural activities. This weight, size, simplicity of use as well as the parameters of the constant current pulses disclosed herein are specific to these apparatuses and may distinguish from other neurostimulators/neuromodulators, including muscle stimulators or TENS devices.

A limited-number-of-use apparatus as disclosed here may comprise two or more conductive gel (e.g. hydrogel) layers or pads that may form part of the electrodes, e.g., anode and cathode, and may be characterized by particular parameters for neuromodulation using these apparatuses. Specifically, the conductive gel pads used in any of the apparatuses described herein may be within a specific range of thicknesses, surface areas, and shapes. These parameters have been determined (after numerous trials) and are specific for the anatomy at the location of attachment.

In general, the apparatuses described herein may include a fabric material forming all or part of the apparatus, including the cover, a substrate onto which the electrodes are formed and/or the electrodes themselves. Thus, any of the apparatuses described herein may be self-contained, including a substrate (including a polymeric and/or woven substrate, as described below), on which two or more electrodes and/or gel pads connect via a flexible connector to control circuitry and a power source (e.g., battery) which may be attached to the body of the substrate or may 'float,' and be freely moveable relative to the substrate. The control circuitry may be pre-configured to include the treatment waveform(s) for applying a predetermined neuromodulation pattern. The entire structure may be flexible, and may be applied to any appropriate region of the body, but particularly the head, neck, etc.

Woven Substrates

Figure 1:
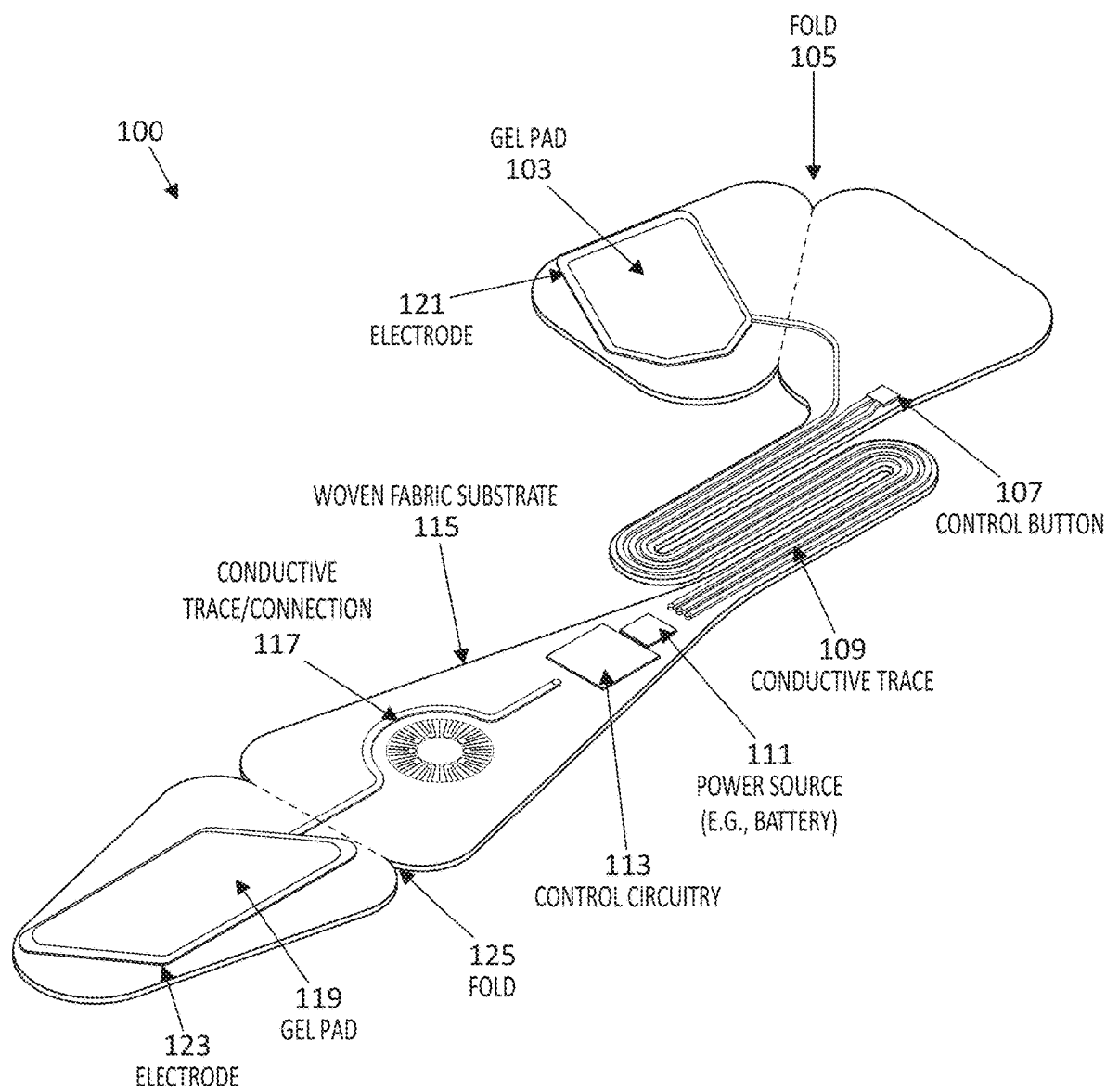
FIG. 1 is one example of a limited-number-of-use, wearable neuromodulator (e.g., neuromodulator) having a flexible (e.g., woven) substrate including control circuitry and electrodes; the cover is also formed of a flexible fabric.

In some, but not all, of the variations described herein the substrate may be a woven substrate. For example, FIG. 1 illustrates a first example of a limited-number-of-use neuromodulator apparatus. In FIG. 1, the substrate is a woven fabric 115 onto which all of the components of the system have been added. For example, the limited-number-of-use neuromodulator 100 includes two gel pads 103, 119, each positioned over an electrode 121, 123, (or forming part of the electrode) and each connected, via a flexible conductor (e.g., conductive trace 109, 117) to a control circuitry 113 and power supply 111. In this example, the neuromodulator includes a control button 107 that may be used to turn on/off the device and/or adjust the intensity and/or pause/stop the application of neuromodulation. As will be described in greater detail below, in some variations no additional button or control is included.

Any appropriate knitted or woven substrate may be used. For example, the substrate may be a blend conductive and insulating yarns of many varieties to enable the apparatus to be 'knit to shape'. As used herein, the term woven may be used generically to materials formed of one or more fibers or group of fibers (e.g., cables, filaments, threads, yarns, etc.). A knitted material is typically formed of a single strand (monofilament, poly-filament, etc.); other woven materials may be formed of multiple strands.

The apparatus shown in FIG. 1 may be adapted for use to the head (e.g., between the region behind the ear, such as the mastoid, and the neck, or behind the ear/mastoid and the temple. In use, the apparatus may be applied to the skin with the first end (e.g., gel pad 103) applied to one region, such as the mastoid region, and the second end (e.g., gel pad 119) applied to a second region, such as the neck (e.g., midline of the back of the user's neck) or in some variations, the temple. The substrate material may be soft and flexible, permitting the apparatus to conform comfortably to the subject's skin.

Figure 2A:
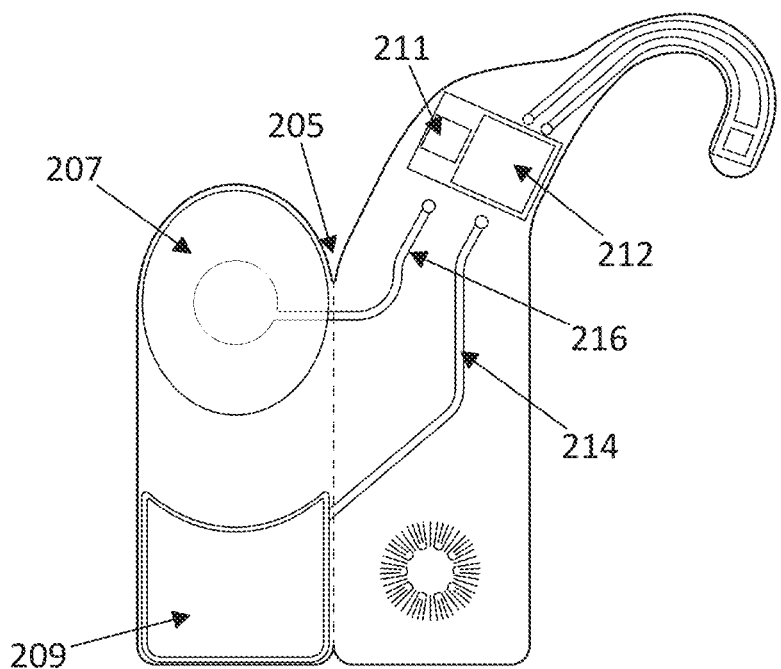
FIGS. 2A-2B show another example of a limited-number-of-use wearable neuromodulator configured to be worn behind a user's ear.
Figure 2B:
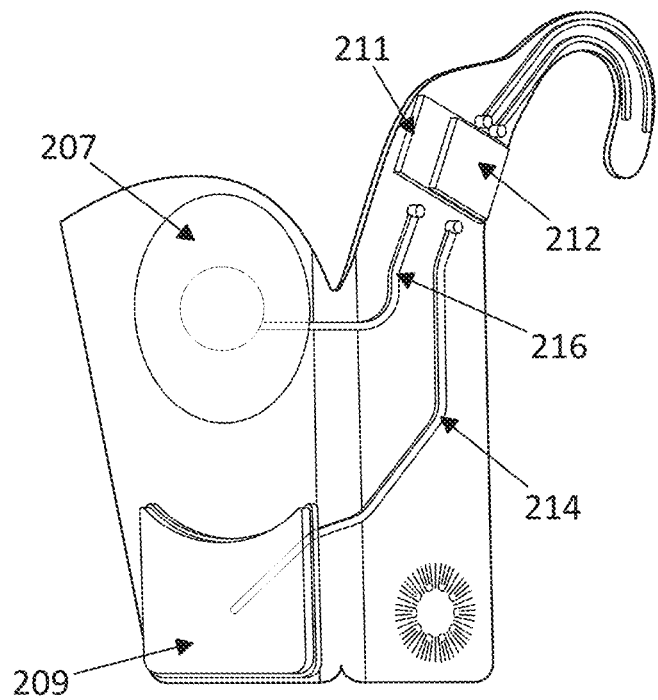

FIGS. 2A-2B illustrate another variation of an apparatus as described herein. In this example, the apparatus is configured to be a limited-number-of-use device that can be worn behind the user's ear. FIG. 2A shows an example of a printed device structure before folding (along the fold 205) into a finished device. This configuration may be behind the ear (e.g. mastoid) and may provide an "energy" (stimulating) effect in the user. In FIG. 2A, the oval gel pad 207 is configured to sit on top of a bony structure behind the user's ear. The partially concentric reference electrode 209 may at the neck around the bottom of the user's ear when the apparatus is worn. In FIG. 2A, the apparatus is shown unfolded; the substrate is flat, but may be folded (as shown in FIG. 2B) so that the gel pads 207, 209 above and electrically connected to the electrodes are on the back side of the substrate with the control circuitry 211 on the opposite (back) side, and connected by conductive traces 214, 216. The device may also include one (or more) inputs, e.g., buttons, dials, etc. FIG. 2B shows the device of FIG. 2A being folded.

As used herein the term "electrode" may refer to both the gel and the electrical connector and/or any other material forming the interface between the subject and the connection to the control circuitry.

In any of the apparatuses described herein, the conductive gel pad that connects electrically to the user's skin to apply neuromodulation may be configured within a range of dimensions that may be optimized for neuromodulation. For example, in some variations, the thickness of the gel may be related to the distance of the electrode (e.g., the outer surface of the gel) from the target nerve bundle, when the electrode is worn. This may be equivalent to the distance from the skin surface to the target nerve bundle. The applied electric field may be optimized to this gel thickness. For example, if the gel is too thin, the electric field may stimulate more of the surface nerve to create a discomfort. If the gel is too thick, then the field strength may be less than optimal at the neural bundle that we target.

The skin is not typically homogenous, but includes sweat glands that are very conductive when wet, and patches of dead skin that are typically very non-conductive. In addition, air bubbles sometimes are trapped between the gel and the skin. The air bubbles may cause local concentration of electric field around them. Occasionally, the gel pad may be partially lifted from the skin due to movements. Further, electric fields may concentrate on the gel pad's boundary that remains attached to the skin.

In any of the electrodes described herein, a resistive layer may be inserted between the control circuitry output (e.g., the output of the PCBA) and the gel body to evenly distribute the electrical current over the skin. This resistive layer may stop the current from concentrating on the sweat gland, and may reduce the field concentration around air bubbles and dried skin.

In some applications, the applicants have found that this resistive layer can be a low cost printed carbon film, or a plastic film impregnated with carbon particles. In other applications, a stainless steel mesh, which is non-conductive until there is a high enough voltage to break down the surface oxide layers, may be used. The temporarily high-resistance layer (e.g., the property of stainless steel's surface oxide) to cause the stainless steel to be non-conductive where there is a high resistance, such as air or dead skin, may protect the area disrupted by these artifacts. Thus, in some variations a stainless steel mesh may be preferably for both spreading the energy and protecting the user. In addition, the inherent electrical resistance of very fine stainless fibers may also create a resistive layer effect similar to carbon layers to prevent the local concentration of electrical current into sweat glands.

For example, FIG. 3 is a table (based on experimental data) summarizing the relationship between gel thickness and the distance of the nerve to the skin. In general for nerve targets that are closer to surface of the skin, a medium thickness gel (e.g., between about 0.5 mm and 1.2 mm) may be optimal. For longer distances, a thicker gel (e.g., greater than 1 mm, greater than 1.2 mm, greater than 1.4 mm, greater than 1.5 mm, greater than 1.7 mm, greater than 1.8 mm, greater than 2 mm, etc.) may be used.

In addition to the thickness, the location of the electrode gel pad may also be optimized. For example, in any of the variations described herein, the neuromodulator may be positioned behind the user's ear. In any of the apparatuses described herein that are configured to be placed behind the ear, an optimal configuration for the neuromodulation (e.g., electrode) behind the ear for inducing an energizing (e.g., 'energy') effect may be having a thickness of, e.g., between about 0.030 inch to 0.040 inch (e.g., between about 0.7 mm and 1 mm). Alternatively, in some variations, the gel thickness optimal for neuromodulation for inducing a relaxed neural effect from behind the user's neck may be between about 0.050 inches to about 0.060 inches in thickness (e.g., about between about 1.2 mm and about 1.5 mm). As shown in FIG. 3, thickens of the electrode (e.g., gel thickness) may depend on the distance to the target nerve.

The shape of the gel may also be configured and/or adapted (e.g., optimized) to the application. For example, FIG. 4A shows an example of an electrode, including a gel pad 407 that may be used behind the ear and is configured as an oval; in this example the oval is approximately 0.70 inch to 1.0 inch in the major axis, and 0.60 inch to 0.80 inch in the minor axis. This shape may be optimized to cover the bony protrusion behind the ear, which is a unique feature and an easy anatomical landmark for user to recognize for application of the electrode. FIG. 4B illustrates an example of a shape of an electrode (e.g., gel pad) for the return electrode.

Figure 4C:
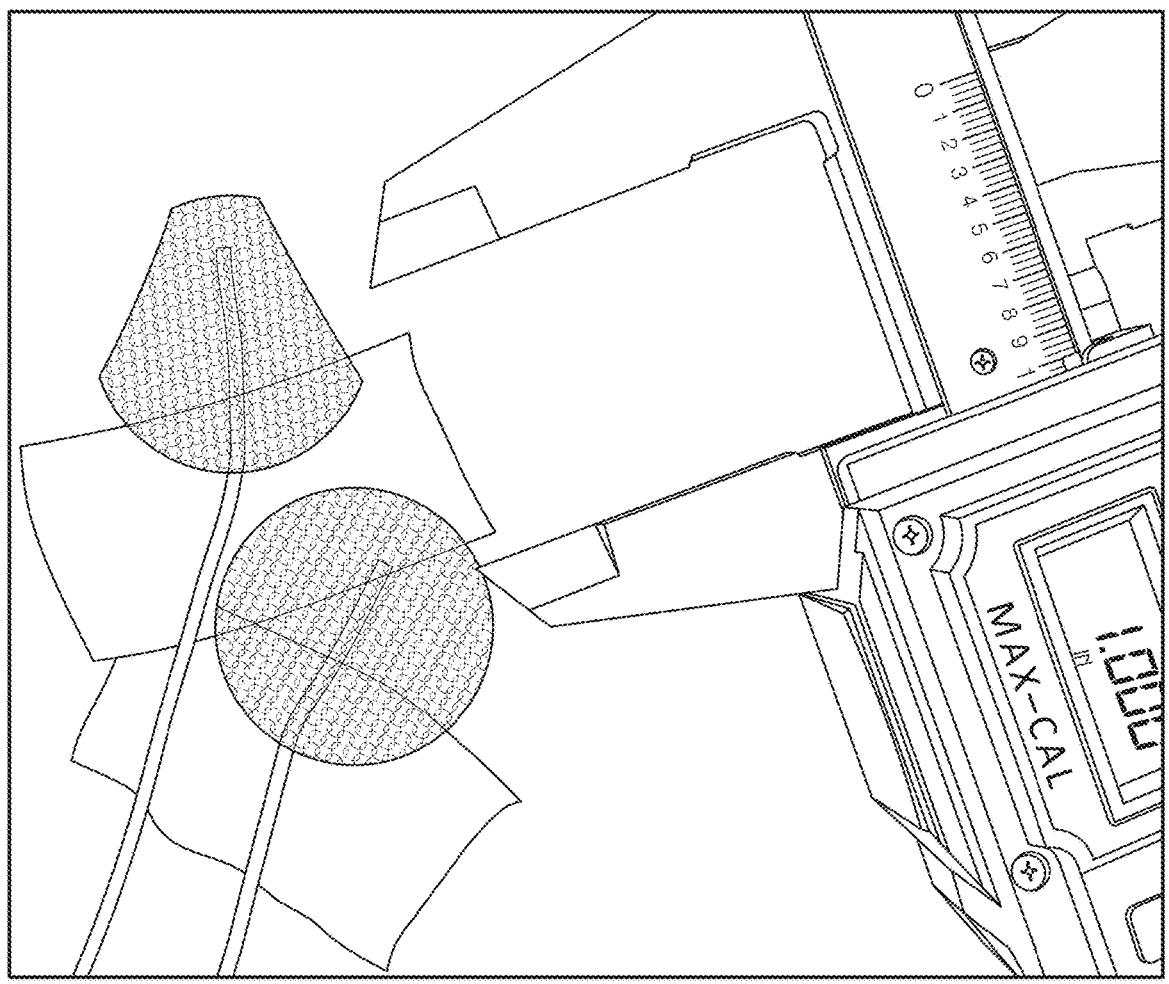
FIG. 4C shows examples of electrode shapes that may be used, including for use with a behind-the-ear (e.g., mastoid) electrode.

Alternatively, the mastoid (e.g., behind the ear) electrode, including the gel, may be wedge shaped, as shown in FIG. 4C. In this example, the wedge-shaped electrode (left) may including a slightly tapered shape that may conform well to the region behind the user's ear. The dimensions shown in all of these figures are examples only, and other dimensions may be used (e.g., +/−10%, 20%, 30%, 40%, 50%, 60%, 70%, 80%, 90%, etc.).

In some variations, the apparatus includes an electrode having a gel that is configured, including shaped, to fit on the back of the neck. For example, in some variations, the electrode is configured to target the nerve bundle behind the neck and is configured as a rectangle (e.g., FIG. 5A or 5B), e.g., with rounded corners 0.9 inch to 1.2 inch in width, and 0.8 inch to 1.1 inch in height. In this example, the top edge of this gel may be placed at the end of the hair line, where the neck has a natural fold. This anatomical landmark may allow the user to target the proper nerve bundle.

In any of these apparatuses, the reference electrode may provide a return path for the neural modulating electrical current. The shape of this electrode may affect the field distribution in the area between the two electrodes. The apparatuses described herein may be configured to have a uniform electric field at the target nerve bundle. For example, see FIGS. 4B and 5B. The apparatus may be positioned on the subject so that the nerve bundle targeted for modulation is positioned between the modulating electrode and the reference electrode. Therefore the distance between the two electrodes may be controlled. For example, FIG. 4B is one example of a reference electrode shaped to optimize electric field uniformity at the target neural bundle.

The applicants have found that it is surprisingly effective if the reference electrode is larger than the neural modulating electrode; this configuration may provide greater comfort of the user, minimizing the tingling sensation from the surface nerve that comes with the neuromodulation. For example, the reference electrode may be between about 110% and 200% the size of the modulating electrode (e.g., the electrode positioned in these examples, over the mastoid and/or on the neck); compare FIG. 5A (showing the modulating electrode for the neck, which may provide a "calming" neuromodulatory effect when a particular waveform is applied, as described herein) with FIG. 5B, showing its reference electrode.

Any of the apparatuses and methods described herein may be configured to form self-contained (e.g., limited-number-of-use) wearable neuromodulators that include printed conductive traces and/or woven conductive traces between control circuitry and the (e.g., gel) electrodes. The apparatuses described herein may be low-cost, and high-reliability. Any of these one-time use devices may achieve very low cost fabrication by utilizing automation in the assembly of the device; the use of printed layers and traces on a flexible substrate to conduct the neural-modulating waveforms generated at the control circuitry (e.g., printed circuit board) assembly to the skin contacting gel electrodes.

For example, printed traces may mate to the control circuitry (e.g., PCBA) via a compression force generated by dimples on the plastic housing forcing the printed traces against contact pads on the circuitry. For example, FIG. 6A shows one example. In FIG. 6A, the conductive traces consists of nanoparticles of silver that are dispersed in a binding medium, or alternately (and potentially lower cost), carbon particles may be used instead of silver particles. The traces may be laid down using a silkscreen process or an ink jet printing process. The ink may be formulated for flexibility so that it will not fracture when the substrate bends.

In FIG. 6A, the apparatus includes a housing or enclosure 601 that at least partially encloses the control circuitry 603 and may be connected to the flexible (e.g., woven) substrate 605. The housing/enclosure in this example includes two parts that are connected (e.g., snapped, via friction fit, welding, screw, etc.) so that the substrate 605 and conductive traces (which may be printed or otherwise formed on the substrate, or may be separate from the substrate) are held between the parts of the housing/enclosure so that it is both secured to the substrate and connected (via one or more connecting pads electrical communication with the control circuitry 609. In FIG. 6A, the first (e.g., upper) portion of the housing 601' includes a detent, dimple, projection, tab, etc. that applies force to maintain a connection between the conductive trace 611 and the circuitry 603. Thus, any of these apparatuses may include a compression contact between the conductive traces and the control circuit (e.g., PCBA).

Figure 6B:
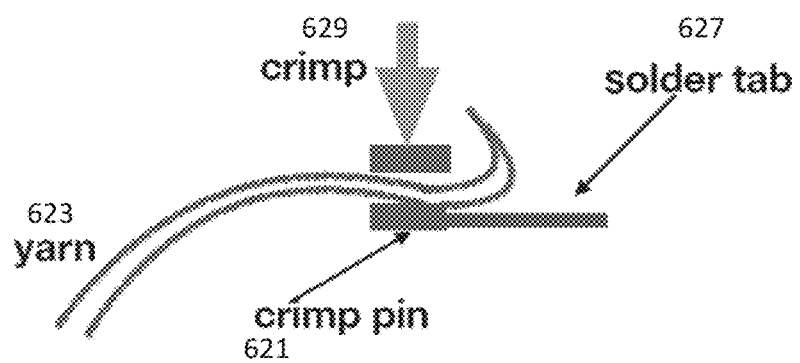
FIGS. 6B-6E illustrate examples of connections that between a conductor (e.g., conductive yarn) and an electrical contact (pad) of a control circuit, including within a protective frame or housing.
Figure 6C:
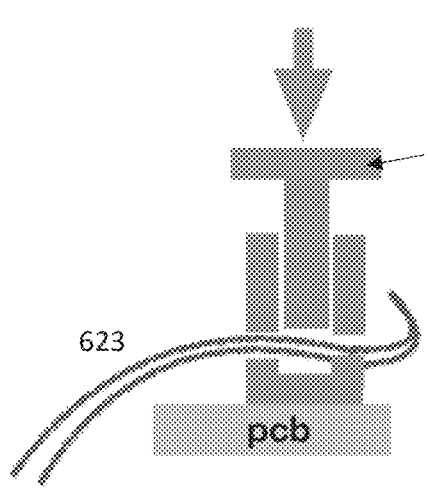
Figure 6D:
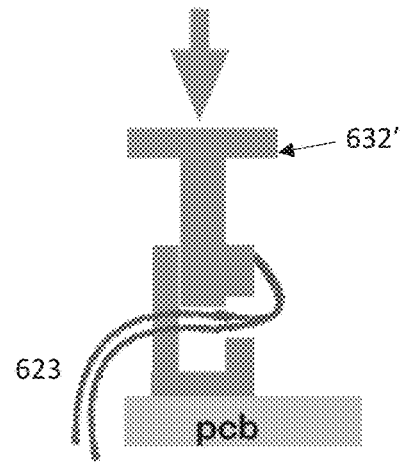
Figure 6E:
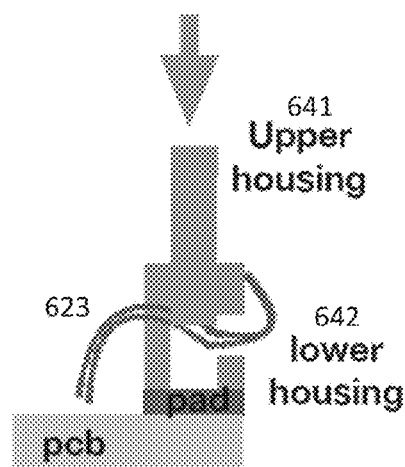

For example, FIGS. 6B-6D illustrate examples of methods for connecting a connector (e.g., a stainless steel interwoven yarn in this example) to control circuitry. In FIG. 6B a compression lock includes a crimp pin 621 that is used to crimp 629 the conductive yarn 623 to an electrical connector (e.g., solder tab 627) for a control circuit. FIGS. 6C-6D show examples in which a rivet 632 is used; in FIG. 6D the rivet is an open rivet 632'. In FIG. 6E, the connector may include an upper housing 641 and a lower housing 642 that can be locked together to secure the conductive yarn 623 to the conductive pad of the control circuit.

Figure 7:
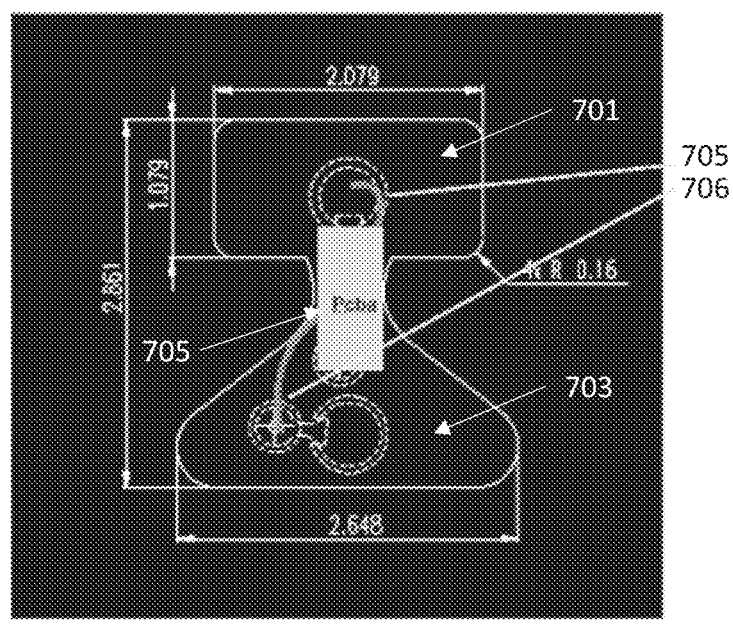
FIG. 7 is an example of a schematic of another example of a limited-number-of-use, wearable neuromodulator having a flexible (e.g., woven) substrate including control circuitry and electrodes.

FIG. 7 is another example of a limited-number-of-use neuromodulator that is configured to be worn behind the user's neck. In FIG. 7, the apparatus has a generally hourglass shape with a first 701 (e.g., upper) electrode (gel electrode) and a second 703 (e.g., lower, or return) electrode. The example shown in FIG. 7 includes exemplary dimensions. The control circuitry 707 in this example is connected to the electrodes by connecting wires 705, 706. The control circuitry may be enclosed in a housing (e.g., enclosure) as illustrated in FIG. 6A. The apparatus in FIG. 7 is also configured as a limited-number-of-use device and may be packaged in a sealed pack similar (e.g., limited-number-of-use packaging). The device is self-contained, and includes a battery (not shown in FIG. 7) and a miniature control circuitry (e.g., PCBA) that may contain the circuit necessary for neuromodulation. The device may be attached to the user (by the user) behind the neck, with the larger electrode placed on the shoulder region (e.g., C4-T3, e.g., C5-T1) and the small electrode on the back of the neck below the hair line (e.g., C1-C6, e.g. C2-C4).

Figures 8A, 8B:
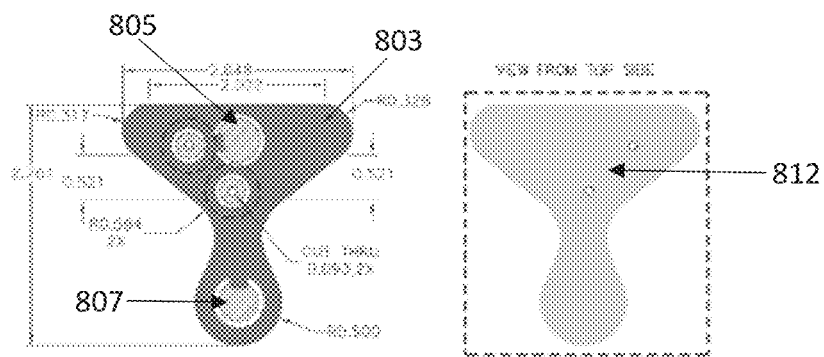
FIGS. 8A-8F illustrate different layers of the exemplary apparatus shown in FIG. 7, showing exemplary dimensions (which may be +/-5%, 10%, 15%, etc.).
Figures 8C, 8D, 8E, 8F:
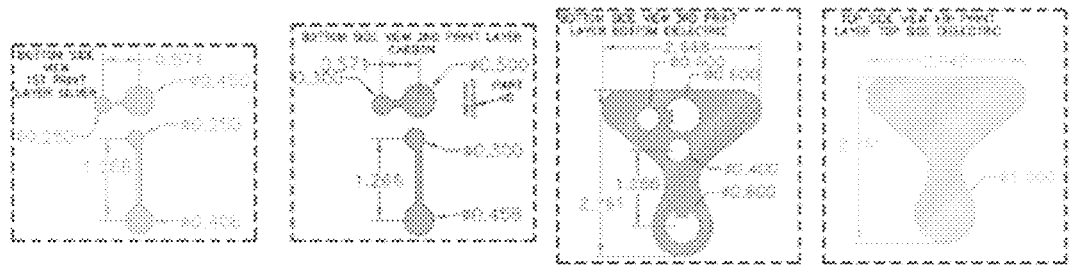

FIGS. 8A-8F show an example of a self-contained neck-worn apparatus, similar to that shown in FIG. 6, having different layers or region also showing exemplary dimensions. In FIG. 8A the substrate 803 (e.g., printed substrate) may include two or more contact regions 805, 807, e.g., formed by printed silver, for high conductivity, which may be covered by a $3^{rd}$ layer of carbon ink at the gel pads for controlling its electrical resistance and distributing electrical current evenly to the skin even in the presence of inhomogeneous structures. An additional printed layer (shown in FIG. 8B), may consist of an electrically insulating dielectric 812 so as to keep the traces from exposing to the user. FIG. 8C shows an example of a pattern of the conductive silver layer that may be used, while FIG. 8D shows an exemplary pattern of the carbon layer that may be used. FIG. 8E illustrates an exemplary pattern for the dielectric layer, while FIG. 8F is an example of the opposite side of the apparatus. In this example two rivets are shown to bring the electrical connection to the other side of the substrate. Alternatively, a folding technique such as disclosed above may be used to bring the conducting traces to the other side of the apparatus, where the control circuitry (e.g., PCBA) resides.

Figure 9:
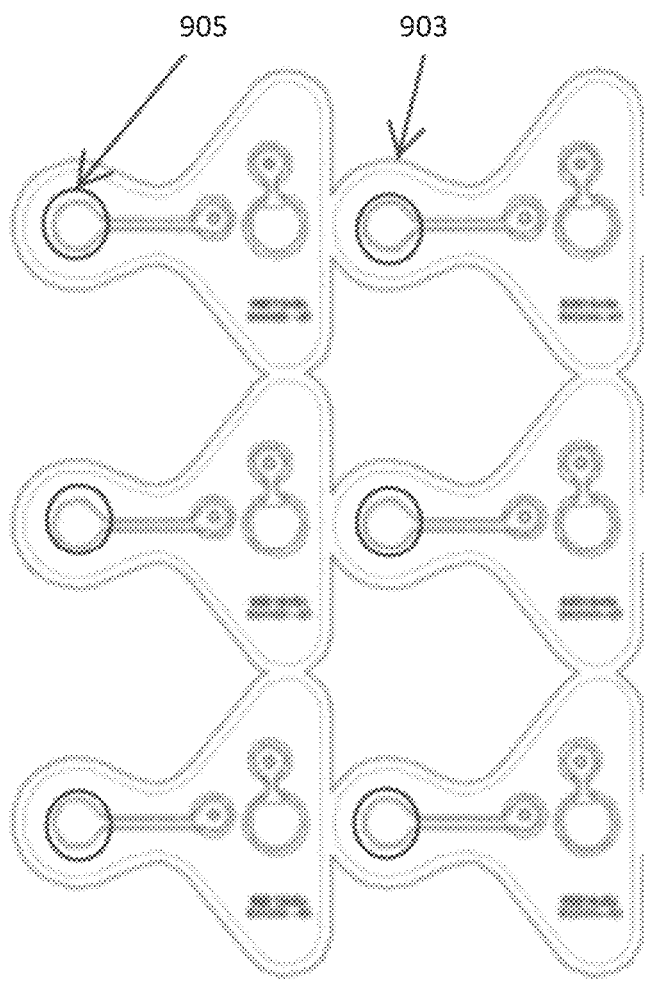
FIG. 9 illustrates one method of fabricating a limited-number-of-use, wearable neuromodulator having a flexible (e.g., woven) substrate including control circuitry and electrodes such as the one shown in FIG. 7.

The substrate and traces may be printed repeatedly on a large sheet then cut into individual units for substantial cost reductions, as illustrated in FIG. 9, showing a printed substrate that is repeated many times on a large sheet for mass reproduction. Printing many of these electrodes on a single sheet may allow them to be cut apart and separated later, after reliably screening/printing them. As discussed above, the substrate may be a paper, polymer or in some variations, a woven material (including braided, knitted, etc.), and the electrode 905 may be printed for each apparatus 903 in a batch manner.

Figure 10A:
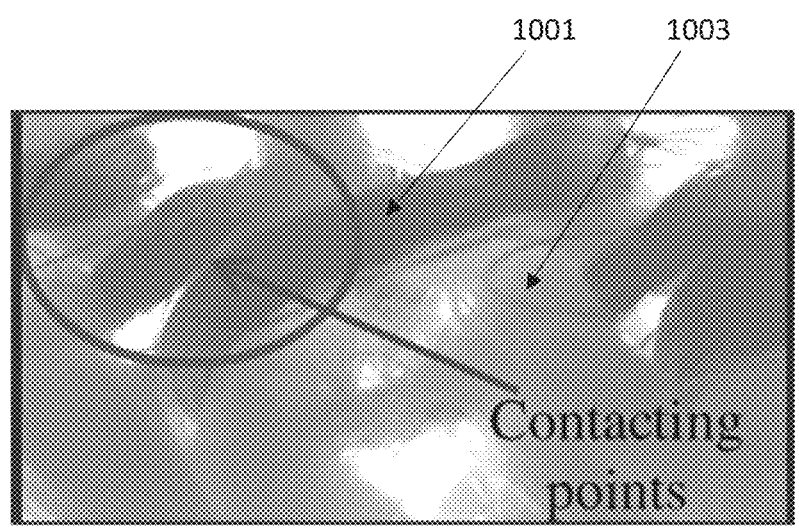
FIG. 10A is an example of a fibrous material including one or more conductive filament(s) that may be used as part of a limited-number-of-use, wearable neuromodulator having a flexible fibrous (e.g., woven) substrate.
Figure 10B:
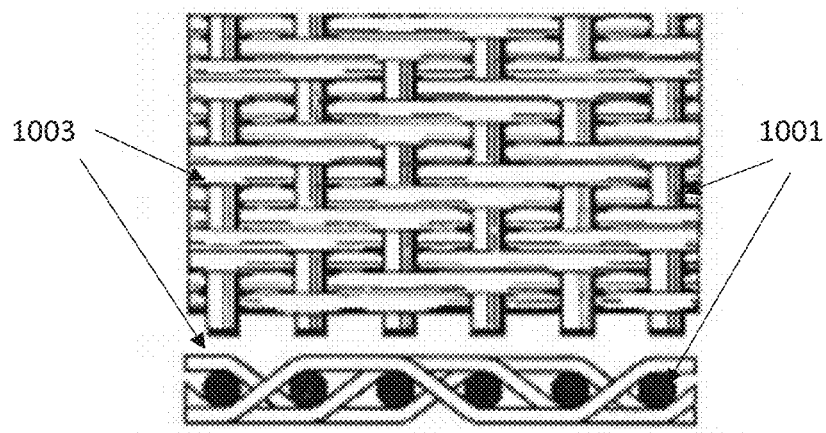
FIG. 10B is a schematic example of a woven material including both insulative strands and conductive strands, interwoven.

Any of the apparatuses described herein may use a mesh, such as a stainless steel mesh. In particular, a mesh, such as a stainless steel mesh, may be used to spread the current in the electrodes. For example, the Applicants have found that a stainless steel mesh made of very fine stainless steel fibers may be an excellent way to distribute current for neuromodulation when used as a current spreading layer placed between the control circuitry output and the electrode (e.g., gel layer) for skin coupling. For example, FIG. 10A illustrates one example of a stainless steel yarn 1001 that is interwoven with a polyester yarn 1003. The yarn 1003 in this example is electrically insulative. The stainless steel wire mesh may spread the electrical current uniformly throughout the gel, while the gel conforms to anatomical contours of the wearer for a better adhesion to the skin. FIG. 10B is a schematic illustration of a mesh formed of a non-conductive polymer (e.g., a polyester yarn) and stainless steel wires.

The gel electrode may be held in intimate contact with the user's skin, preventing stimulation of surface neurons that may irritate and/or distract the user. This intimate contact may be achieved when there is no rigid object around the electrode (such as connection snaps). Because of the stainless steel's mechanical properties, there is a memory in the mesh layer that may help it stay in a contact shape once pressed against the anatomy. The shape retention may help the gel pad to stay in place and make more intimate contact with the skin. In addition, the s steel is resistive to electrical current flow, so that the mesh, along with the gel pad, may spread the electrical currently evenly over the surface of the skin. The Applicants have found that a woven stainless mesh made of fine wires, e.g., 40 gauge or finer, inter-woven with a non-conducting fiber such as a polyester yarn may provide a combination of electrical resistance, retention of shape, and mechanical flexibility/softness, and the ability to spread the electrical current.

Figure 11:
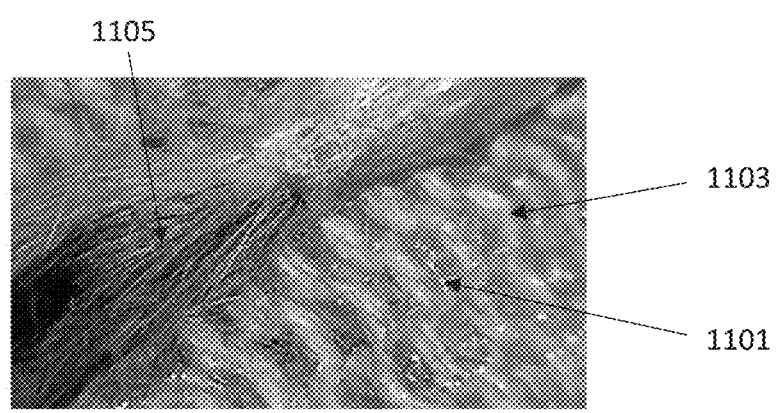
FIG. 11 is an example of a woven material having an interwoven conductive filaments making electrical contact with a bundle of conductive fibers (e.g., in a yarn or wire). In some variations the conductive filaments from the bundle may be continuous with the interwoven conductive filaments in the woven substrate.

FIG. 11 illustrates another example of a contact including an insulative yarn combined with stainless steel filament(s). In this example a bundle of stainless steel wires 1101 may be interwoven with a polyester yarn 1103. A polyurethane adhesive may be used to hold a stainless steel bundle 1105 in intimate contact with the mesh. Thus, FIG. 11 illustrates one method of forming an electrical contact with a stainless-steel interwoven weave (fabric), by making electrical contact using a pigtail of stainless steel fine wires adhered to the fabric (e.g., using a polyurethane).

Figure 12:
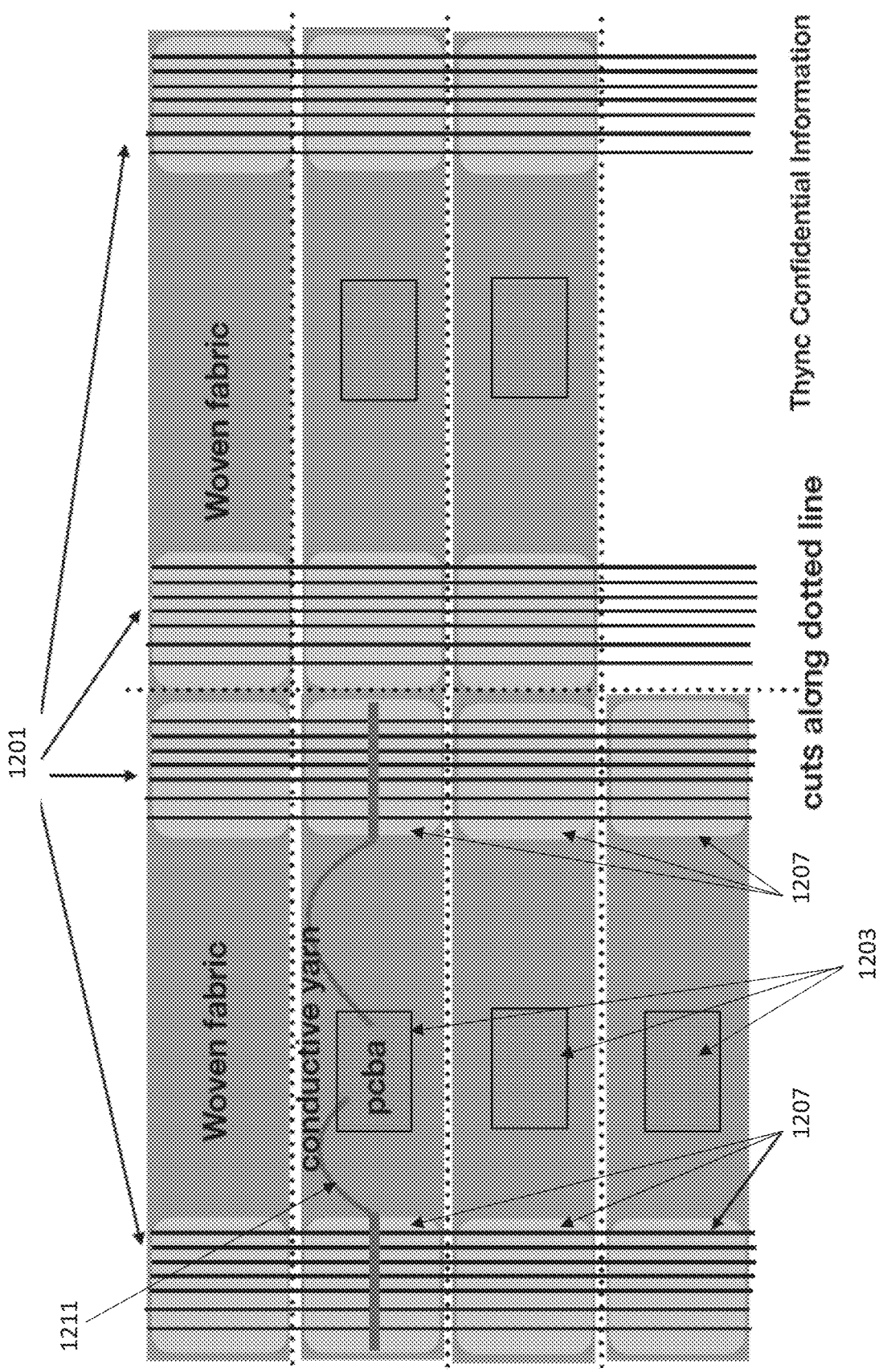
FIG. 12 illustrates an example of a method of manufacturing a limited-number-of-use, wearable neuromodulator having a flexible woven substrate.

For example, in some variations, a woven, insulating polymer fabric may be used as substrate, and may include conductive fibers (e.g., stainless steel fibers in the yarn interwoven at periodic locations). FIG. 12 illustrates an example of a method of manufacturing such apparatuses. In FIG. 12, the stainless steel mesh is interwoven with the fabric yarn in regions 1202 (periodically repeating regions). The non-electrode/nonconductive regions may be woven, but may lacking the conductive fibers (e.g., stainless steel fibers). Once or more control circuits 1203 may be attached to the woven substrate, either directly (e.g., using an adhesive) or through a housing (as shown in FIG. 6A, above). A gel (e.g., hydrogel) forming a gel pad 1207 as described herein may be electrically continuous with the regions of the mesh including the conductive fiber 1201. The electrodes, including the gel pads, may be connected via one or more wires, conductive traces, conducive yarns, etc. 1211 to the control electronics. The connectors may be stitched, embroidered or otherwise attached to the woven substrate. In some variations, the conductive trace is printed onto the woven substrate. These apparatuses may be fabricated as sheets (illustrated in FIG. 12) that may be cut apart, as shown in FIG. 12. Any of these apparatuses may also include a battery, e.g., conned to the control circuitry (including within or adjacent to any housing/enclosure).

Figure 13:
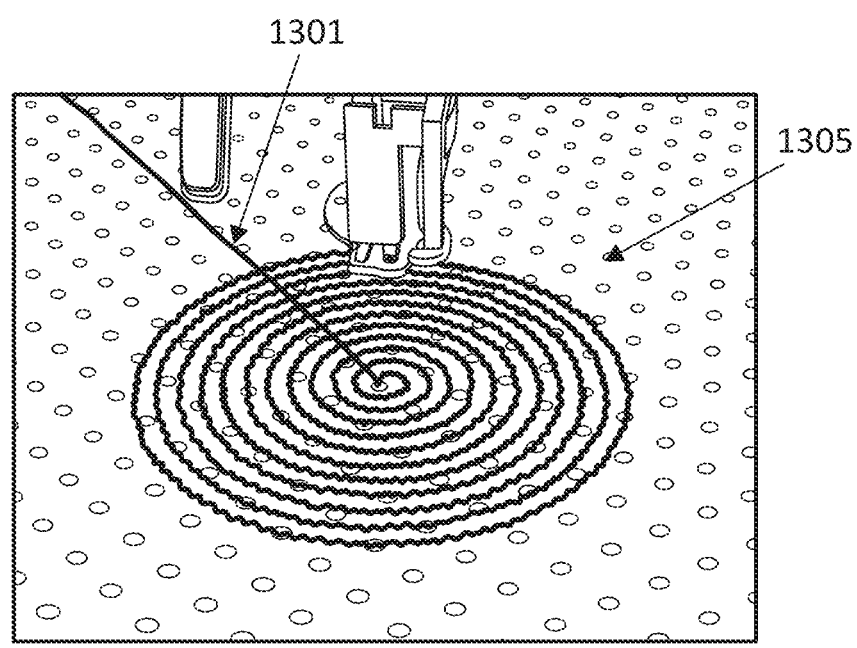
FIG. 13 illustrates one method of connecting a conductive yarn (e.g., including one or more stainless steel filaments) to a flexible, e.g., woven, substrate.

FIG. 13 illustrates another manufacturing technique, in which a stainless steel yarn 1301 is embroidered onto the gel pad area 1305 of the substrate to form a current-spreading mesh that is positioned under the gel pad.

FIG. 14 is another example of a substrate formed by a woven polymeric yarn or material 1401 into which fibers of conductive material (shown here as stainless wires) is woven. In FIG. 14, the polymeric fibers are woven to form the substrate and specific, conductive regions, e.g., underlying the electrode regions where the gel pads will be located, is interwoven with the conductive fibers (e.g., stainless steel fibers). For example, in FIG. 14, the stainless steel wire is, e.g., 100 gauge (e.g., 0.25 mil) wire and the polymer weave is formed of a polyester fiber (e.g., 0.1 mil). The number of stainless steel wires in the yarn may be approximately 30 (~30), and the yarn diameter may be approximately 14 mil. The square grid weave shown has a pattern of approximately 40 mil center to center.

FIGS. 15A-15B illustrates an example of a woven substrate including conductive fibers in a conductive yarn that may be used. FIG. 15A is a cross-sectional view of the first electrode region of an apparatus, showing a conductive gel having an approximately 30 mil thickness over a woven polyurethane substrate; underlying the conductive gel is a conductive yarn that if formed of a polyester material into which a stainless steel wire (e.g., 0.25 mil) is interwoven. FIG. 15B shows an enlarged view of the conductive yarn.

Figure 16:
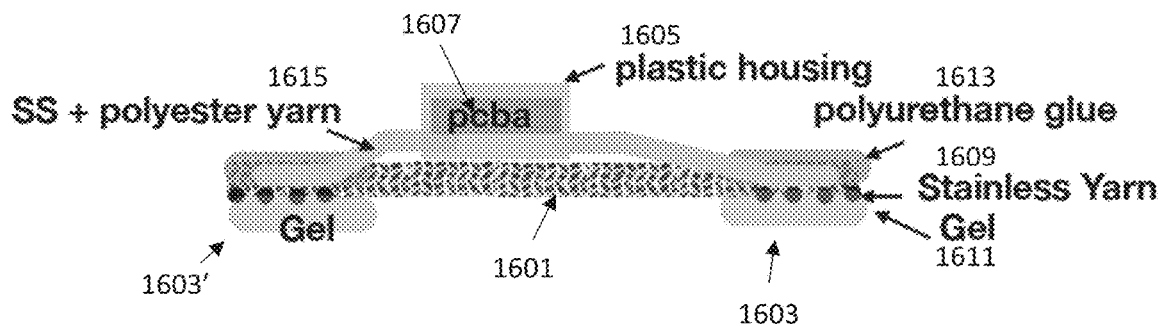
FIG. 16 is an example of a section through a limited-number-of-use, wearable neuromodulator having a flexible woven substrate showing a control circuit (circuitry) within a protective housing, electrical connections (e.g., via conductive yarns) to electrodes on the flexible substrate.

FIG. 16 is another example illustrating the use of the 3D woven substrate. In FIG. 16, the substrate is a woven material (e.g., polyester) to which the circuitry may be attached in a housing 1605 enclosing control circuitry (PCBA) 1607. In this example, the electrodes are formed by stainless steel-interwoven yarn 1609 that is stitched, woven or otherwise attached to the substrate and onto which a conductive gel pad 1611 is formed. The electrodes 1603, 1603' (formed by the conductive gel and underlying stainless steel yarn) may be electrically connected to the control circuitry within the housing by a conductor such as a stainless polyester yarn 1613, as shown in this example. In FIG. 16, the stainless polyester yarn conductor is attached via an adhesive (e.g., polyurethane glue) 1613.

Figure 17:
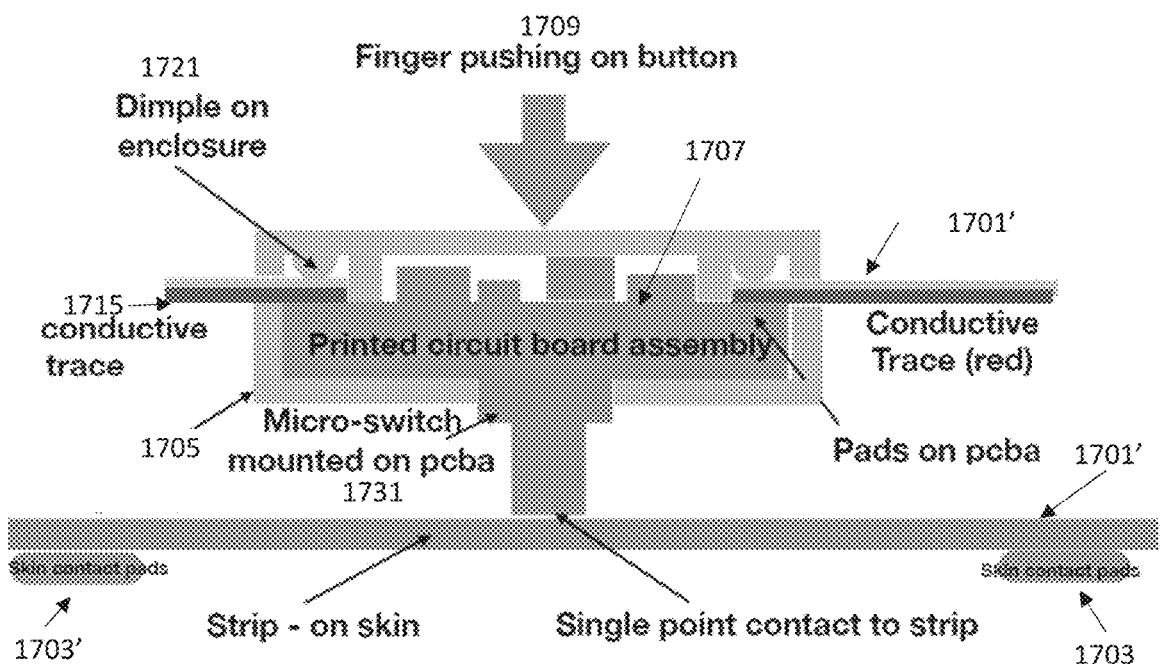
FIG. 17 schematically illustrates an example of a limited-number-of-use, wearable neuromodulator having a flexible woven substrate in which a housing enclosing the control circuit also forms a control (e.g., button) that may be actuated by the wearer/user.

FIG. 17 schematically illustrates an alternative variation in which the housing enclosing the control circuit also forms a control (e.g., button) that may be actuated by the wearer/user. In this example, the housing 1705 is configured to be pushed to operate a control (e.g., button) and also supports electrical contacts between the control circuitry 1707. The conductive trace/electrical connector 1715 is connected to the control circuitry by a mechanical securement (shown as a dimple in this example) 1721 that also secures the housing to an extension (e.g., a 'finger') of the woven substrate 1701'. In this example, the skin-contacting side of the substrate may make a single point of contact with the micro-switch 1731 and the woven substrate 1701. The skin-contacting electrodes 1703, 1703' may be formed as described herein.

Figure 18:
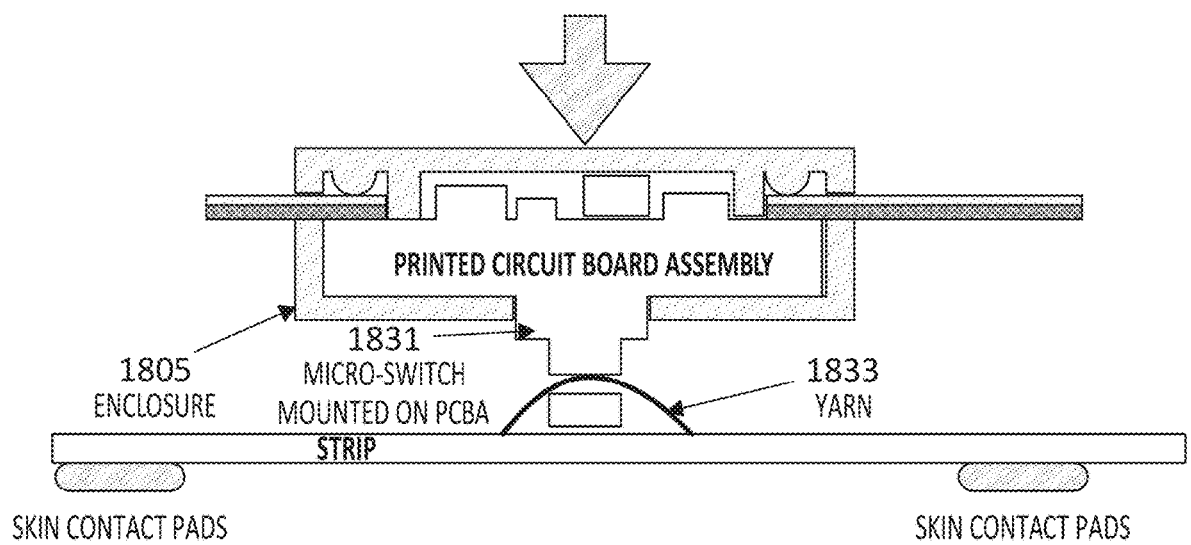
FIG. 18 is a schematic illustration of another example of a limited-number-of-use, wearable neuromodulator having a flexible woven substrate in which the housing holding the control circuit(s) is sewn onto the substrate.
Figure 19:
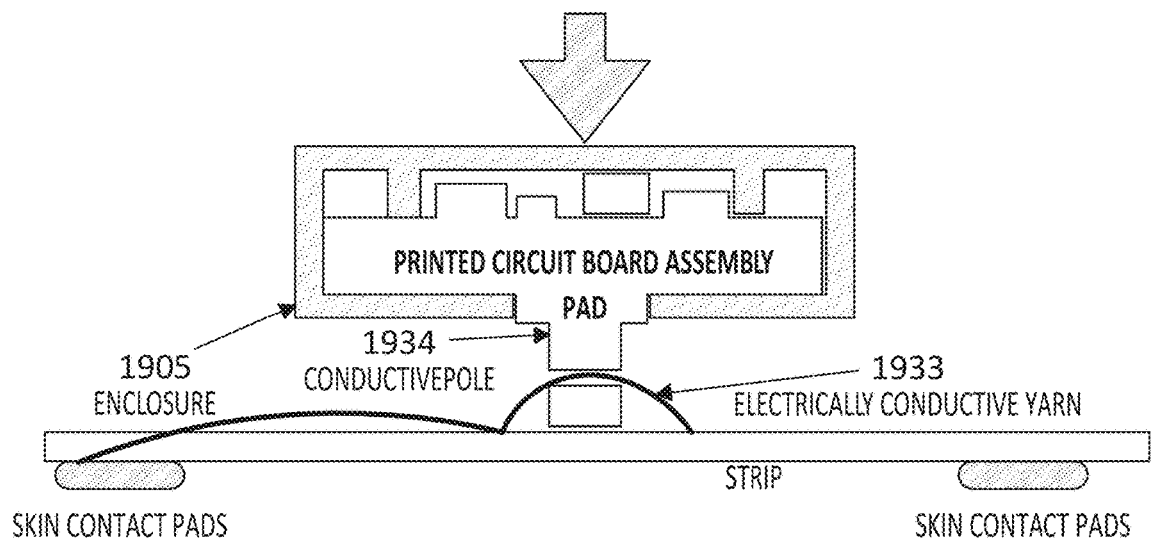
FIG. 19 is a schematic illustration of another example of a limited-number-of-use, wearable neuromodulator having a flexible woven substrate in which the housing holding the control circuit(s) is sewn onto the substrate via an electrically conductive yarn or filament that can make electrical connection to one or more electrode(s).

FIGS. 18 and 19 illustrate alternative examples in which the housing is also configured as a button connected to the control circuit. In FIG. 18, the button is a micro-switch 1831 that is mounted to the control circuit(s) within the housing/enclosure and the housing is sewn or stitched to the substrate (e.g., woven substrate) by a fiber (e.g., yarn 1833). In FIG. 19, the mount 1934 for the housing (connecting the housing to the substrate) may also include one or more conductive contacts and may make electrical contact between the electrode(s) and the control circuit(s) within the housing, e.g., via an electrically conductive yarn 1933.

Figure 20:
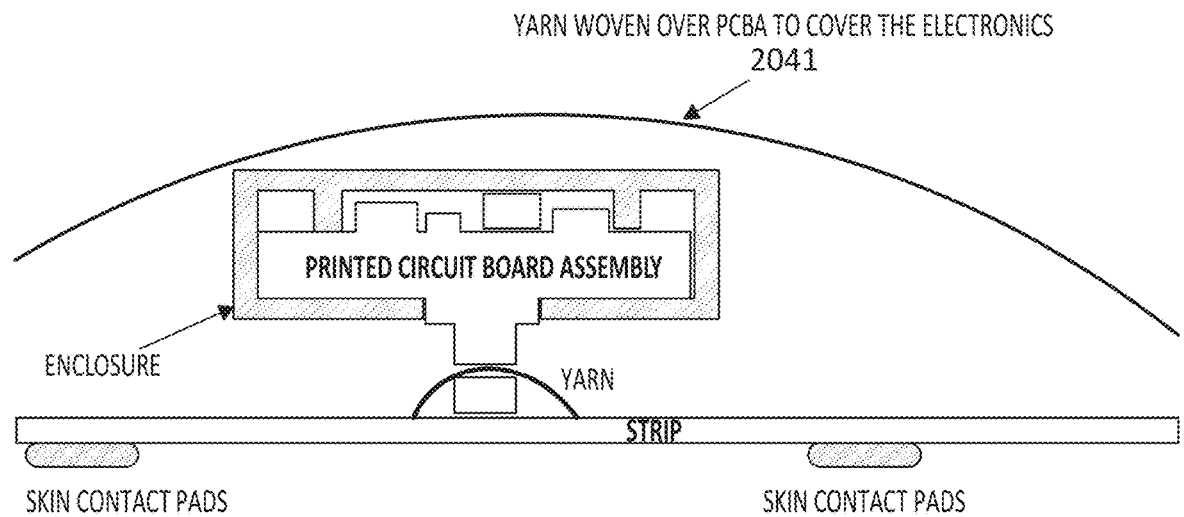
FIG. 20 is a schematic illustration of another example of a limited-number-of-use, wearable neuromodulator having a flexible substrate including a cover that may be a separate and/or different fabric material (shown as a woven material in this example).
Figure 21:
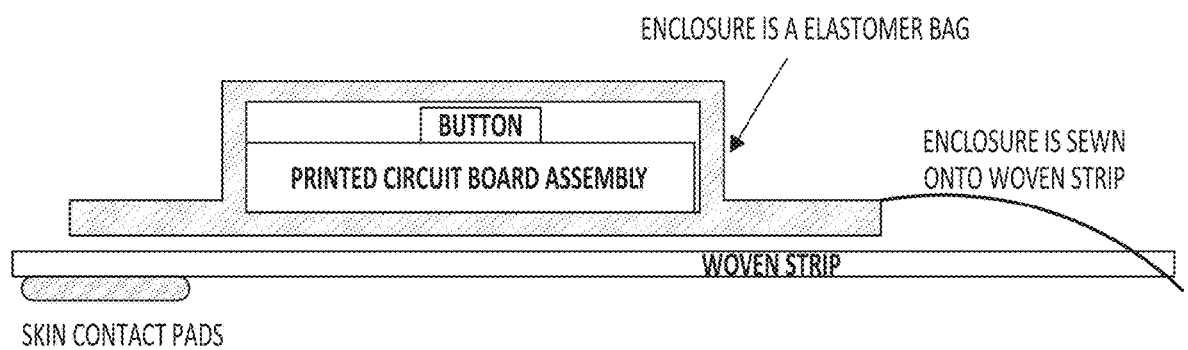
FIG. 21 is a schematic illustration of another example of a limited-number-of-use, wearable neuromodulator having a flexible woven substrate including an elastomeric fabric cover (elastomer bag).

Any of the apparatuses described herein, with or without a woven substrate, may include a cover or wrap (housing) enclosing all or part of the power source and control circuitry; this cover may be formed of a different material than the substrate, and in particular may be a polymeric fabric. FIGS. 20 and 21 schematically illustrate alternative embodiments. In FIG. 20, in addition to the underlying substrate, a fabric material 2041 may be positioned over the housing for the control circuitry (or just over the control circuitry if a housing is not included). This may cover and protect tee electronics. Although any variation of the attachment of the control circuitry to the substrate may be used, a variation similar to that shown in FIG. 18 is shown in this example. In FIG. 20 the cover fabric may be a woven material (including the same or a different material as the substrate). For example, in FIG. 21, the cover is not a woven material, but may be a polymeric material (e.g., a plastic) such as a plastic bag; the polymeric cover may be part of the enclosure/housing for the control circuitry, as shown. The enclosure may therefore by sewn or otherwise attached (e.g., adhesively attached) to the woven substrate.

Figure 22:
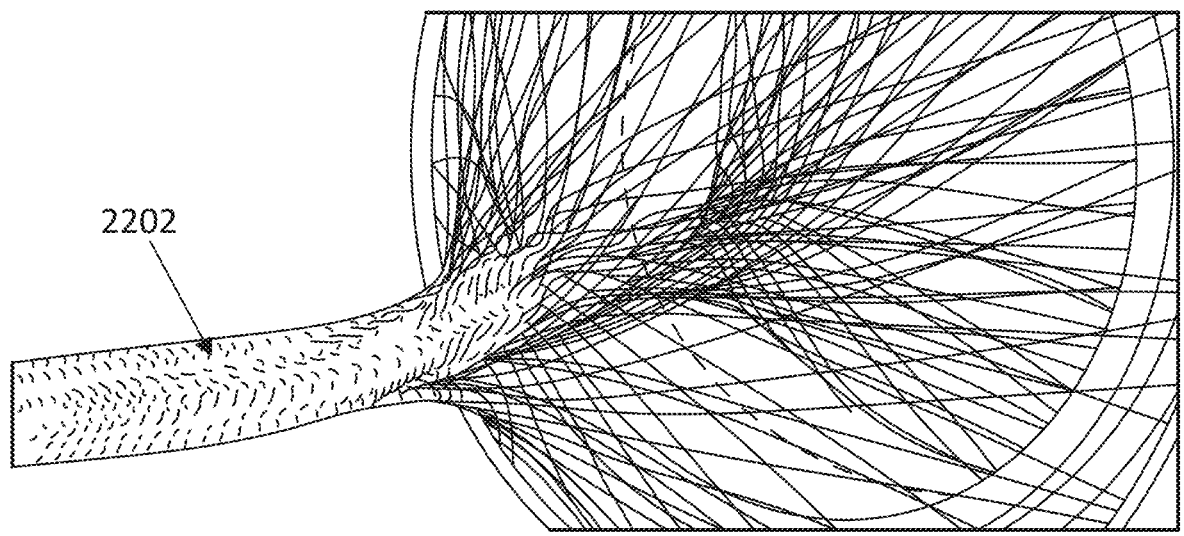
FIG. 22 illustrates an example of a woven stainless-steel that is both the connector to the control circuitry and also extends radially outward to form a conductive mesh within the electrode underneath a conductive gel pad.

In any of the variations described herein, the conductive yarn, may include a plurality of conductive strands or fibers (e.g., of stainless steel). In some variations, these strands may be woven into the mesh or weave of the electrode(s) of the apparatus by forming a pig-tail like connection in which the various conductive fibers radiate outward. In some variations, the conductive fibers may radiate outward from the conductive connector, which may be yarn including the stainless steel fibers that may connect the electrode to the control circuitry. For example, FIG. 22 illustrates an example of a woven stainless-steel yarn 2202 that is both the connector to the control circuitry (not shown) and that extends radially outward to form a conductive mesh within the electrode underneath a conductive gel pad (not shown).

Figure 23:
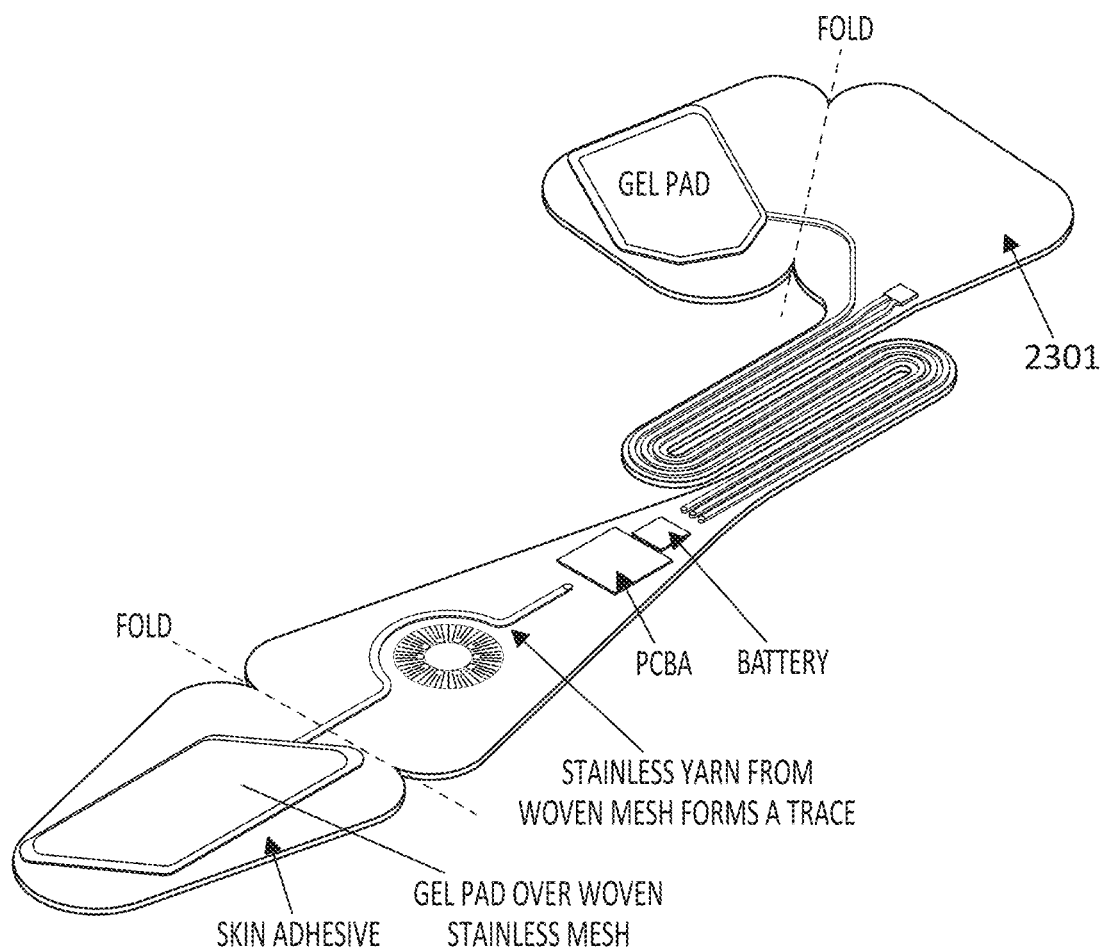
FIG. 23 is another example of a limited-number-of-use, wearable neuromodulator having a flexible woven substrate.

For example, FIG. 23 illustrates another example of a neuromodulator apparatus that is configured for limited-number-of-use and includes a woven substrate (this example is configured to be worn behind a user's ear, in the mastoid region), in which a stainless steel mesh is used to form part of the electrode(s).

Figure 24A:
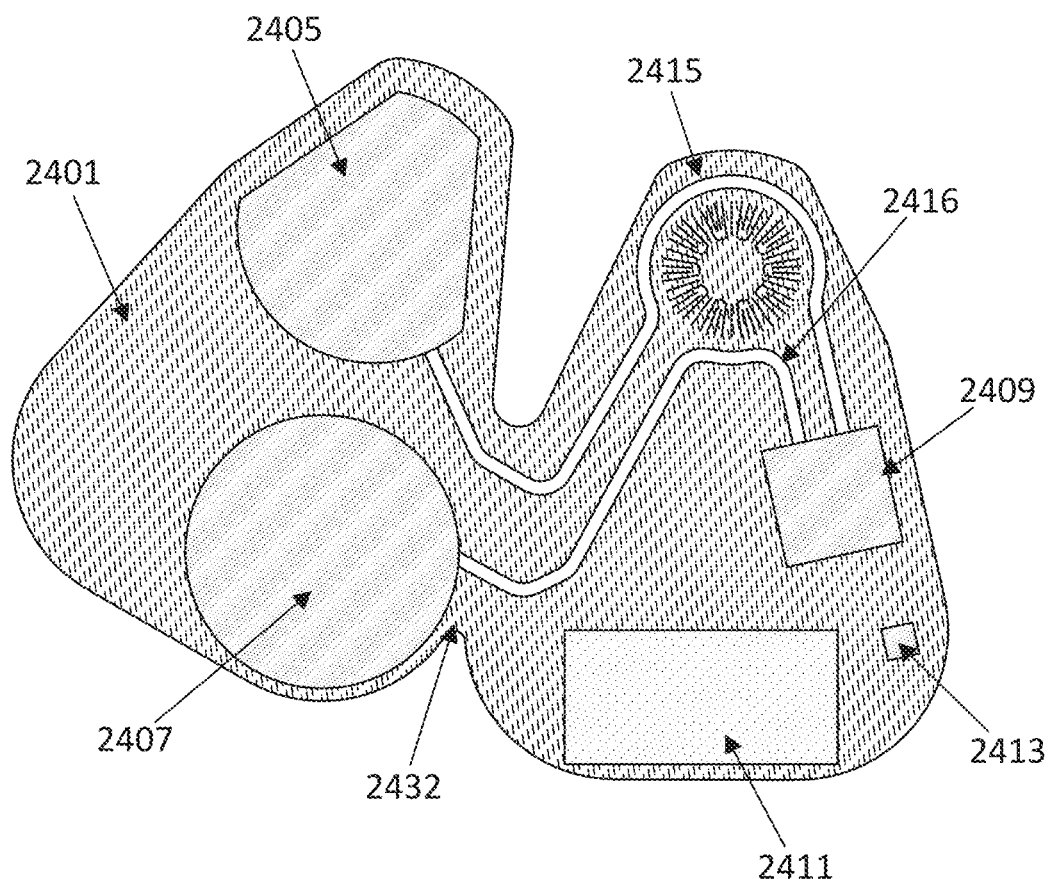
FIG. 24A is another example of a limited-number-of-use, wearable neuromodulator having a flexible woven substrate configured to be worn behind the user's ear.

FIG. 24A is another example, showing a different form factor, also configured to be worn behind the user's ear. In both examples, the control circuitry, battery, control input (e.g., button), electrical connectors (e.g., conductive traces, wires, woven fibers, etc.) and electrodes) are all attached to the woven substrate 2401. The substrate 2301, 2401 may be folded over to make the connection to the subject. However, in FIG. 24A, the first and second electrodes (anode and cathode) are nearly adjacent to each other, so that the center of each conductive gel pad of the electrode is only separated by each other by less than about 3 inches (e.g., less than 2 inches, e.g., less than 1.5 inches, etc.). In FIG. 24A, the first and second electrodes are separated from each other (on center) by about 1.25 inches.

Thus, a limited-number-of-use neuromodulator device configured to be worn on user's skin over the mastoid region, may include a flexible substrate 2401 (which may be any flexible materials suitable for printed electronics such as Polyethylene terephthalate (PET), polyimides, polyurethanes, polyethylene, polypropylene, etc.). The device may include a first electrode 2405 having a tapered profile (e.g., approximately triangular, also in FIG. 4C, on the left, which may also be referred to as 'wedge-shaped') on the flexible substrate. This first electrode may be at the narrow vertex of the device. As already mentioned, the first electrode may include a first conductive gel pad (visible, outward-facing portion). Although the first electrode is approximately triangular- or wedge-shaped, it has rounded edges; in addition, the long sides of the profile of the electrode (e.g., the gel pad) may be bent or curved. In FIG. 24A, the bottom of the electrode is rounded. This shape may help distribute current and prevent irritation.

The device shown in FIG. 24A also includes a second electrode 2407 on the flexible substrate. The second electrode typically includes a second conductive gel pad. As mentioned, the center of the first conductive gel pad is separated from a center of the second conductive gel pad by less than, e.g., two inches. The second electrode (e.g., the gel pad) may have a different shape than the first electrode (e.g., round, rounded, oval, etc.).

The exemplary device shown in FIG. 24A also includes a control circuit 2409 mounted on the flexible substrate and a power source 2411 in electrical communication with the control circuit on the flexible substrate. In general, the control circuit is configured to deliver a constant-current waveform between the first and second electrodes. The control circuit may include hardware, software of firmware that is configured (e.g., pre-programed, hardwired, etc.) to deliver an "energy" waveform that is designed to evoke a feeling of energy in the user receiving the waveform from the device, when worn behind the ear.

Figure 24B:
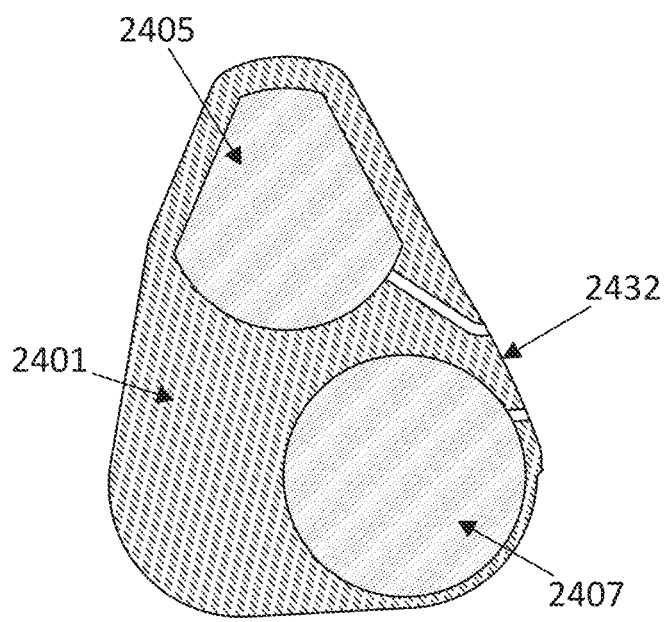
FIG. 24B shows the device of FIG. 24A in the fully-assembled configuration, folded over itself.

The substrate in FIG. 24A may be any appropriate flexible substrate, including (but not limited to) fibrous, e.g., woven, substrates. In FIG. 24A, most or all of the elements (e.g., electrodes, control circuit, battery, electrical connection (shown as electrical traces 2415, 2416) are on a first side of the substrate, and the substrate is folded back on itself, so that the electrodes face the user (when worn) and the control circuitry and power source face away from the subject. The connectors (e.g., electrical traces) extend along the first side, over the hinge region 2432, and along the second side to the circuitry. FIG. 24B shows the user-contacting side of the folded-over device. The device may be fixed (e.g., adhesively, stitched, welded, etc.) in this folded over configuration.

Although FIG. 24A-24B shows a specific embodiment, any of the features shown herein may be used or adapted into any of the other embodiments described herein, and similarly, any of the alternative features described herein may be included as part of a variations such as shown in FIGS. 24A-24B. For example, the control circuit(s) may be housed in a housing (or enclosure) enclosing the control circuit and coupling the control circuit to the substrate.

As mentioned, any appropriate substrate 2401 may be used, including a fibrous substrate (e.g., a woven substrate). For example, the substrate may be a woven insulating material.

In some variations, the apparatus may include a control input 2409 that is electrically coupled to the control circuit and configured to control one or more of: power (e.g., on/off and/or pause/resume) and intensity (e.g., amplitude of the applied voltage) of the device. Alternatively, in any of these variations the apparatus may not include a control input, and may instead autonomously function without any control input. Thus, in some variations the control circuitry may automatically apply a waveform after power is applied to the control circuitry, e.g., upon removal from the packaging and withdrawal of any circuit interrupt. In some variations the apparatus may determine that or when the electrodes are in contact with skin, e.g., based on impedance between the electrodes, and may automatically apply the waveform only when skin contact is confirmed.

As shown in FIGS. 24A and 24B, the outer surface area of the second electrode may be larger than an outer surface area of the first electrode.

Any of the devices described herein may include a first plurality of conductive filaments attached to the woven substrate. The plurality of conductive filaments may be configured to distribute current within the first conductive gel pad. The plurality of conductive filaments may be stainless steel filaments having a diameter, e.g., of 40 gauge or finer.

In FIG. 24A-24B, as in any of these examples, the thickness of the conductive gel pads may be configured to optimize treatment (see, e.g., FIG. 3, above). For example, the first conductive gel pad and the second conductive gel pad may each have a thickness of between about 0.030 inch to 0.040 inch in FIG. 24A; this thickness may be specific to the use of the device for stimulation behind the user's ear (e.g., over the mastoid region).

In FIG. 24A, the substrate configured to be folded over itself so that the first and second electrodes are on a first side and the control circuit is on a second side, as shown in FIG. 24B. Thus, the final profile of the fully-assembled device is a tapered, e.g., wedge-shaped profile, as shown. This shape may fit well behind the user's ear, over the mastoid.

Any of these device may also include one or more connectors, e.g., a first connector electrically coupling the first electrode to the control circuit and a second connector electrically coupling the second electrode to the control circuit. The connector may be any appropriate electrical connector (e.g., a conductive yarn, a wire, a printed electrical trace, etc.). In FIG. 24A-24B the connector is an electrical trace that is printed or otherwise adhered to the substrate. The first and second conductor are shown each extending along a first side of the device, over an edge of the device (at the fold region 2432) and along a second side of the device to connect to the control circuit.

The control circuitry in any of these devices, including the variation shown in FIGS. 24A-24B, may be configured to provide a waveform that has a therapeutic and/or neuromodulator effect. For example, the control circuit may be configured to provide an amplitude-modulated carrier waveform having a trapezoidal envelope, wherein the carrier waveform comprises a pair of repeating pulses. In FIG. 24, the waveform may be adapted to provide an "energy" waveform (e.g., to induce an energized mental state) similar to the waveform parameters shown in FIG. 30A and described in detail below.

In FIGS. 24A-24B, as in any of the apparatuses described herein, the control circuitry and power source (e.g., battery) may be adapted to be a limited-number-of-use device, having a very high electrical efficiency (e.g., greater than 75% efficient, greater than 80% efficient, greater than 85% efficient, greater than 90% efficient, etc.) when converting the energy from the power source into electrical output delivered to the user through the conductive gel pads.

For example, in FIG. 24A (or any of the apparatuses described herein), the power source may comprise a battery having less than a 50 milliamp hour capacity (e.g., may be one or more alkaline batteries in series having an instantaneous current output of less than 20 milliamps), and a maximum voltage output for the device is between 10 V and 30 V, yet may provide electrical stimulation to the user for more than 15 minutes (more than 20 minutes, more than 25 minutes, etc.) before being removed and recycled/destroyed.

For example, a limited-number-of-use neuromodulator device, similar to the one shown in FIGS. 24A-24B, may be configured to be worn on user's skin over the mastoid region and may include: a flexible substrate having a fabric cover in which the control circuitry and battery are held between the substrate and the cover; a first electrode on the flexible substrate on the first side, the first electrode comprising a first conductive gel pad; a second electrode on the flexible substrate on the second side, the second electrode comprising a second conductive gel pad, wherein a center of the first conductive gel pad is separated from a center of the second conductive gel pad by less than 1.5 inches. The electrodes may be concentrically arranged as described below. The control circuit may be retained above the flexible substrate on the second side of the substrate without being attached to the substrate, so that it may move slightly as the apparatus is flexed. Similarly, the power source in communication with the control circuit may be positioned above the flexible substrate. The control circuit is configured to deliver a constant-current waveform between the first and second electrodes.

Figure 25A:
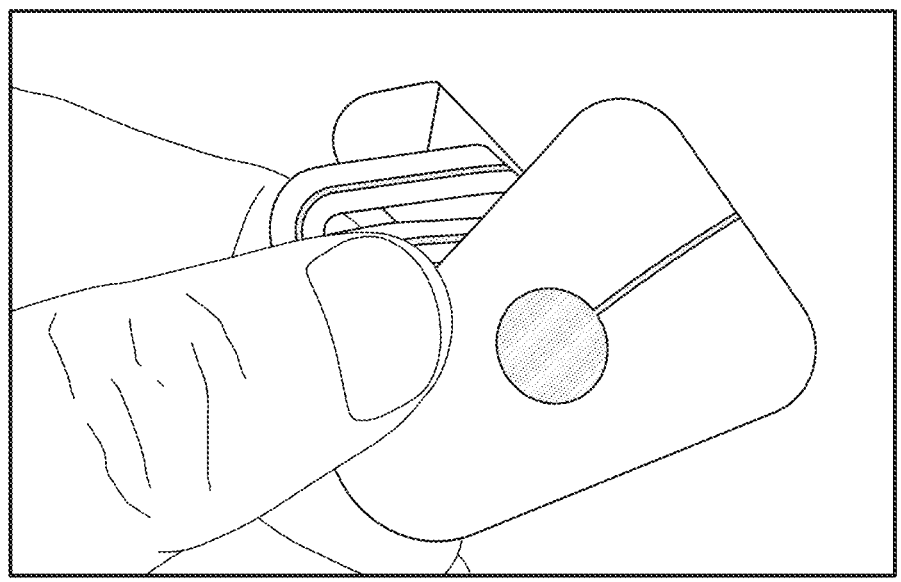
FIGS. 25A and 25B illustrate an example of a flexible fibrous substrate having a shape memory wherein the flexible fibrous substrate is configured to return to a set shape after being folded or bent.
Figure 25B:
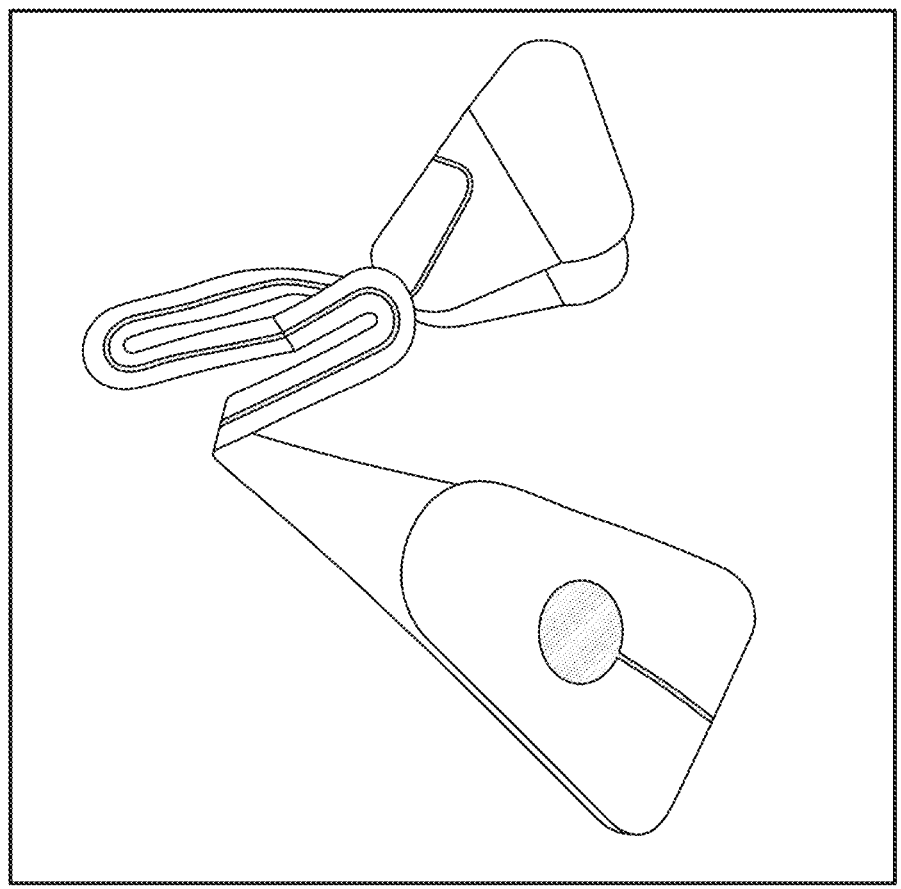

In general, the substrate, including in some variations a fibrous (e.g., woven) substrate, may allow the device to resume a preset shape even if deformed (e.g., during handling, manufacture and/or packaging). For example, a three-dimensional (3D) woven stainless yarn may help form the electrode and may provide a spring force for the skin contact and may help the electrode conform better around areas having a bony structure under the skin. This may also aid in the ability of the apparatus to bounce back into functional shape after removing from a small packaging. FIGS. 25A-25B illustrate an example of an apparatus having a paper or polymeric substrate that is not woven, showing bending/deformation of the substrate. In this example, the substrate is a fibrous paper material (e.g., polyethylene terephthalate, PET) formed of filaments with a soft filler between the fibers. This material (commercially referred to as Tyvek) may be used in addition to or instead of the woven substrates described herein, and may include many of the shape-memory properties of the woven materials. For example, in FIG. 25A, the apparatus formed of the fibrous paper substrate is shown able to return to the original shape after being squeezed into a small package.

Waveforms

In general, the neuromodulation apparatuses described herein may typically generate high voltage (e.g., approximately 50 volts), constant current (e.g., of up to 25 milliamp) electrical pulses at between 100 and 16.0 KHz frequency. In general the charge per phase of the waveform may be between about 0.1 to 10 μC per phase The circuit must may have a highly efficient to minimize the size of the battery, and may be extremely low-cost to manufacture, and in particular, may consist of a small number of components to keep the product light in weight and small. Delivering a constant current is desirable given the variability in skin and tissue properties between individuals and between two use cases for the same individual. However, constant voltage circuits with variable current can also be used in part of the waveform.

Figure 26:
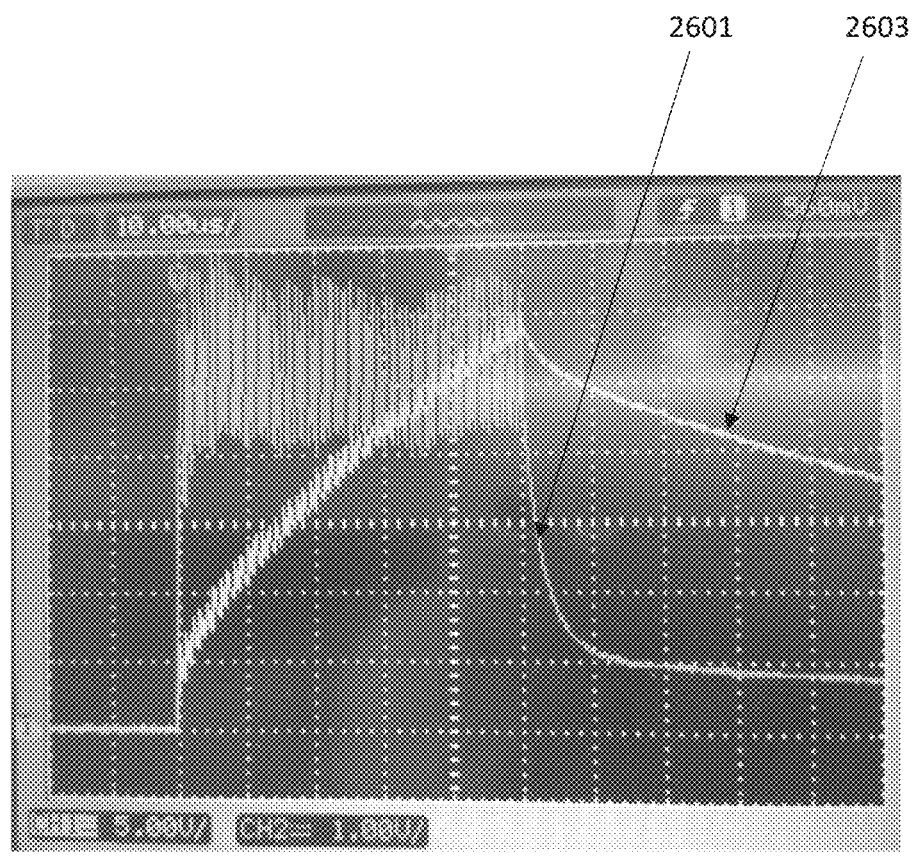
FIG. 26 illustrates one example of the relationship between current and voltage during the application of energy by a limited-number-of-use, wearable neuromodulator as described herein.

These requirements may be achieved by the use of a highly efficient circuit that utilizes knowledge of the skin's equivalent electrical circuit and the relationship between the constant current electrical pulses and the output voltage. FIG. 26 illustrates one example of the relationship between current 2601 and voltage 2603 during the on time of the pulse. A traditional waveform generator with constant current capability may use a step-up power supply to bring the supply voltage from the battery level (e.g., typically 3 volts) up to the 50 volts applied by using a step-up converter; it may then create a constant-current source from the high voltage power supply, and then put in a switching circuit to generate the pulses. The disadvantage of the traditional design is that circuit is complex and expensive, and it takes up a lot of room. The traditional design also keeps the high voltage all the time, even when it is not needed. The power efficiency is therefore relatively poor.

Described herein are control circuitry for applying neuromodulation (neuro-stimulation) waveforms, which may be referred to as ensemble waveforms because they may apply a set of electrical parameters between the electrodes of any of the devices described herein that are specifically configured to result in a neuromodulator effect and/or therapeutic effect desired. For example, in some variations the ensemble waveform(s) to be applied is/are programmed or encoded into the control circuitry as software, firmware and/or hardware. The ensemble waveform(s) may be configured to induce a cognitive effect in the subject, such as an energizing effect, a calming response, an improvement in memory, etc. In some variations, the ensemble waveform(s) may be configured to induce an energizing response in the user.

The control circuit(s) described here may be configured to provide a waveform having a constant current pulse. Given the electrical model of the skin at a particular frequency, this constant current pulse may translate into a voltage ramp of a specific shape. This transformation may map from current pulse to voltage ramp and may be computed off-line, and then stored in the low cost micro-controller chip in the limited-number-of-use device.

This information may then be used in a pulse width modulation boost converter (or alternately a pulse frequency boost converter) in which short bursts of energy are fed into a small inductor. The inductor may provide a high voltage burst with the same energy as the input energy pulse.

In addition, the waveform may also be transformed off line to convert a desired voltage ramp into a sequence of input pulses of various durations for the kick-up inductor. This mapped sequence of pulse duration may then be stored in the low cost microcontroller, and then applied to the inductor through a low cost switching transistor, so that the inductor will "kick up" the voltage to achieve a specific ramp pattern as desired.

A combination of inductor and capacitor may be used to smooth out the voltage at the output to get rid of the spikes coming from the pulse nature of the kick-up pulses.

The apparatuses may also include feedback control of the current pulse output. For example, due to the variable electrode contact resistance, or the skin impedance reacting to modulation and changing over time during a neuromodulation session, the neural modulating current may fluctuate. This fluctuation is undesirable. An electrical current sensor, measuring the voltage drop on a resistor connected in series with the output, may provide a monitor of the electrical current for a very low cost. This same resistor, along with voltage measurement of the output, using Analog to Digital converters built into the micro-controller, may also allow the monitoring of the impedance seen by the electrode pads.

Any of these apparatuses may also be configured for detection that the electrode pads are on skin, and ready for applying neuromodulation. For example, when the impedance is low, indicating the gel pads are on the user, the apparatus may detect this and may be configured to allow the neuromodulation to start. To probe the impedance across the electrode pads, a small pulse output may be generated by the microcontroller to apply to the electrodes for this purpose.

Figure 27A:
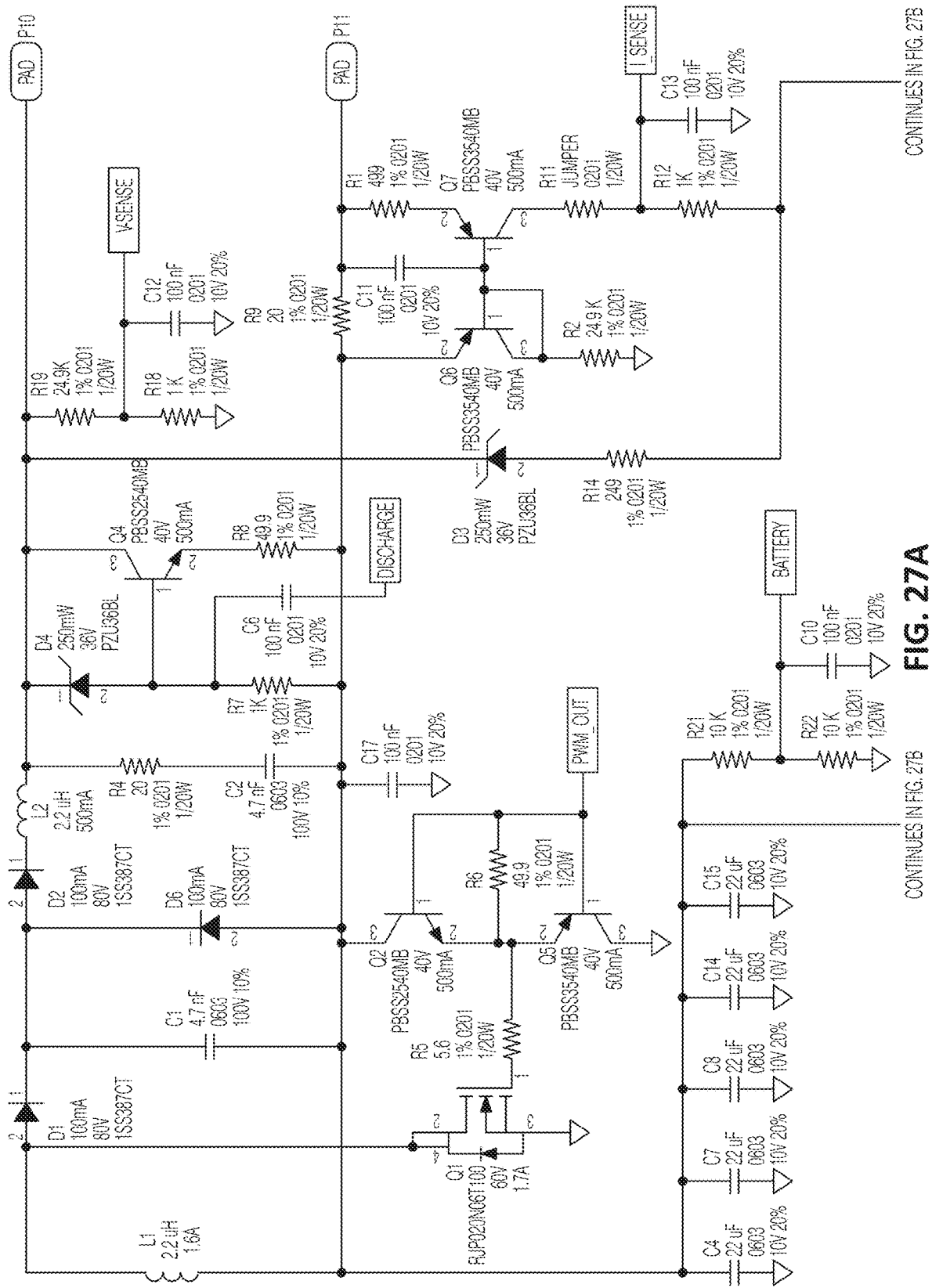
FIG. 27A-27C are each partial views showing is an exemplary circuit diagram for one variation of a limited-number-of-use, wearable neuromodulator as described herein.
Figure 27B:
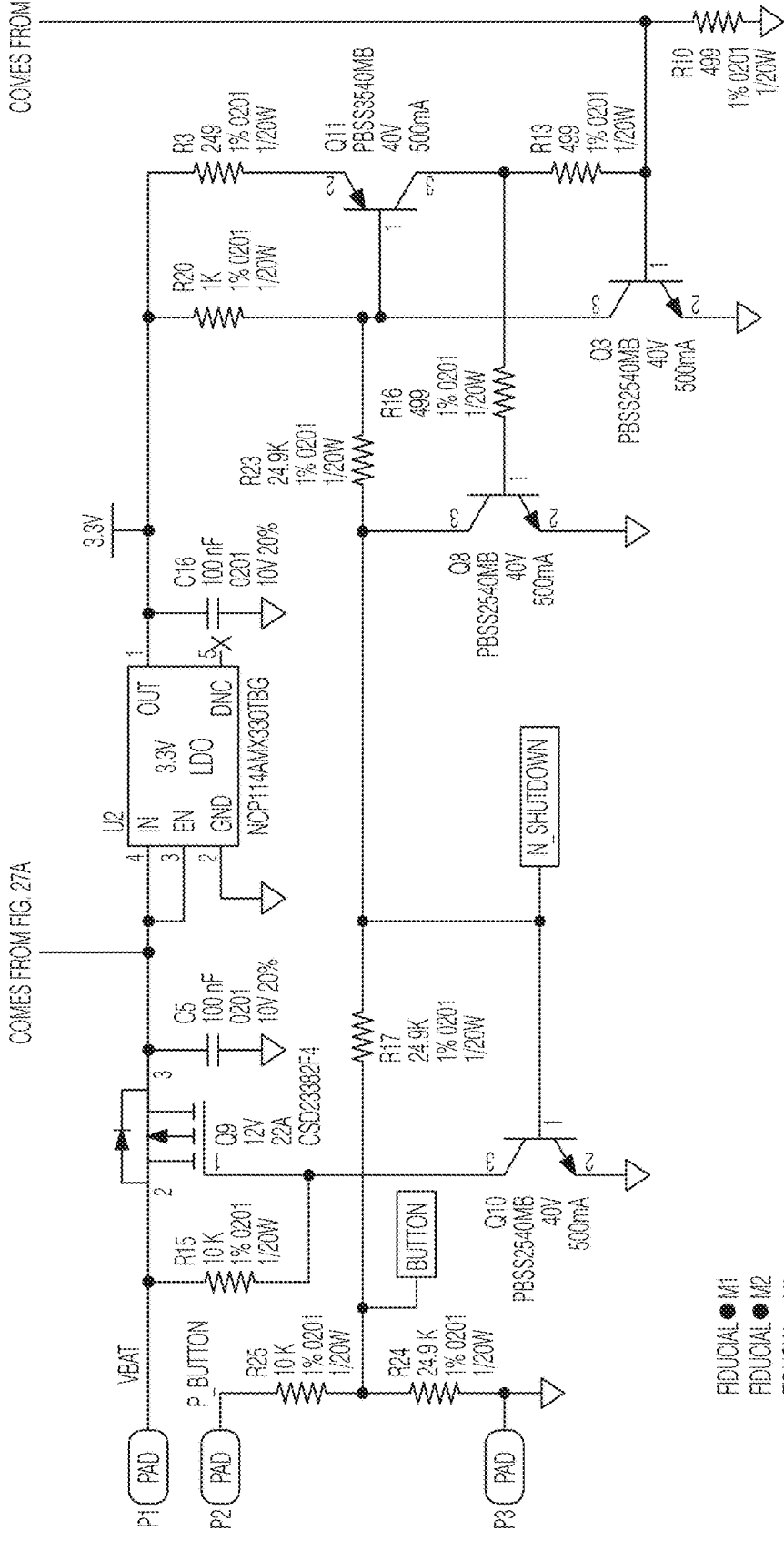
Figure 27C:
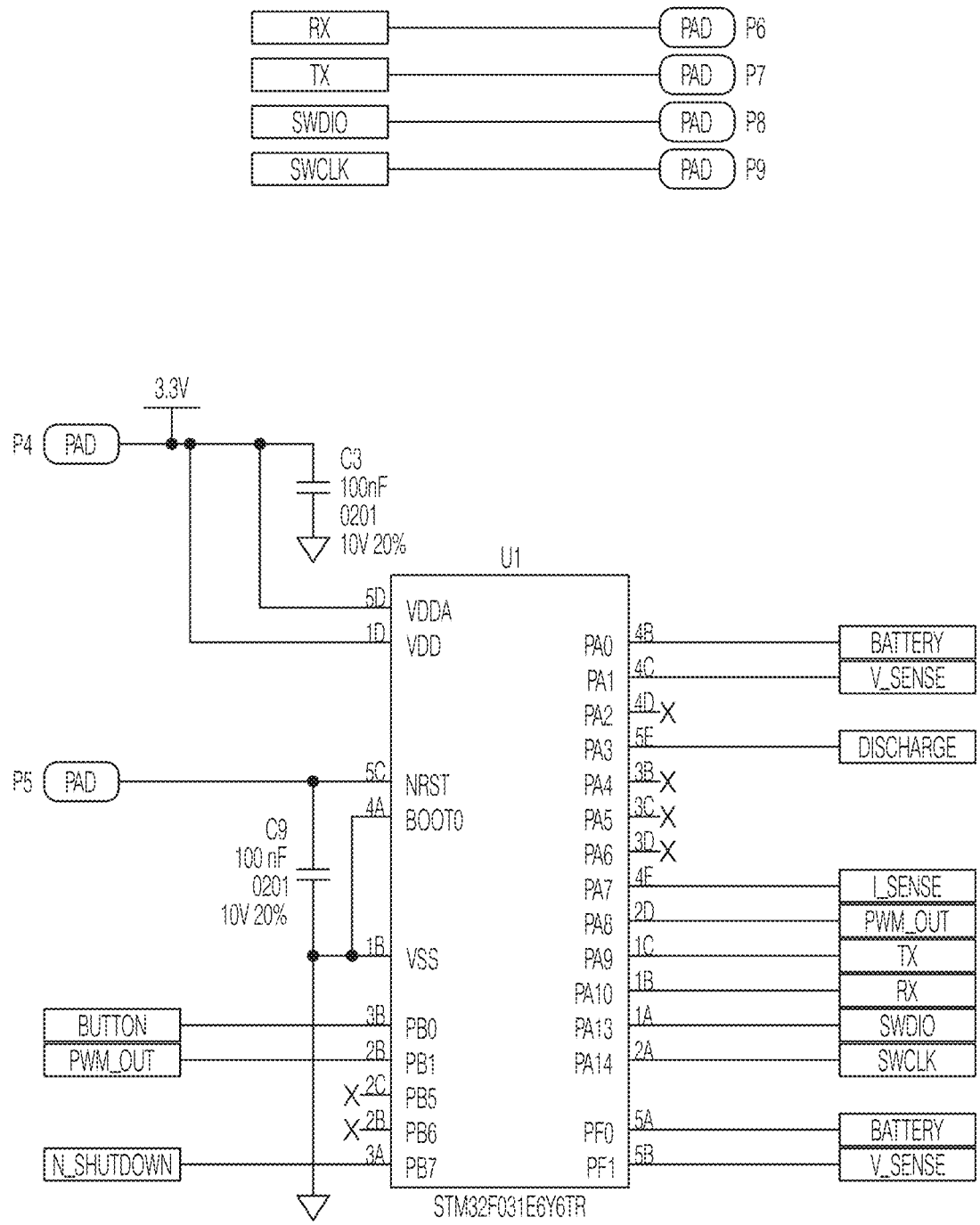

FIG. 27A-27C is a circuitry schematic for one example of a limited-number-of-use apparatus as described herein. In FIG. 27A-27C, the apparatus is configured for automatic regulation of electrical current. The electrical current sensor in this example feeds back into a microcontroller so that when the current goes down, the controller puts out more energy into the kick-up inductor so that the output stimulation increases to compensate for the decreased current.

In any of these apparatuses, the switching transistor may be controlled by the microcontroller to generate kick-up pulses. For example in FIG. 27A-27C, a Q1 transistor may run a pulse width modulated waveform at a pulse rate of about 1,000,000 Hz (1 MHz). The pulse width may range from 200 nano-seconds to 900 nano-seconds. This pulse may be applied to a miniature L1 inductor. The size of the inductor is inversely proportional to the frequency of the pulses. The 1 MHz frequency assures that we can use a tiny inductor to keep product small and light weight. When Q1 turns off after a pulse, energy in inductor L1 releases thru D1. This pulse is directed to the skin through P10 (the anode). The current from the skin returns through P11 (cathode) goes thru R9 to return to L1. Note that Q2 and Q5 amplifies the micro-controller's output to a large enough current to drive the switching transistor Q1.

The apparatuses described herein may provide step up boost converter filtering. The output of the kick-up inductor may have ripples since the circuit uses short bursts of energy put into inductor L1 to kick up the voltage. The apparatuses described herein may include a special design in this filtering to preserve energy and increase efficiency. For example, after rectifier D2, the components L2, C2, R4, along with the capacitance on the skin, may perform filtering of the ripple. When filter inductor L2 is sinking current (taking in current), voltage is going down in C1. If the voltage in C1 goes negative, it may take away energy. Instead, D6 is connected to reference node (C1's pin away from L1), so that L2 can take energy straight from the reference node, instead of drawing it from C1 when C1 holds negative charge.

Figure 28:
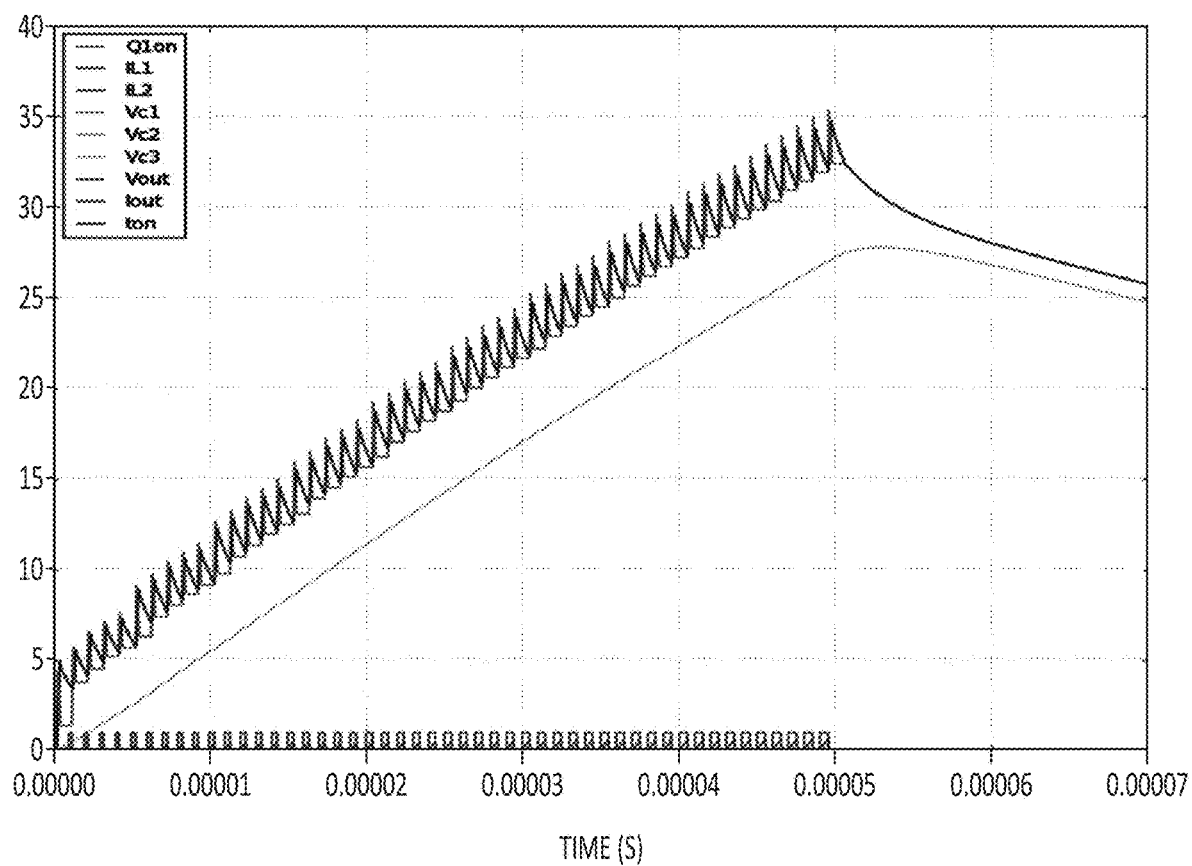
FIG. 28 show and example of a voltage ramp for a boost converter of a limited-number-of-use, wearable neuromodulator as described herein.

FIG. 28 illustrates simulation results showing the voltage ramp required of the boost converter. Note that the shape of the ramp is different depending on the duration of the constant current pulse, but is the same for different current levels. Horizontal axis is time, vertical axis is voltage at output of boost converter.

In any of the variations described herein, a low cost battery that has limited instantaneous current capability may be used. For example, a plurality of (e.g., four or more, five or more, etc.) capacitors, such as C4, C7, C8, C14, C15, may be arranged in parallel to store the charge from a low instantaneous current battery such as from an alkaline cell. These capacitors can be replaced by a super-capacitor which will have an even higher capacitance, though at a higher cost.

Any of these apparatuses may include a skin discharge circuit. For example, neuromodulation may include a discharge of the electric charge cumulated on the skin after each neural-modulating pulse. In one example, Q4, with a control line from the micro-controller, performs the skin discharge function when it is turned on. Further, any of these apparatuses may include a safety protection circuit. Although the battery may hold a very small amount of energy, and therefore the apparatus may be inherently safe due to the limited energy available, it is important that the circuit does not over deliver the current or voltage to the user. A zener diode D3 (e.g., a diode that conducts at the pre-set voltage limit) may be used to shunt the energy away from the user when the output exceeds a pre-determined voltage threshold, e.g., of 36 volts. When the tripping protection happens, in some variations Q3 and Q11 may latch, and may send the fault signal to Q8 which performs shutdown of Q9, and the battery is cutoff from the device for a total protection of the user.

Any of these apparatuses may also include neural-modulating current sensing. For example, the sensing circuit (e.g., the microcontroller) may be configured not to disrupt the sensor so as to maintain accuracy. For example, when the neural-modulating current goes thru P11 to R9, a positive voltage may be developed on C11. Q6 and Q7 both conduct (current mirroring). The voltage drop across R9 may be copied onto R1. The signal may then be acquired by the micro-controller, and used to determine if the current needs to be boosted or attenuated to maintain a stable current, and/or if the pads are attached to the skin and/or if the pads came off the skin and the user should be made aware.

Figure 29:
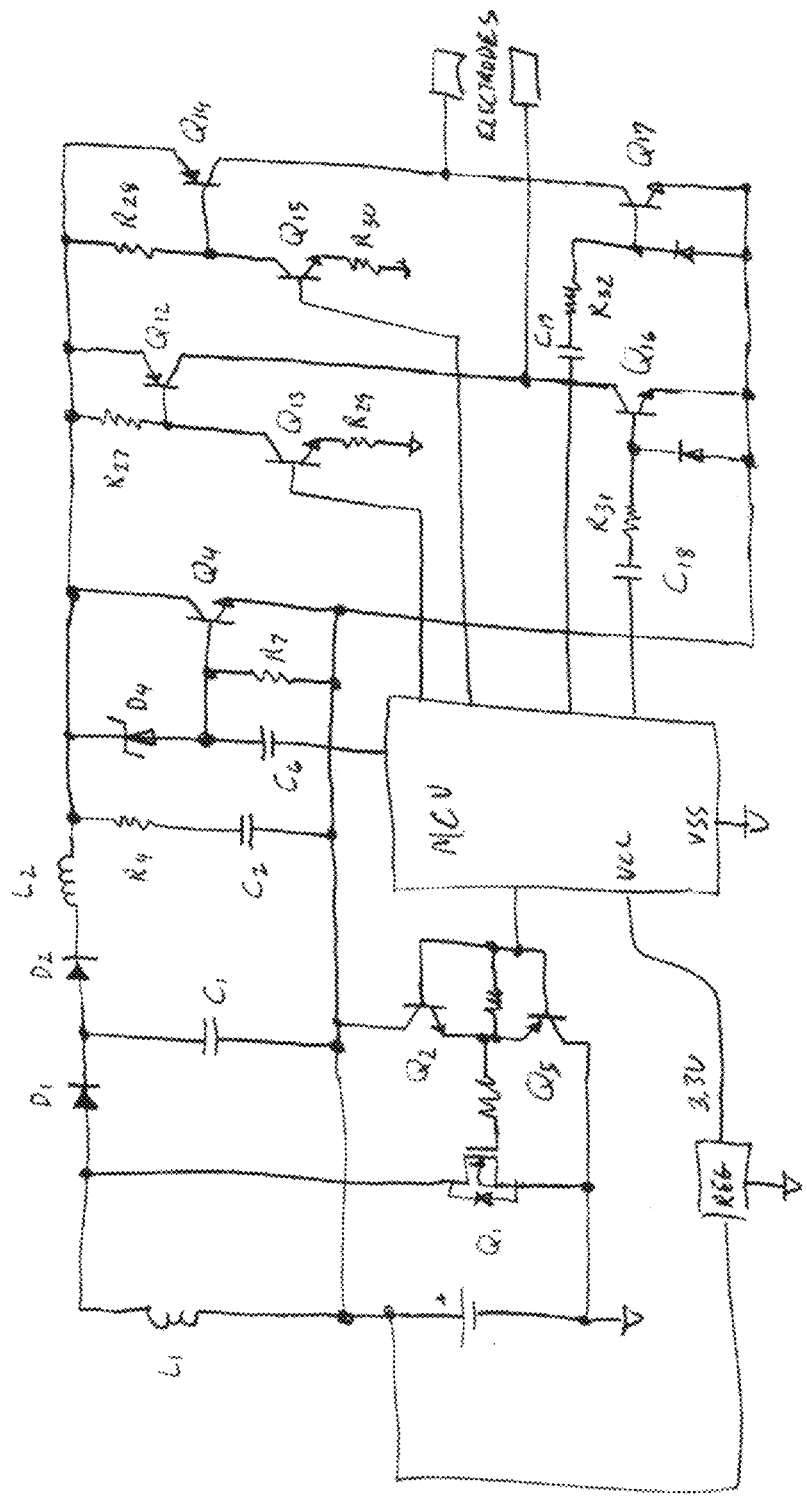
FIG. 29 is an exemplary circuit diagram for another variation of a limited-number-of-use wearable neuromodulator as described herein.

As mentioned, any of the apparatuses described herein may be configured to deliver a waveform having therapeutic effects, including inducing a calming effect. The calming effect may be induced using a waveform comprising a bi-polar pulse, e.g., a pulse of +ve and −ve current at different times of the modulation. FIG. 29 illustrates schematics for one example of a control circuitry that may provide a calming waveform. In FIG. 29, the schematics illustrate a circuit essentially similar to that of FIG. 27A-27C, described above for generating a constant current pulse, but also includes a set of 4 transistors to switch the polarity of the neural modulating pulse so that both positive and negative pulses are available for the modulation. In this apparatus, the transistor switches are controlled by the micro-controller so that polarities can be swapped at specific moments during the waveform.

For example, the variations shown in FIG. 29 includes a bridge circuit for reversal of output polarity under microcontroller control. In this example, Q12 is the switch for the positive side of the current pulse, with Q13 forming a current source driver to Q12. When Q12 turns on, the lower electrode receives a +ve voltage (it becomes the anode). Q17 turns on at the same time, connecting the upper electrode to −ve voltage. The output is called the B pulse. When the apparatus is ready to switch polarity, Q16 is the switch for the negative side of the current pulse. It controls the lower rail of the neural modulating current pulse. When Q16 is turned on, it connects the lower rail of the supply to the lower electrode. Q14 connects the upper electrode to the +ve voltage. This is called the A pulse.

In summary, the A pulse (+ve current pulse from device) occurs when Q16 and Q14 turn on; the B pulse (−ve current pulse from device) occurs when Q12 and Q17 turn on.

In any of these apparatuses efficient and low cost storage of the changing waveforms for neuromodulation in the limited-number-of-use device may be achieved by including a microcontroller and sufficient memory. For example, a micro-controller having 32 Kbyte of Flash memory may be used. 16 KB may be used for the main program and the remaining memory may be used for the storage of the modulating waveform. Although in some variations the neural modulating waveform may be fairly complex, a time-segment approach to represent the carrier waveform, needing only 4 parameters to fully characterize & represent the base carrier waveform at any one time, may be used.

For example, the carrier waveform may be amplitude modulated to achieve the best effects for neuromodulation, which may allow the storage of more than 800 (53×16) waveform transitions. The amplitude modulating envelope for the neuromodulation may be a trapezoid, so that through an adjustment of the trapezoid description, the modulation can be a) a triangular pattern, b) a ramping up saw tooth modulation, c) a decaying saw tooth modulation, or d) a symmetrical or e) a non-symmetrical ramp up and ramp down, f) the trapezoid modulation to start with a minimum amplitude that the neurons can respond to.

For example, a complex waveform may be economically described by 13 numbers: pulse A length; gap A length; pulse B length; gap B length; pulse A to start with this minimum amplitude, before ramping up; pulse B to start with this minimum amplitude, before ramping up; duration of this minimum amplitude. FIG. 30A is a table illustrating examples of some of these descriptors. For example, the duration that the trapezoid will be ramping up is shown in FIG. 30. FIG. 30A shows 13 stored parameters that may characterize an amplitude modulated waveform. In FIG. 30A, the list includes: pulse A to end with this maximum amplitude, before ramping down; pulse B to end with this maximum amplitude, before ramping down; the duration of this maximum amplitude; the duration of ramping down; the duration in the cycle where there is no amplitude modulation.

In general, the apparatuses described herein may comprise limited-number-of-use neuromodulator apparatuses configured to be worn on the user's skin for neuromodulation (e.g., to create an energizing or calming effect, a cognitive effect, such as improved memory, or a therapeutic purpose). These apparatuses (e.g., devices, systems, etc.) may include control circuitry and may include, e.g., printed layered structure that can be die cut or laser cut to form the device. These apparatuses may include a pair (or more) of electrodes that include a printed layered structure consisting of at least one layer of a conductive film (such as carbon or silver). Alternately the conductive film can be replaced by a stainless steel mesh. The printed layered structure may consist of a flexible substrate made of polymer fibers, such as, for example, Tyvek (Polyethylene fiber paper), polyimides, polyurethanes, etc. . . . Alternately or additionally, the flexible substrate can be a woven material (e.g., woven of synthetic fibers), and in some variations may be a knitted material.

Any of these apparatuses may include a printed circuit board assembly and a power source attached to the layered structure; the control circuitry may be formed by the printed circuit board. The printed circuit assembly may be capable of providing a constant electrical current pulse.

The conductive gel pad may be electrically connected to the controller circuit(s) (e.g., PCBA) through a conductive film and/or the stainless steel mesh. In some variations, the stainless steel mesh layer may be woven into the substrate in a way that maintains electrical isolation between two adjacent pads in the weave. The stainless steel mesh layer may be embroidered onto the flexible substrate in a pattern according to the anatomy of the target area. For example an oval inner electrode and a concentric reference electrode surrounding the stimulating electrode.

In some variations, a conductive trace from the control circuitry (e.g., a printed circuit board assembly) to the neuromodulation pads (e.g., electrode's gel pads) may pass through a 300 to 360 degree bend so that electrical connection is brought from one side of the flexible substrate to the other side. The printed circuit board assembly may be housed in a housing (e.g., enclosure) such as a plastic enclosure with connectors (e.g., mechanical connectors, such as dimples molded into the enclosure so that when a printed trace is inserted into the enclosure, the dimple presses on the trace to push onto the printed circuit assembly to make electrical contact). The substrate may be configured to include conductive fibers (e.g., made of a plastic polymer, or stainless steel) that may help the disposable device to retain its shape against an anatomical feature that's not flat.

In some variations, the control circuitry may include a wireless, e.g., radio frequency, emitter that identifies uniquely the device to a back end computer through the internet so that when the device is activated, the user is charged for the service. Any appropriate wireless emitter can be a near field communication device (NFC), or a blue tooth device, or a Wi-Fi radio working in conjunction with a phone or a wrist watch or a router. Alternatively, in some variations the simplified device may not provide output or receive input.

The control circuit(s) (e.g., control circuitry assembly) may contain a switching device (a transistor for example) switching on and off in a pattern that generates a DC voltage that changes amplitude with time so that the current going through the user's skin is a constant current pulse. The control circuitry may contain an energy storage device that stores the energy from a battery with limited current output capability so that there is sufficient energy to generate a neural-modulating constant current pulse before going back to a rest state to cumulate energy for the next pulse.

Any of these apparatuses may include a substrate that is woven or fibrous so that the substrate will unfold once removed from a miniature packaging and ready for neuromodulation. If fibrous, the fibers can be polymer strands, stainless steel strands, carbon fiber strands, or glass fiber strands. In some variations, the substrate may be a woven material. The fibers may allow the user to squeeze the device into a ball or other compact shapes for storage after use or between uses. The device will bounce back in shape once taken out of the container.

In any of the apparatuses described herein, the electrode may include a gel pad; the gel pad may contain an FDA approved chemical for cutaneous use to enhance the electrical conductivity of the skin where the gel is in contact. For example, the chemical may include a fragrance or a legal stimulant that embarks a sense of energy for the user. For example mild Capsaicin or Menthol. The gel pad may be a cotton pad infused with physiological saline or other solutes that goes into the skin through the electrical current applied with the purpose of assisting neuromodulation.

In any of these variations, the substrate may include "bumps" at locations where the substrate folds. The bumps may protect the printed-on conducting traces to limit the bending angle of the fold to avoid trace damages at the fold.

In any of the apparatuses described herein, the apparatus may include a battery. The battery may have less than about 80 milli-Amp hours in capacity due to the high efficiency of the circuit. For example, the battery may be a lithium polymer battery or 2 lithium polymer batteries in series with instantaneous current output capability less than 20 milliamps.

In any of these apparatuses, the control circuitry may have 10 or less components in the constant current pulse generating circuit. The control circuitry may be a printed circuit assembly (PCBA) that is about 1 cm×1 cm in size (or smaller). The maximum voltage output of the device may be between 10 volts and 50 volts (e.g., 20 V, 30V, 35V, 40V, 45V, etc.). The pulses going to the boost inductor in the control circuitry may be shorter than 1 microsecond in duration. These pulses may increase in duration monotonically during the delivery of a constant current pulse. A single resistor may be connected in series to the output of the apparatus and may measure the neuromodulation current.

In any of these apparatuses, the electrode may include an Ag/AgCl layer. The thickness of the Ag/AgCl layer may be dependent upon the maximum dosage to be applied by the apparatus. In some variations, a change in color when Ag is exhausted may provide a feedback to the user that the dose was delivered correctly. The thickness of plated silver may be less than 100 micron.

As mentioned, in some variations the substrates described herein may be flexible substrates, including woven substrates. In addition, the flexible substrate may be fibrous (e.g., plastics, paper, etc.). For example, a moldable pulp may be used to form a 3D shape to cover the electronics. Silver ink may be printed on paper to facilitate drying and increase conductivity by spreading silver ink into paper. Folding the substrate before a silver ink is fully hard may avoid cracking of a trace. Printing of an insulator may limit folding radius to prevent cracking of traces during fold. Any of these apparatus may use a fibrous material such as polyethylene fibers (e.g., Tyvek) as the substrate which may have a flexible material that bounce back in shape.

In general, the apparatus may be extremely lightweight. For example, the apparatus may have an overall weight of less than 1 oz., <15 g, <10 g, etc. The overall weight may be <7 grams (e.g., battery 1 gram, PCBA 2 grams, substrate/paper 1 grams, gel 3 gram) for a fully enclosed apparatus, which do not require a reusable connector between the gel pad and the control circuitry.

Any of the electrodes described herein may include a gel pad; the gel pad may be reasonably thin, but may use a material such as a mesh of conductive fibers for resistance spreading of the current evenly through the electrodes. This may be provided by, e.g., thin carbon traces. For example, isolated islands of gel may contact carbon pads. Alternatively or additionally, carbon Any of the apparatuses described herein may include a no controls (e.g., no buttons, etc.) and no control interface. The apparatus may include an auto-off after some amount of time (e.g., 10 seconds, 20 seconds, 30 seconds, etc.) of inaction when device is off skin.

The control circuitry for any of the apparatuses described herein may be configured to include a self-contained pulse generator; this pulse generator may use up to n transistors (where n is 3, 2 or 1) to generate the high voltage constant current pulses. The control circuitry may include a single transistor for discharge. The control circuitry may include polarity reversal (for bi-phasic waveforms), and may use up to 6 transistors.

The apparatuses described herein may include one or more integrated features. For example, any of these apparatuses may include a silver trace, carbon ink to spread out current, silver on cathode to replenish depleted Ag+ ion, and a gel pad. Any of these apparatuses may also or additionally include one or more integrated on-skin detection and pads-off detection.

In general, the waveforms described herein may be used may be of any appropriate complexity including, e.g., 3 or more segments, 2 or more segments, etc.). For example 4 or more segments for biphasic waveforms may be used. The duration of (uninterrupted) stimulation by the limited-number-of-use device may be any appropriate duration. For example, the duration may be a stimulation length of, e.g., <15 minutes, <10 minutes, <5 minutes, <3 minutes, etc. In general the duration may 15 minutes or less (less than 25 minutes, less than 20 minutes, less than 17 minutes, less than 15 minutes, less than 10 minutes, between 1 minute and 25 minutes, between 1 min and 20 minutes, between 1 minute and 15 minutes, between 3 minutes and 15 minutes, etc.)

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Waveform Charge per Phase

As mentioned above, in general, the methods and apparatuses described herein may be configured to provide a change per phase, Q (μC per phase), where Q may be defined as:

$$Q=(1000/F)*(C)*(pDut)*(pDC)$$

where F is Frequency, C is current (mA), pDut is duty cycle percentage, and pDC is the DC percentage. Examples of waveforms sown to be effective and their corresponding values for Q, F, C, pDut an dpDC are shown in FIG. 30B (Table 3).

Examples of the energy patch (energizing) waveforms that may be used are in rows 8-14 (Base 450 Hz to Base 1500 Hz). These may be applied in a concentric electrode format (see FIGS. 33B and 34A-34C, below) behind the ear within the examples described herein. The applied frequency regime may lead to different sensations for the user; the energy regime is approximately the same across these waveforms with between about 0.5 and 2 μC per phase (e.g., 0.5-3 μC/phase). In general, the waveforms herein may be between about 0.1 to 10 μC per phase. FIG. 30B also shows examples of waveforms that may be used to treat a disorder (such as psoriasis) as well as waveforms that may be used to evoke a relaxed cognitive state.

Pendulum Waveforms

Any of the waveforms herein may be pendulum waveforms. A pendulum waveform 'swings' back and forth around a center frequency or center amplitude or center duty cycle. For example, in some variations the frequency may be shifted (either continuously or as a step function) over a range of frequencies; the shifts do not need to be symmetric either in their time or their extent. For example, a pendulum cycle may take 2 to 20 seconds (e.g., between 5-11 second, about 8 seconds, etc.) for the full cycle. Two examples are described herein: (1) See FIG. 48 ("extra strength" strong sensations) and (2) see FIG. 49 (milder, smoother).

Pendulum waveforms may allow the waveforms to evoke a more reliable response from the subject because, e.g., changing parameters in this time scale may prevent adaptation. In addition, sweeping over a range may allow more users to experience an optimum spot in terms of sensation and effect, even given people vary anatomically and biologically in that particular region with respect to nerve anatomy/physiology and sensory responses.

Simplified Neuromodulator

Figure 31E:
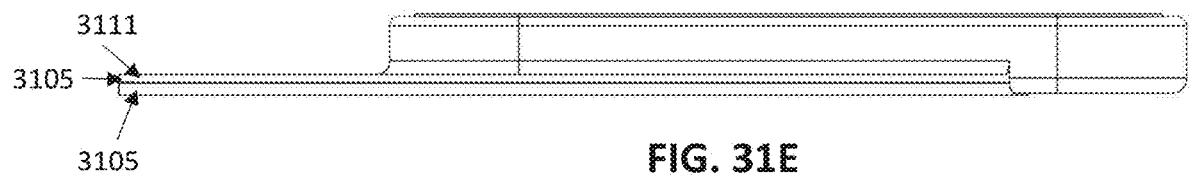
Figure 31F:
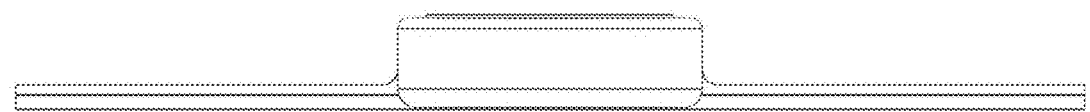
Figure 31G:
Figure 31H:
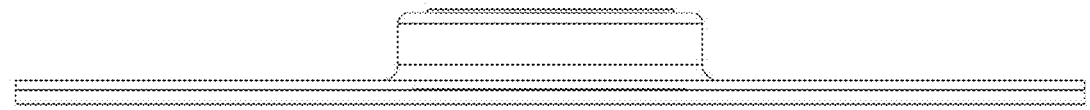

FIGS. 31A-31F illustrate one example of a first variation of a neuromodulator apparatus 3100. In this first example, the device is substantially flat, and includes a flexible substrate 3103 to which a pair of electrodes is attached. The first electrode includes a printed electrical contact in electrical communication with a conductive gel (e.g., hydrogel) that is sufficiently adhesive to hold the apparatus onto the skin until peeled off. An inner electrode 3107 also includes an electrical conductor in communication with a hydrogel. The inner electrode may be concentrically surrounded (completely surrounded, as shown in the example of FIGS. 31A-31H, or partially surrounded, as described below. In FIGS. 31A-31D, the opposite side of the substrate include a fabric cover 3111 that may be adhesively secure to the substrate and may be wrapped around and/or at least partially enclose the control circuitry and power source (within 3109). Thus the top of the exemplary device shown in FIGS. 31A-31H is an elastomeric fabric material, which may include an elastomeric cotton, for example, an elastomeric nylon, etc. FIGS. 31E-31H show side and front/back views of the apparatus of FIGS. 31A-31D. The elastomeric fabric cover material 3111 may be secured over the top of the substrate 3105 and the hydrogel electrodes 3105 may be attached to the bottom of the substrate, as shown in FIG. 31E. In this example the battery and the circuitry are enclosed within a housing formed by the elastomeric fabric; a frame or internal housing may hold the battery and control circuitry and may be wrapped with the elastomeric material.

In FIG. 31A-31H, the neuromodulator apparatus configuration may have a polyurethane substrate with silver forming the electrodes and traces. Axelgaard hydrogel may be applied to the electrodes in a concentric pattern, as shown. A liner may protect the hydrogel until the apparatus is to be used and applied. On top of the substrate, a battery, PCBA and a top cover made from elastomeric cotton with an acrylic adhesive on the underside may be used. An optional foam layer may be included.

Figure 32A:
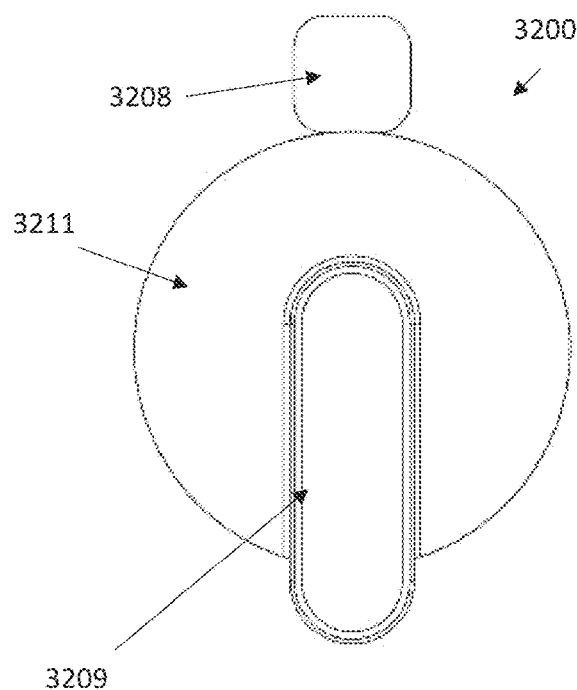
FIGS. 32A-32H illustrate one example of a limited-number-of-use wearable neuromodulator as described herein, having multiple layers of hydrogel and a release layer, configured to allow more than one use.
Figure 32B:
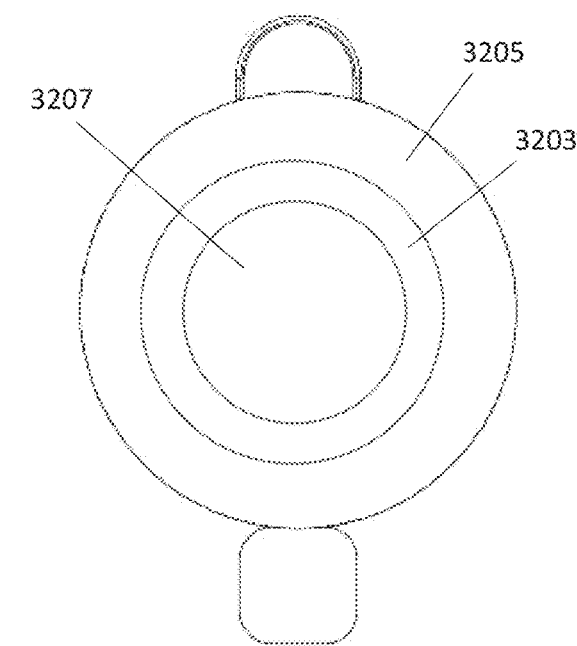
Figure 32C:
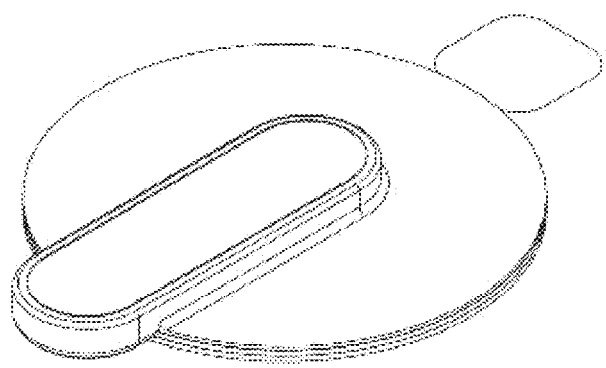
Figure 32D:
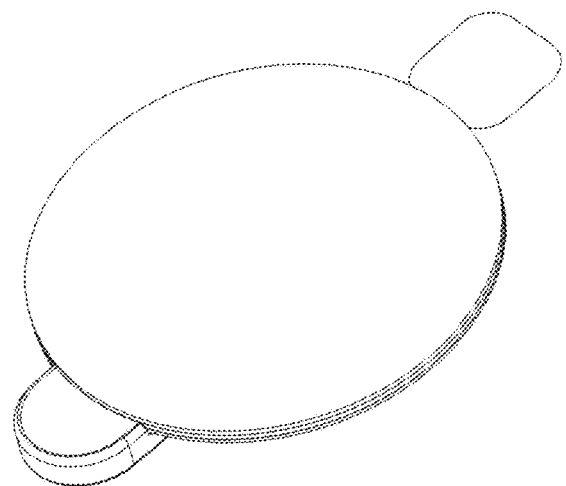
Figure 32E:
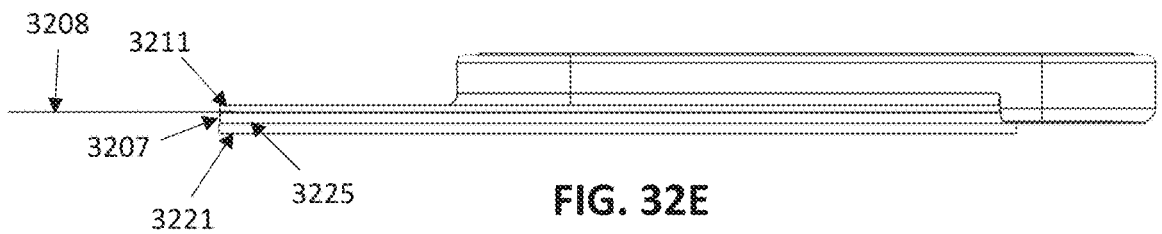
Figure 32F:
Figure 32G:
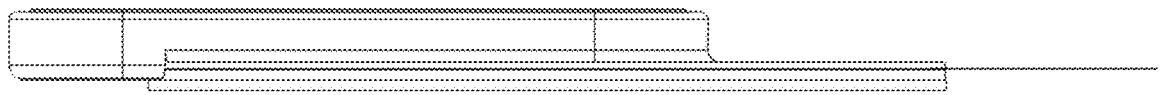
Figure 32H:
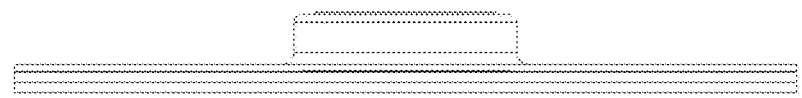

The apparatus of FIG. 31A may also include a circuit interrupt, such as a pull-tab that may be removed to connect the battery to the control circuitry (not shown in FIGS. 31A-31H). Another example, showing a pull tab (circuitry interrupt) 3208 is included as shown in FIGS. 32A-32H. In FIG. 32A the apparatus 3200 also includes a fabric (e.g., an elastomeric fabric) material cover 3211, wrapping an enclosing 3209 the power source and control circuitry (not visible). A pair of concentric electrodes (including concentric hydrogel regions 3205, 3207) are attached on the flexible substrate 3203. However in this example, as shown in FIGS. 32E-32H, a second hydrogel layer 3221, separated from the first hydrogel layer 3207 by a release layer 3225, may be included. Thus, any of these device may be configured two or more uses.

In general, these devices may include a circuit interrupt, such as a pull tab 3208, that is removed to engage the battery and start the stimulation. The device typically will not apply energy to the control circuitry the circuit interrupt is removed. Once remove, the apparatus will not apply a waveform until it detects that the electrodes are in contact with skin (e.g., via electrical measurement, e.g., impedance, resistance, etc.).

Figure 33A:
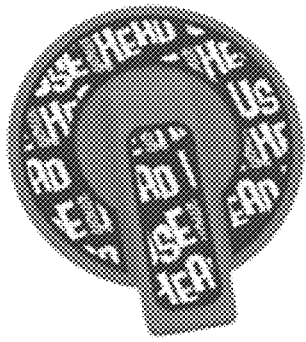
FIGS. 33A and 33B illustrate one example of prototype of a limited-number-of-use neuromodulator as described herein.
Figure 33B:
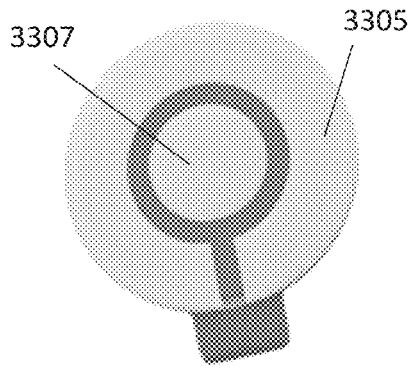

FIGS. 33A-33B illustrate top and bottom views, respectively, of a prototype apparatus for delivering neurostimulating waveforms as described herein. In FIG. 33A, the top of the device is covered in an elastomeric cotton material that wraps around and encloses the control circuitry and battery. The bottom shows the concentric electrodes (first electrode 3305 and second electrode 3307). This device is light (<15 g) and very flexible.

Figure 34A:
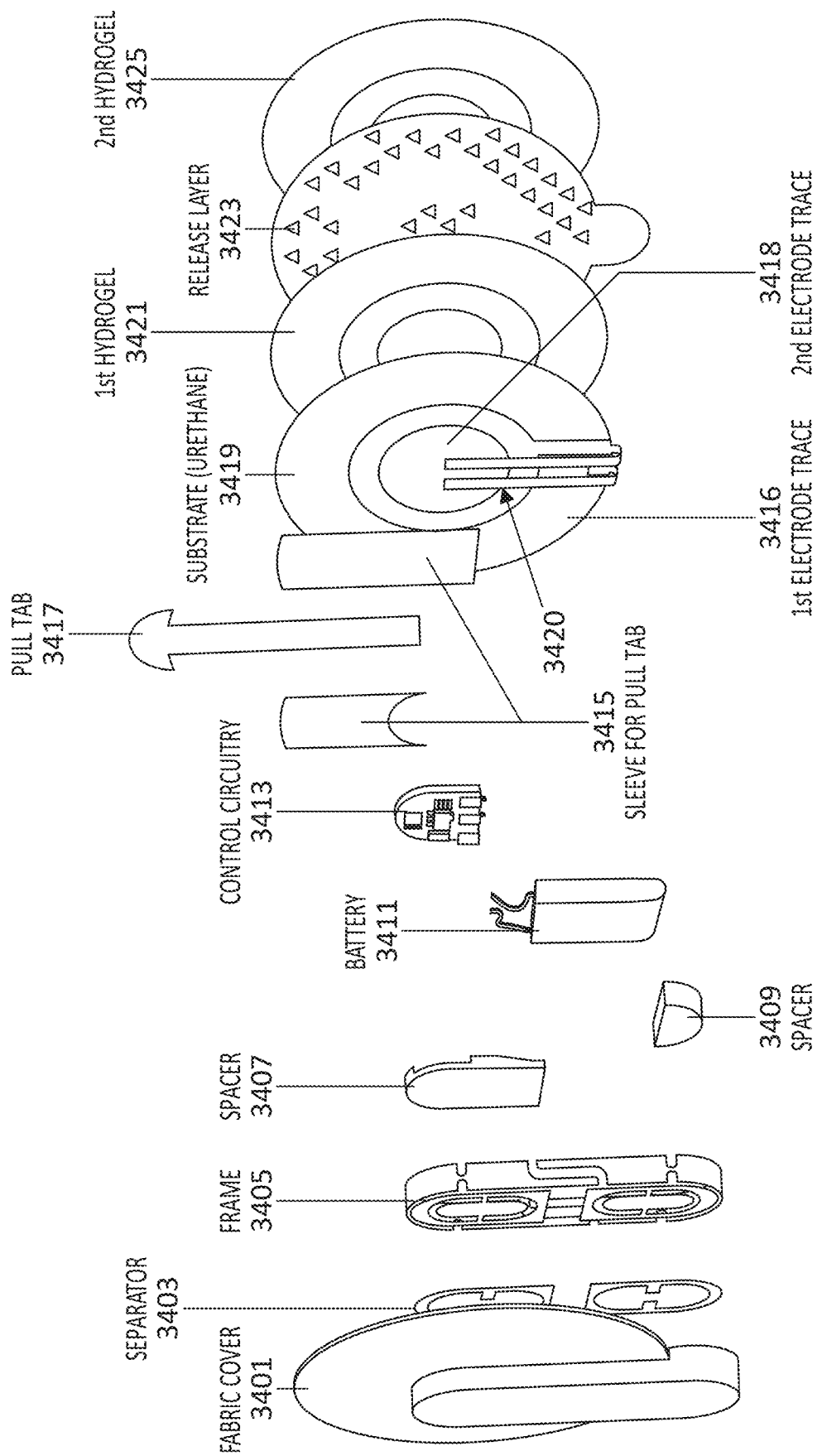
FIG. 34A is an exploded view of one variation of a limited-number-of-use neuromodulator as described herein.
Figure 34B:
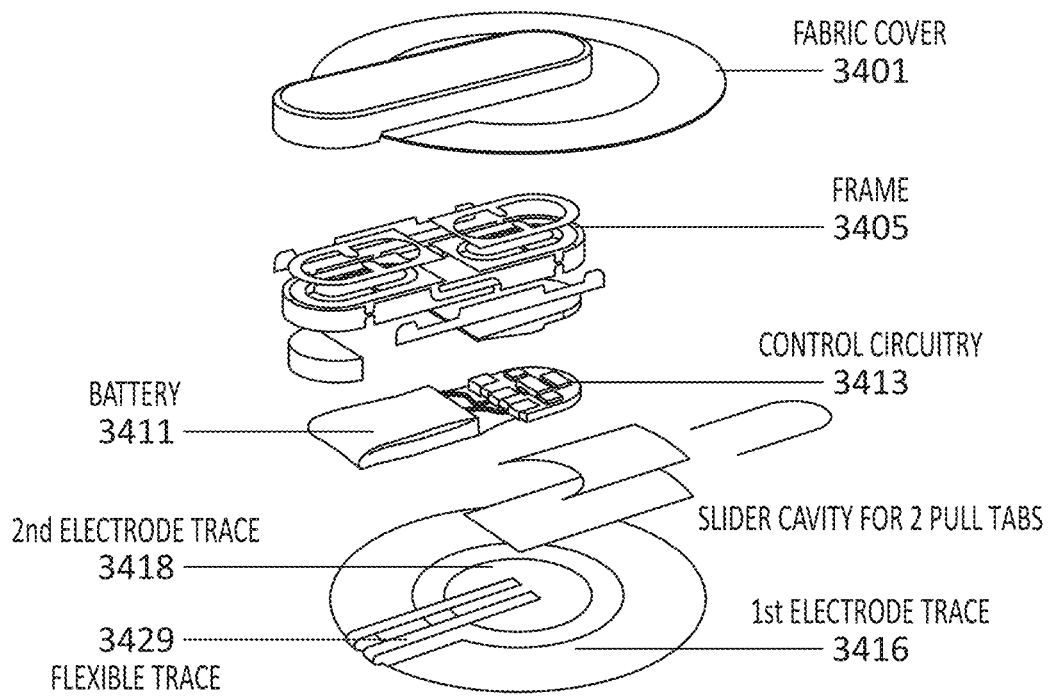
FIG. 34B is another example of an exploded view of the apparatus of FIG. 34A.
Figure 34C:
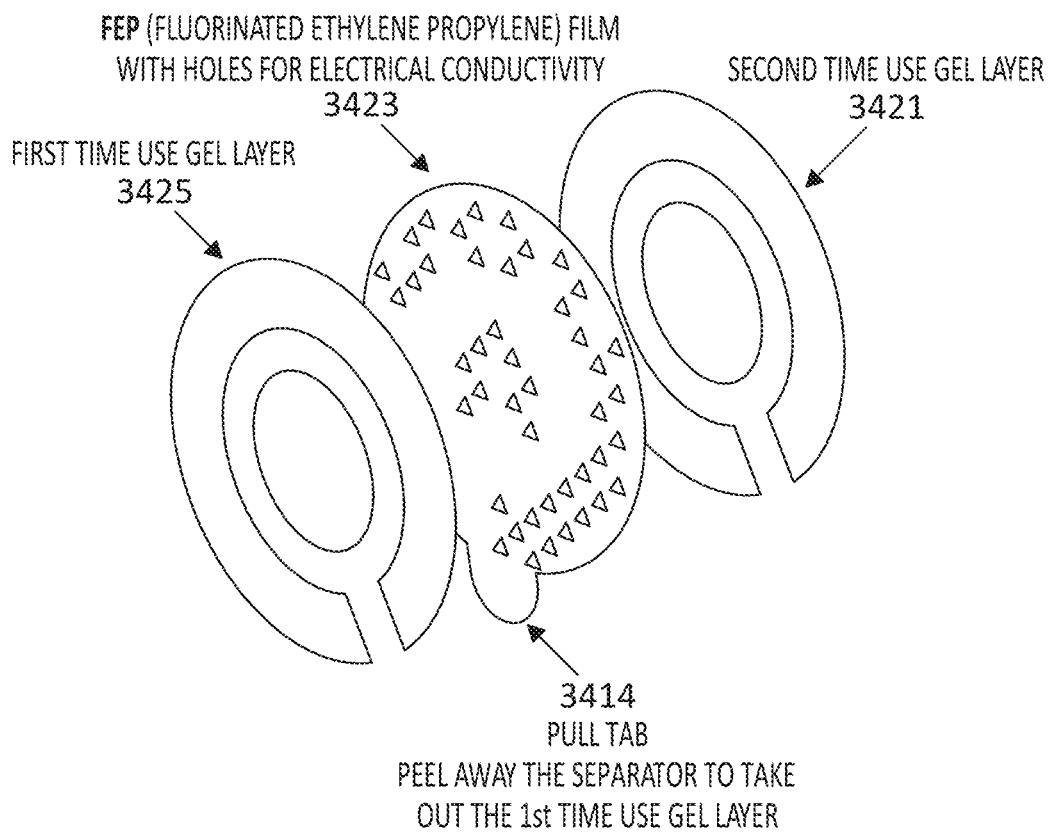
FIG. 34C is an example showing two layers of hydrogel separated by a release layer

FIG. 34A shows an exploded view of another variation of an apparatus, similar to that shown in FIG. 32A-32H. The apparatus includes a thin and flexible substrate (e.g., urethane 3419, onto which the electrodes 3416, 3418 and a connector trace 3420 have been printed. A pair of hydrogel regions, including a first hydrogel layer 3421 and a second hydrogel layer 3425 are layered onto the substrate on the bottom; the first and second hydrogel layers are separated by a release layer 3423. The release layer in this example is formed of an electrically insulating material that allows electrical connection between the hydrogel regions because of the cut-out openings over these regions, as shown. The electrodes are connected via the flexible traces (formed of the substrate) 3420 to the control circuitry 3413. A pull tab 3417 is interposed between the control circuitry and the battery 3411 (a sleeve 3415 for the pull tab may be included to allow it to slide freely out of the device when pulled). In this example, a frame 3405 and spacers 3407, 3409 may be included to hold the battery and circuitry, though the frame, battery and circuitry may be held between the cover 3401 and the substrate without being glued or attached onto the substrate. One or more separators 3403 may be used. FIGS. 34B and 34D show additional exploded views. For example, FIG. 34C shows the removable 'first time' or outer gel layer; the release layer may be pulled (by pulling the release layer pull tab 3414) to remove the outer hydrogel layer(s) 3425, exposing he inner layers. One or more components shown in the exploded views of FIGS. 34A-34C may be omitted from some of the variations described herein. For example, the device may not include a release liner and second hydrogel, a sleeve for the pull tab, a spacer, a frame, etc.

In FIG. 34B, the frame sub-assembly (e.g., frame 3405, spacers, etc.), battery 3411 and control circuitry 3413 are shown removed from the fabric cover 3401. The flexible traces may connect the first 3416 and second 3418 electrodes on the substrate to the control circuitry.

FIG. 34C shows the first hydrogel layer 3425 that includes a first hydrogel that forms part of the first (concentrically arranged, outer) electrode and a second hydrogel that forms part of the second (inner) electrode. A second hydrogel layer 3421 may include a third hydrogel that overlies the first hydrogel and is in electrical contact through the release layer 3423, which includes openings (e.g., cut-out regions) as shown. Similarly, a fourth hydrogel may overlay the second hydrogel of the second (inner) electrode and may also connect electrically through the release layer. In this example the release layer is formed of a fluorinated ethylene propylene (FED) film that has holes formed in it for electrical conductivity. The release layer also includes a tab (release layer pull tab) that can be used to peel away the release layer to remove the first (outer) hydrogel layer.

FIGS. 35A-35B illustrate one example of a method of wrapping an elastomeric fabric cover over the battery and/or circuitry. In this example, the fabric material may include an adhesive on one side (e.g., an acrylic adhesive) that can be used to wrap and secure the battery and/or control circuitry (and in some variations, a frame holding one or both of these). The fabric cover may also be attached (e.g., adhesively) to the back side of the substrate. In FIG. 35A the cover material (adhesive elastomeric material) 3501 is cut into a shape that allows it to wrap around the battery, frame, etc., as shown in FIG. 35B.

FIG. 36 shows another example of a neuromodulator apparatus in which the cover (e.g., in some variations a fabric cover) is removed. In this example, the battery 3607, and control circuitry 3605 are exposed, above (but not attached onto) the substrate on which the electrodes are formed (not visible in FIG. 36). In FIG. 36 a first circuit interrupt (pull tab 3615) is inserted under a clip 3631, preventing electrical connection between the battery and the control circuitry. A second clip 3617 may hold a second pull tab or pin 3617 that is connected to a release layer 3621 that may be removed (e.g., by pulling a pull tab 3613) to remove the 'used' hydrogel and expose a second 'clean' hydrogel beneath. The electrodes may make electrical connection by connecting through a flexible substrate onto which a conductive trace connecting to the first and second electrodes are coupled to a clip or attachment 3641 on the control circuit, as shown. Thus, the control circuitry is connected via a flexile connection to the substrate and the control circuit is also flexibly connected via two or more wires, to the power source (e.g., battery).

Figure 37A:
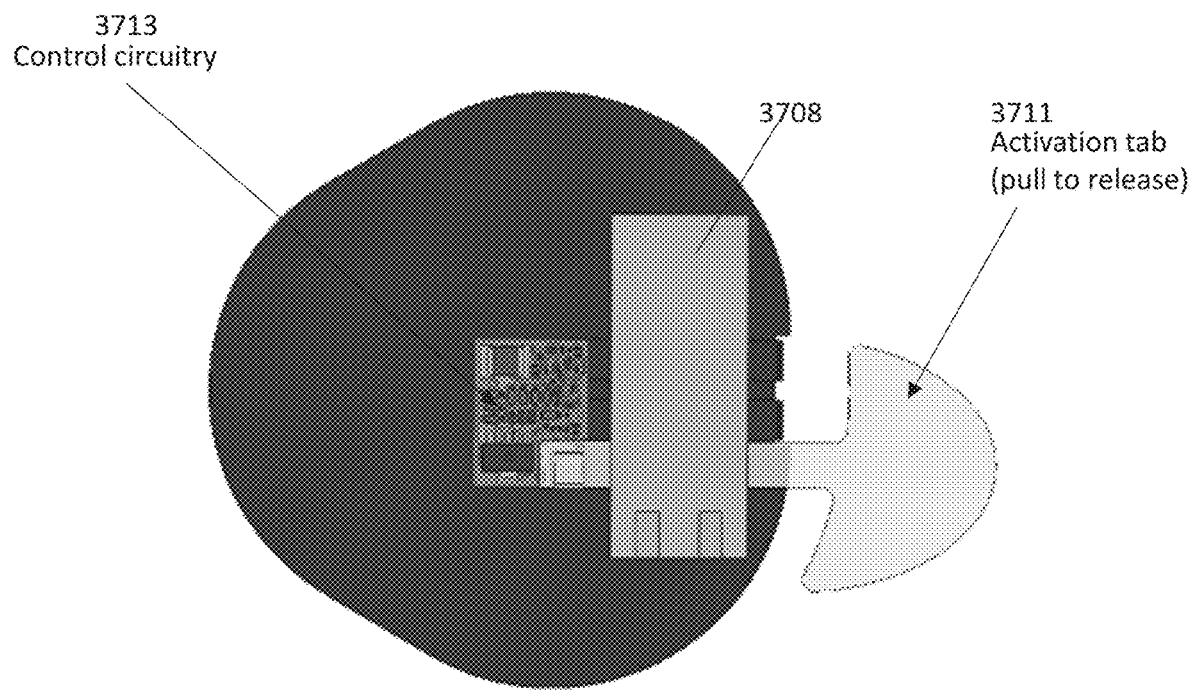
FIGS. 37A and 37B illustrate examples of a limited-use neuromodulators as described herein.
Figure 37B:
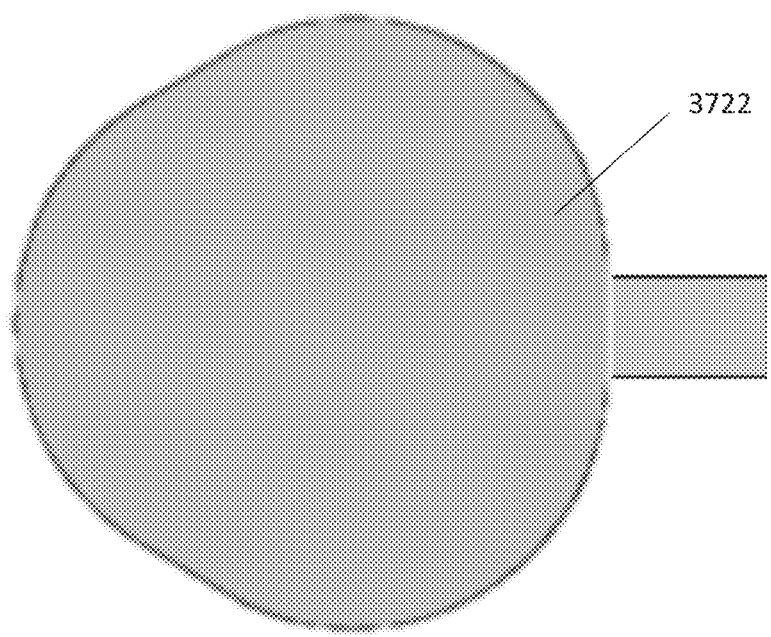

FIG. 36 shows another example of an apparatus in which the removal of the outer hydrogel by removing the release layer may also pull a second tab that allows the second waveform to be applied once skin contact is confirmed. This example also illustrates the circuit interrupt (pull tab) and is shown without the elastomeric cover material. FIGS. 37A and 37B illustrate alternative variations of neuromodulator apparatuses.

In FIG. 37A, the battery 3708 is arranged at an angle to the control circuitry 3713 and a circuit interrupt (pull tab 3711) is interposed in a clip 3715 on the control circuitry, preventing the battery from making electrical contact with the control circuitry until the circuit interrupt is removed, e.g., by pulling the tap out. FIG. 37 shows an example of a bottom (skin-facing) surface 3722 of an apparatus, which may include the hydrogel material forming the electrodes.

As mentioned above, the device may run for a preset time (e.g., 1-15 minutes, e.g., about 2, 3, 4, 5, 6, 7, 8, 9, 10, 11, 12, 13, 14, 15, etc. min), then stop. The device may then be removed and later re-applied. In some variations the original hydrogel may be 'reactivated' for attachment by adding a few drops of water to the hydrogel (bottom of electrode) and reapplied. Alternatively the outer hydrogel layer may be removed. Once the apparatus detects skin contact, it may again applying a waveform, for a second preset time. The waveform may be the same or different; if the hydrogel outer layer is removed, the second waveform may be different (e.g., lower intensity) than the first waveform. The apparatus generally include a battery that permits it to run for a preset time (e.g., max of 15 min. use 2× or 3×).

Figure 38B:
FIG. 38B illustrates the location of the application of a neuromodulator for inducing an energized cognitive state.
Figure 38A:
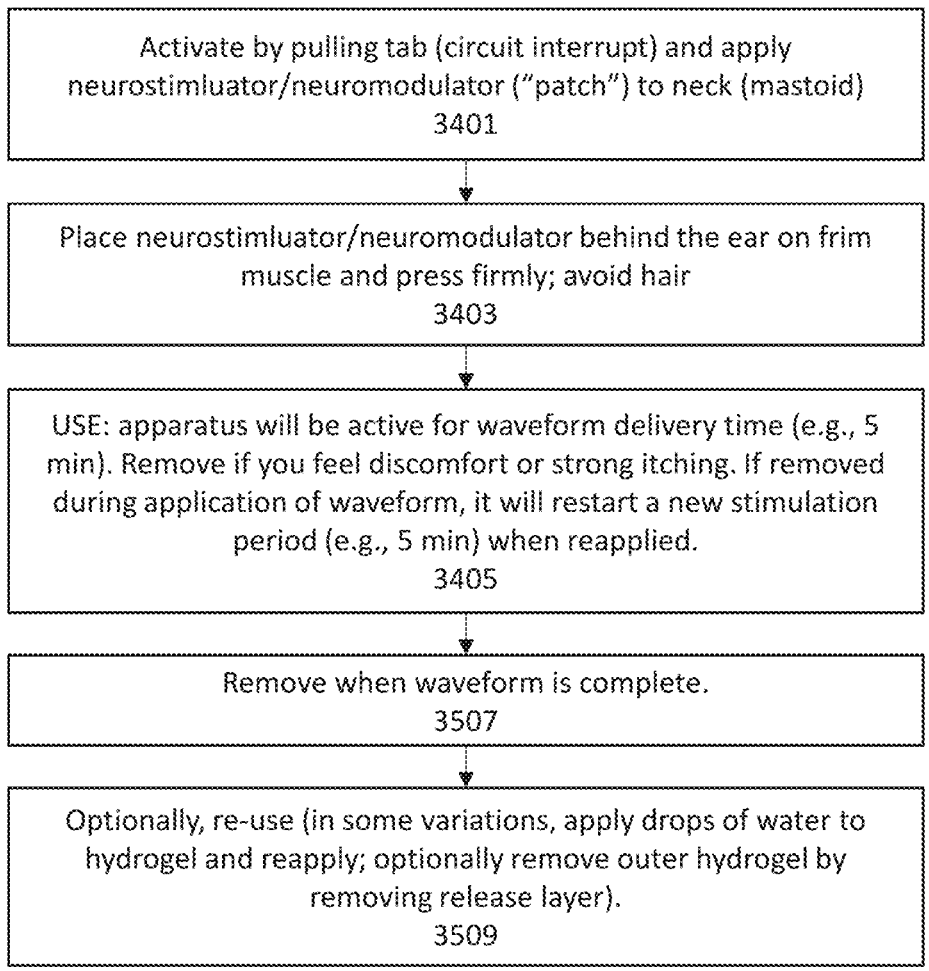
FIG. 38A is an exemplary method of using a limited-use neuromodulators as described herein.

In use, any of the apparatuses described herein, for any intended purpose (e.g., to evoke an energized state, to evoke a relaxed state, to enhance a cognitive function (e.g., memory, etc.), or to treat an indication, e.g., an inflammatory indication such as psoriasis, etc.) the method may generally include removing a circuit interrupt to allow the circuitry to detect skin contact, and applying electrical stimulation in a predetermined waveform until the treatment is complete or the device is removed. FIG. 38A illustrates one example of this.

In FIG. 38A, the generic method may include activating, e.g., by pulling a tab (circuit interrupt) from the side of the neurostimulator/neuromodulator ("patch"). Once in a standby mode, the neuromodulator may be applied, e.g., to the neck (mastoid) 3401, or any other appropriate region of the body. FIG. 38B illustrates one example of a method of applying the neurostimulator 3805 to the mastoid region, e.g., behind the ear. For example, the neurostimulator/neuromodulator may be placed behind the ear on frim muscle and pressed firmly in place, while avoiding hair. 3403.

Once applied, the device may be activated to deliver the pre-defined waveform. For example, the apparatus may be active for waveform delivery time (e.g., 5 min, 7 min, 10 min, 12 min, 15 min, etc.). The device may be removed if the subject feels any discomfort or strong itching. If the device is removed during application of waveform, it may restart a new stimulation period (e.g., 5 min) when reapplied 3405. Once the waveform is complete, the device may be removed, as it will enter into a stop mode, which may require a time delay and/or a second activation (e.g., pull tab, etc.) before it may delver a second/subsequent dose 3507; optionally, the device may be re-used (in some variations, apply drops of water to hydrogel and reapply; optionally remove outer hydrogel by removing release layer) 3509.

Figure 39A:
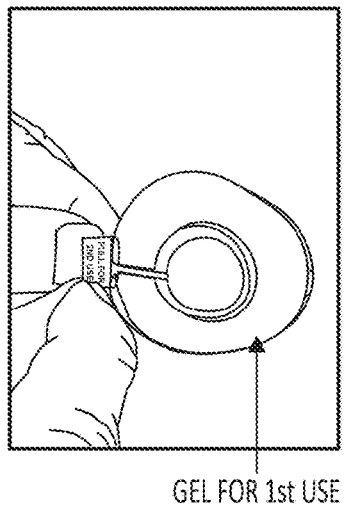
FIG. 39A-39C illustrates one method of removing a used layer of hydrogel by pulling on a release layer.
Figure 39B:
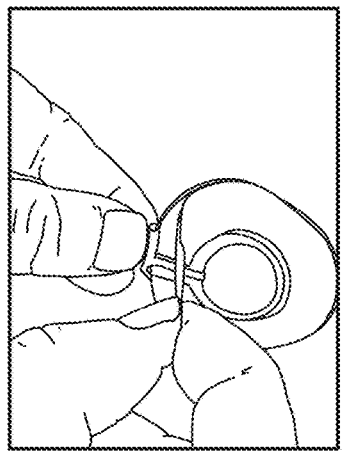
Figure 39C:
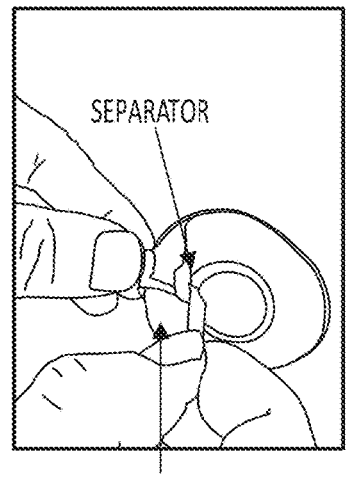

In variations in which a second (or subsequent) dose may be applied, the second or subsequent dose may be different than the first dose. For example, in variations in which the initial or first hydrogel layer is removed (e.g., by pulling off the outer hydrogel as shown in FIGS. 39A-39C, the second or subsequent waveform may be adjusted so that the waveforms delivered are approximately equivalent; thus, the intensity of the second waveform may be lower than the intensity of the first dose.

Figure 39D:
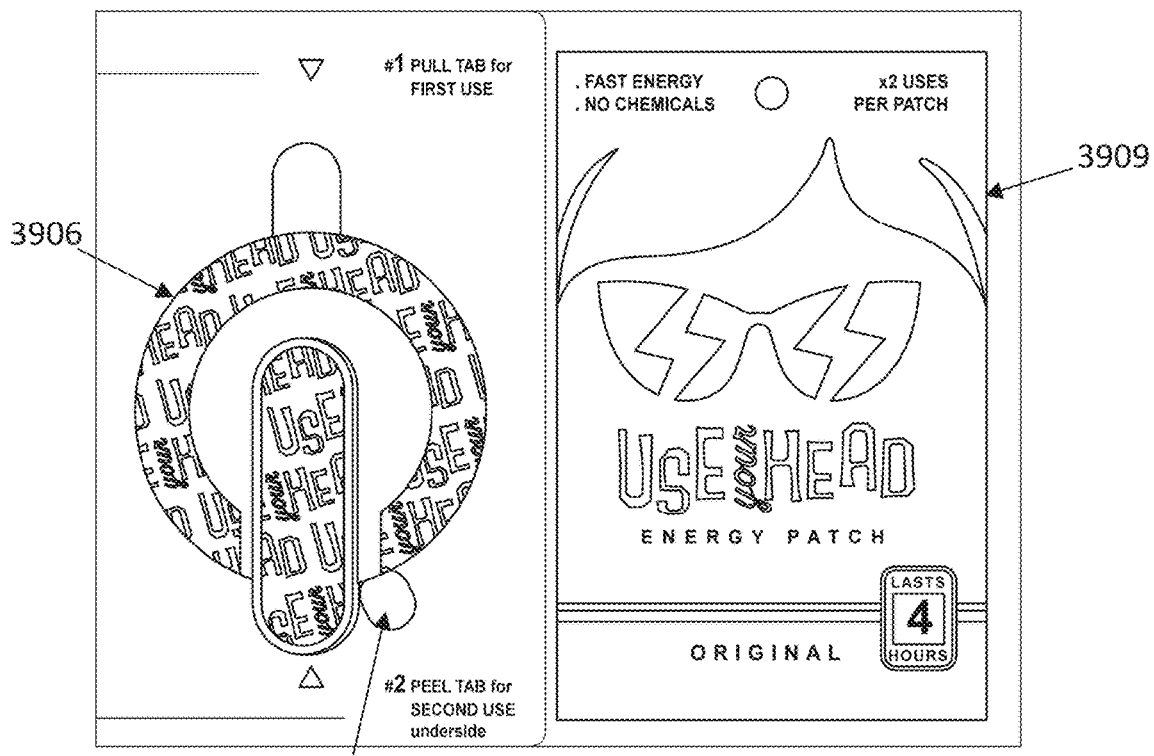
FIG. 39D illustrate an example of a neuromodulator and packaging (e.g., foil packet).

FIG. 39D illustrate an example of a neuromodulator 3906 and packaging (e.g., foil packet 3909). The apparatus may be sealed in the foil packet and removed by treating it open. To activate the device, a pull tab may be removed and the device may be peeled form the backing and applied directly to the skin.

Figure 40:
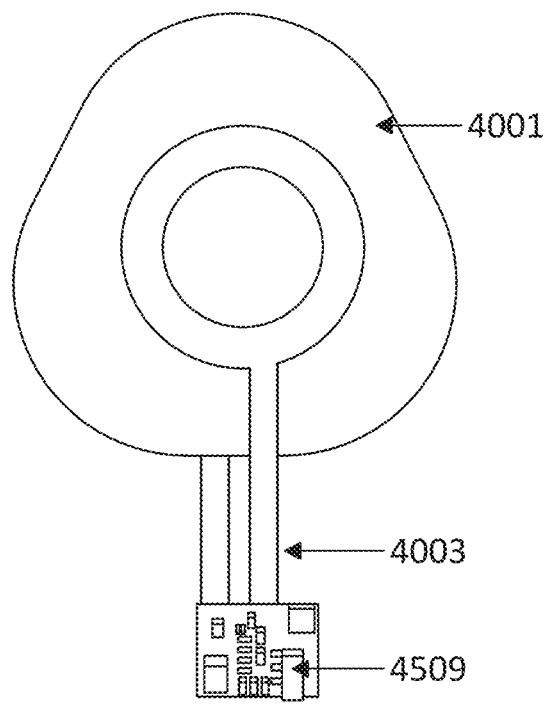
FIG. 40 is one example of a partial view of a neuromodulator including a pair of concentrically arranged electrode (electrode trace and conductive and adhesive hydrogel, each connected to a control circuitry).

The apparatuses herein may include multiple layers of gel (e.g., hydrogel) that may be removed to expose a clean hydrogel for repeated use. For example, FIGS. 40-47 illustrate one exemplary method of forming a neuromodulator apparatus having multiple layers of hydrogel. FIG. 40 is one example of a partial view of a neuromodulator including a pair of concentrically arranged electrode (electrode trace and conductive and adhesive hydrogel, each connected to a control circuitry). The first gel layer 4001 is shown as an electrolyte on silver electrode. The conductive traces 4003 connect the electrodes to the control circuitry 4509 and are flexible.

Figure 41:
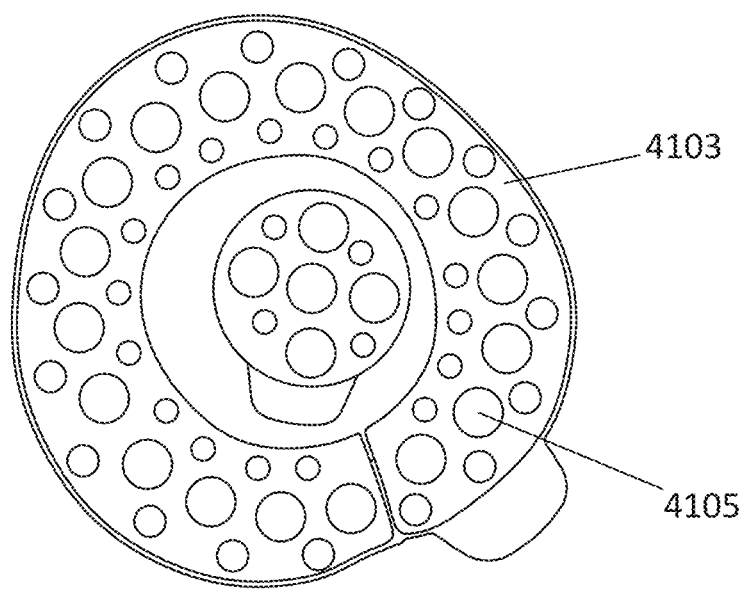
FIG. 41 is an example of a release layer (configured as two separate release layers) for use with a neuromodulator apparatus as described herein.

FIG. 41 is an example of a two-part release layer (configured as two separate release layers) for use with a neuromodulator apparatus as described herein. In this example, an outer cover (e.g., an elastomeric cover) is not yet included, and thus the control circuitry is exposed; the power source (e.g., battery) has also not yet been added. The release layer 4103 may be, for example, a hydrophobic film, such as a wax paper or silicone film. Holes 4105 in the release layer may provide electrical conductivity from the first hydrogel layer to the second gel layer.

Figure 42:
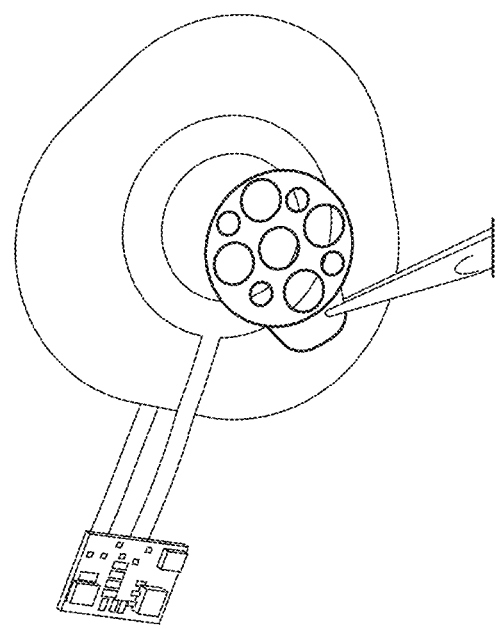
FIGS. 42-46 illustrate one method of forming a limited-number-of-use neuromodulator apparatus with a pair of release layers.
Figure 43:
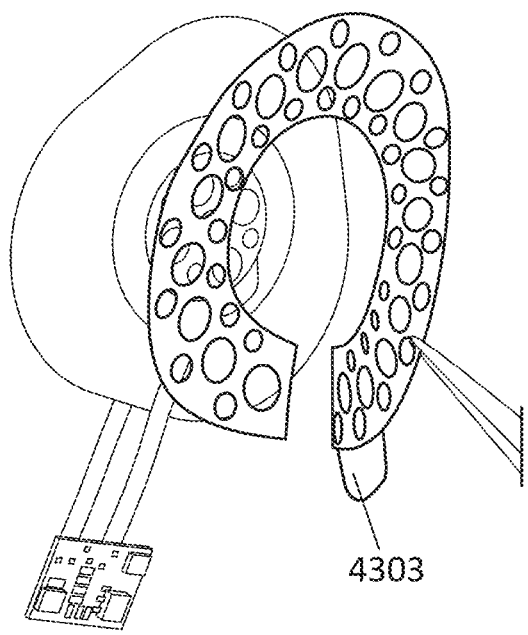
Figure 44:
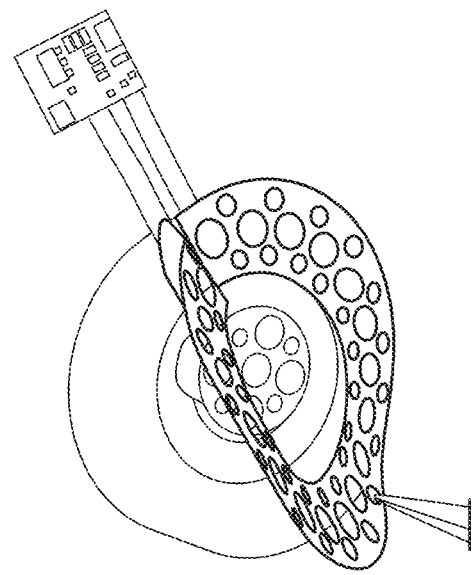
Figure 45:
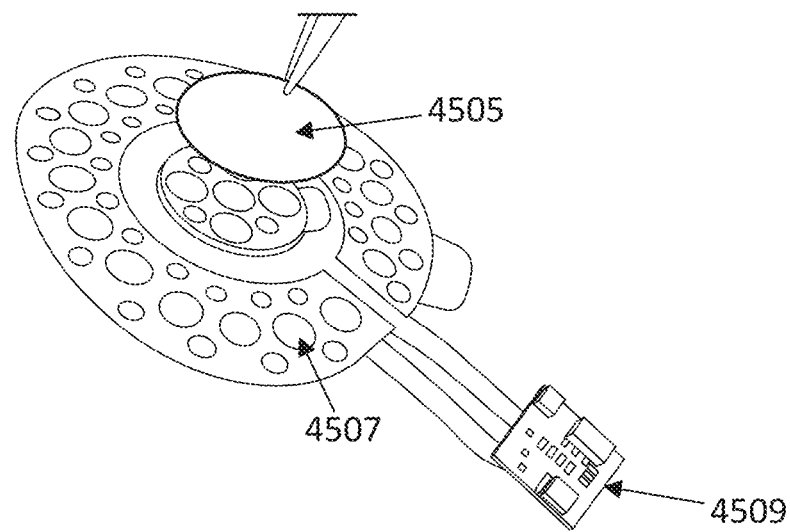
Figure 46:
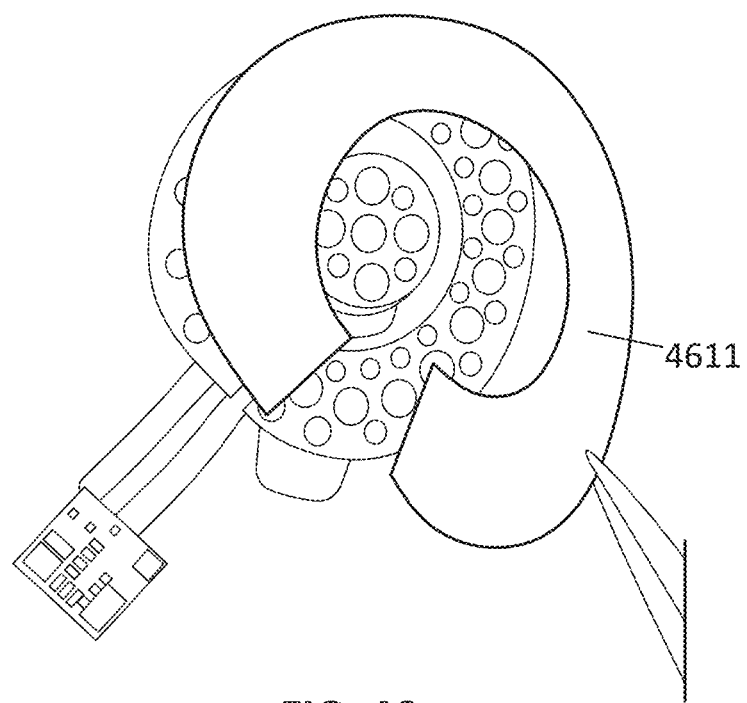

In the example shown in FIGS. 40-47, the limited-number-of-use neuromodulator apparatus with a pair of release layers (in some variations only a single release layer may be used, as shown in FIGS. 34A and 34C, above). FIG. 42 shows placement of a first release layer on the second (inner) electrode; FIGS. 43 and 44 show placement of the outer release layer on the first (outer) electrode that is concentrically around the second electrode. The release layer may include a release layer pull tab 4303. FIG. 45 illustrates placement of a second gel layer 4505 for the second (inner) electrode. The first gel layer 4507 is visible through the holes in the release layer. FIG. 46 shows placement of the second gel layer 4611 for the first (outer) electrode.

Figure 47:
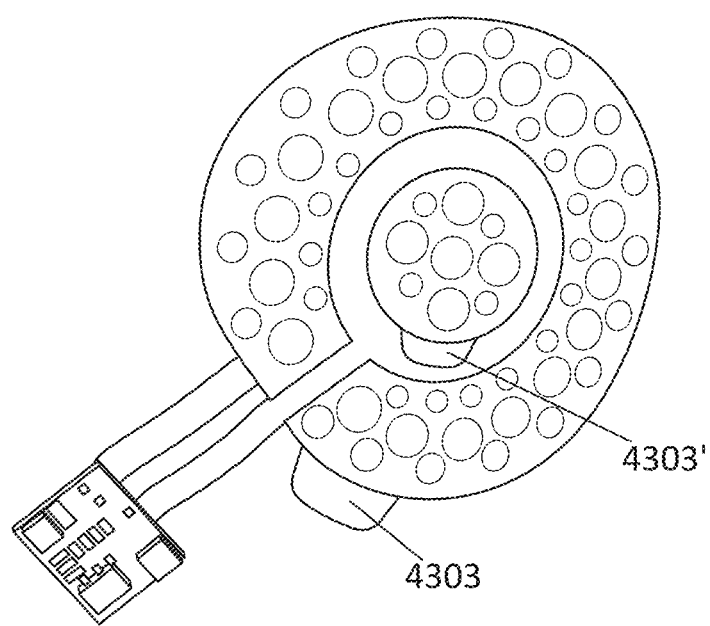
FIG. 47 illustrates the example the assembled limited-number-of-use neuromodulator apparatus assembled as shown in FIGS. 42-46. This variation includes multiple (e.g., 2) layers of conductive gel; after the first use a layer of the gel may be removed, leaving the fresh under layer. In this example, separate pull-tabs may remove the inner and outer gel regions after use; these may be combined into a single release layer.

FIG. 47 illustrates the example the assembled limited-number-of-use neuromodulator apparatus assembled as shown in FIGS. 42-46. This variation includes multiple (e.g., 2) layers of conductive gel; after the first use a layer of the gel may be removed, leaving the fresh under layer. In this example, separate pull-tabs 4303, 4303' may remove the inner and outer gel regions after use; these may be combined into a single release layer.

Figure 48:
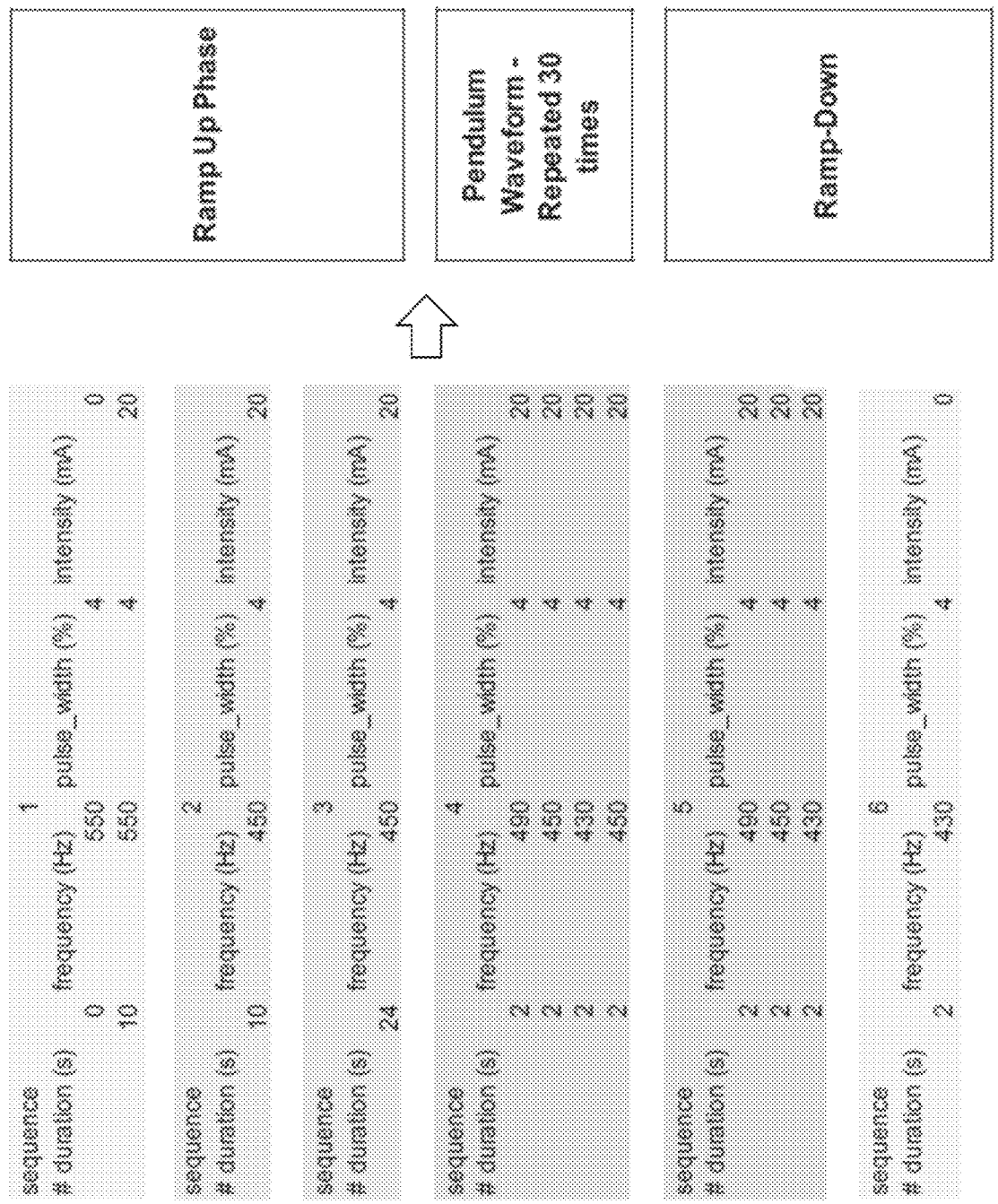
FIGS. 48 and 49 illustrate examples of pendulum waveforms that may be used with a strong (FIG. 48) and mild (FIG. 49) stimulation waveforms.
Figure 49:
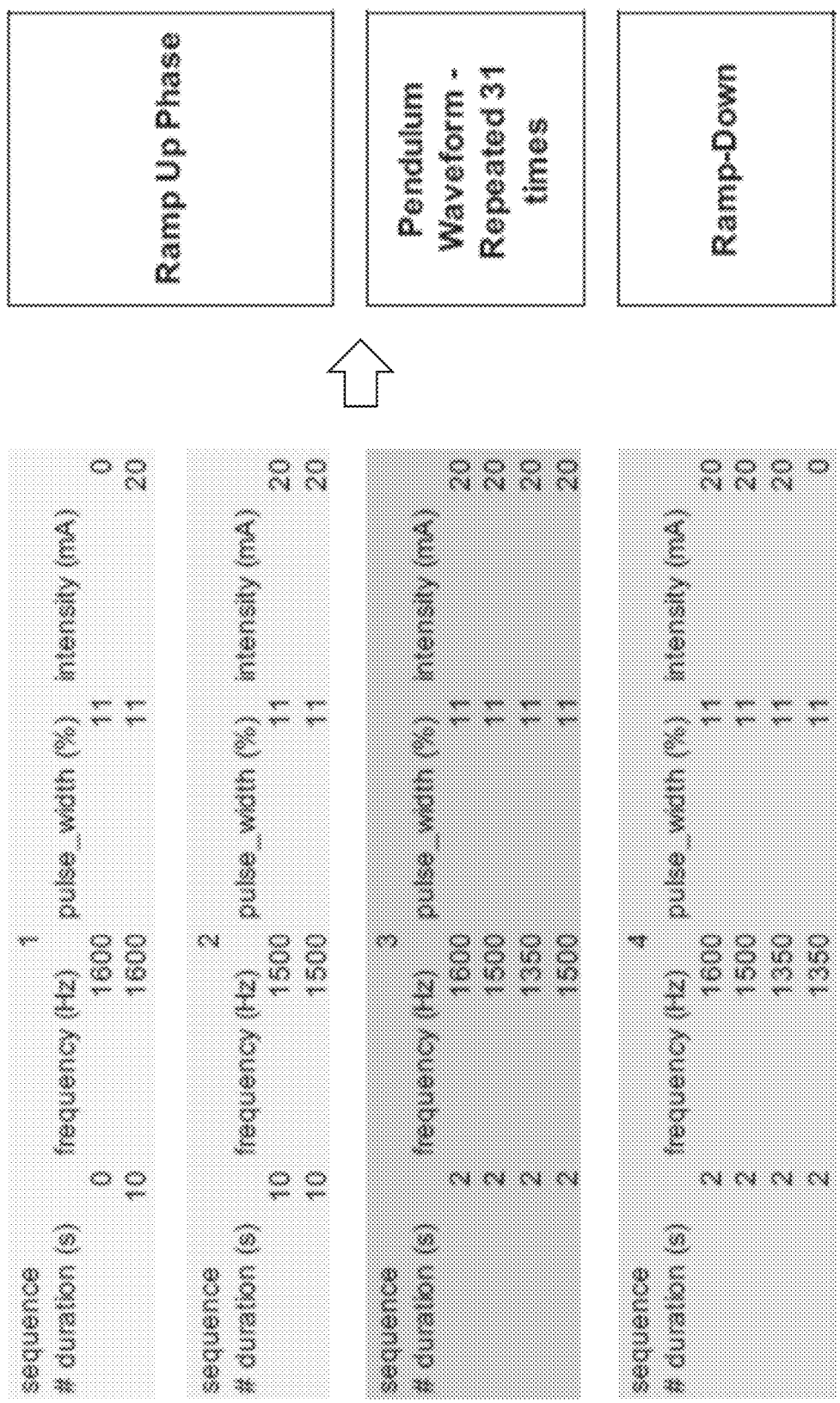

FIGS. 48 and 49 illustrate examples of pendulum waveforms that may be used with a strong (FIG. 48) and mild (FIG. 49) stimulation waveforms. FIG. 48 shown one example of an energizing waveform that is configured to result in an energizing effect. As sown in FIG. 48, the parameters for the pendulum waveform are shown. At each defined (pre-defined) point in time, the frequency, pulse width %, and intensity are indicated. This waveform description may be encoded into firmware, software of hardware for running off of the control circuitry. Similarly, FIG. 49 shows another example of a stimulation/neuromodulation waveform.

Figure 50:
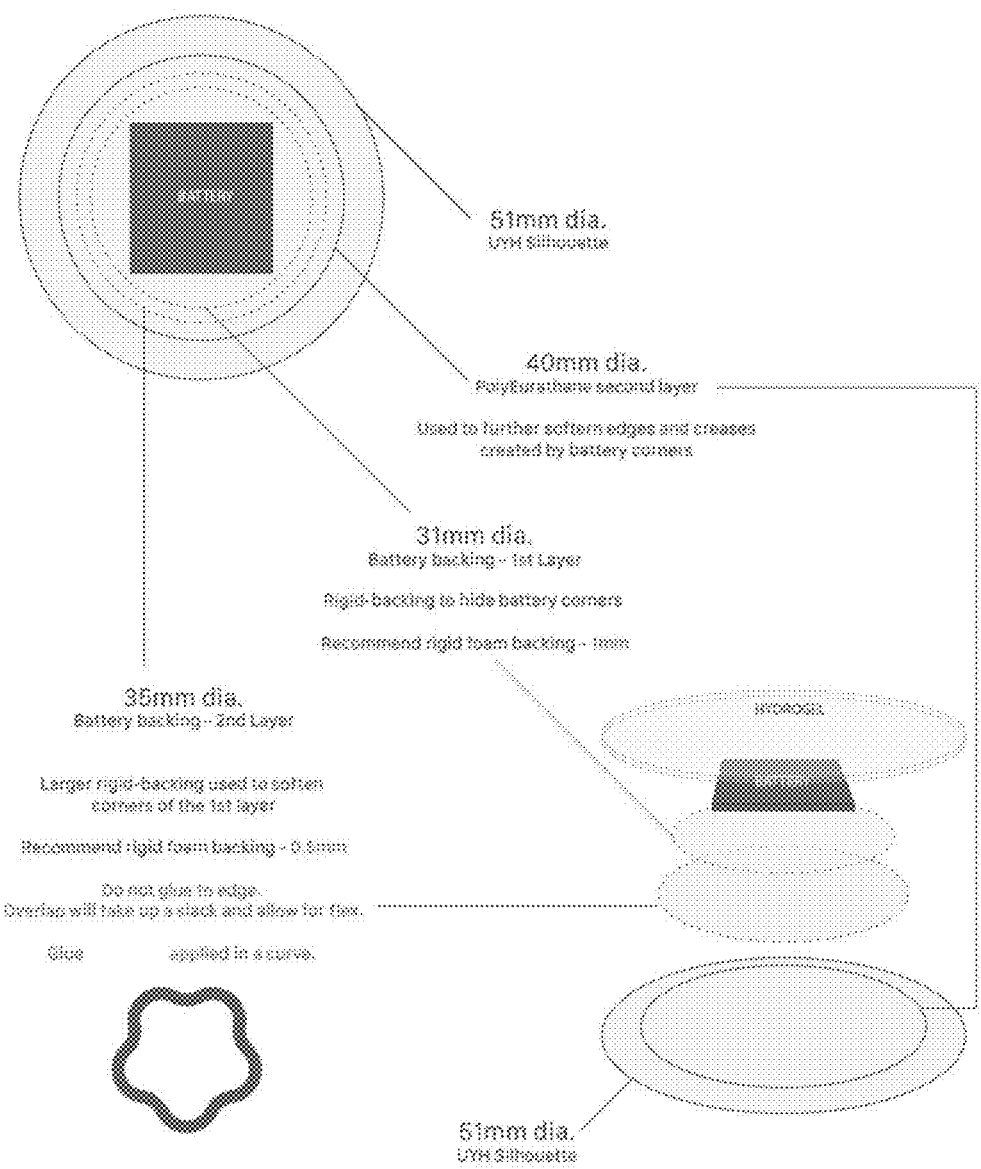
FIG. 50 is another example of a limited-number-of use neuromodulator as described herein.

FIG. 50 is another example of a limited-number-of use neuromodulator as described herein. In FIG. 50 the device includes a battery that is stacked directly onto the backing and the other layers forming the apparatus. The dimensions and materials indicated are for illustration only; other dimensions and materials may be used.

Figure 51:
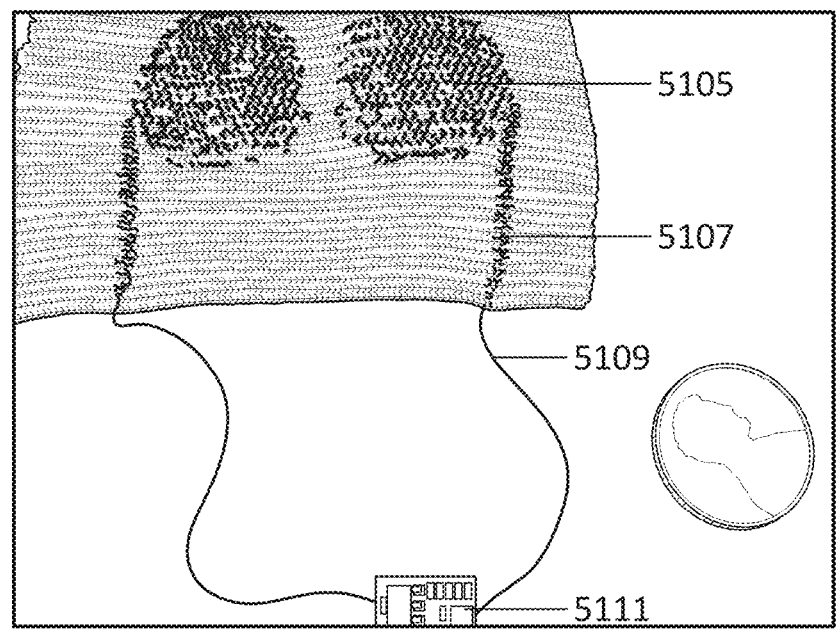
FIG. 51 is an example prototype of a neuromodulator formed of a woven material (in this example a stainless steel yarn) having electrodes formed one a woven substrate.
Figure 52A:
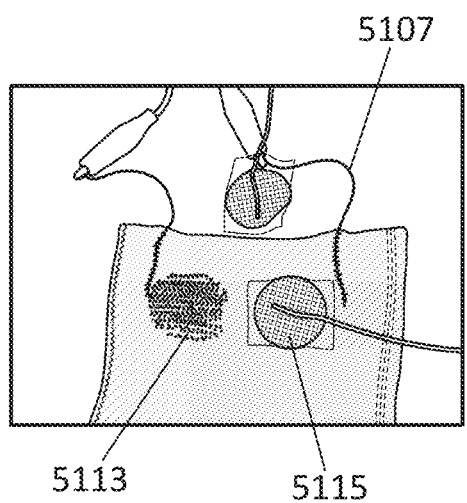
FIG. 52A is an example of a test of a woven electrode similar to the variation shown in FIG. 51.
Figure 52B:
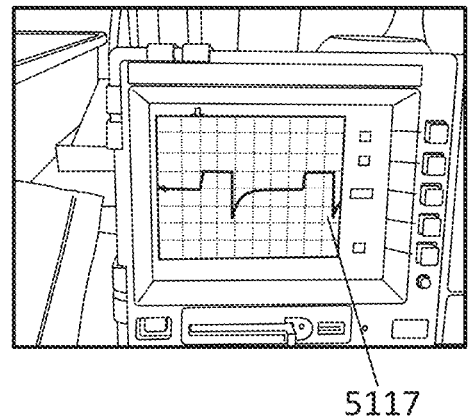
FIG. 52B illustrates transmission of a test waveform using the prototype neuromodulator shown in FIG. 52A.

FIG. 51 is an example prototype of a neuromodulator formed of a woven material (in this example a stainless steel yarn 5105) having electrodes formed one a woven substrate. A lead wire 5107 is woven into the substrate, and the lead wire exits 5109 to connect to the control circuitry 5111 (e.g., PCB). Similarly, FIG. 52A is an example of a test of a woven electrode similar to the variation shown in FIG. 51. The woven lead wire 5107 connects to a stimulation source, and to the woven electrode 5113. A test electrode 5115 is connected through the gel to the neural stimulation electrode. FIG. 52B illustrates transmission of a test waveform using the prototype neuromodulator shown in FIG. 52A, showing a waveform 5117 picked up through coupling to the gel (shown having a full strength neural modulation electric current comping from the 3D woven electrode).

Figure 53:
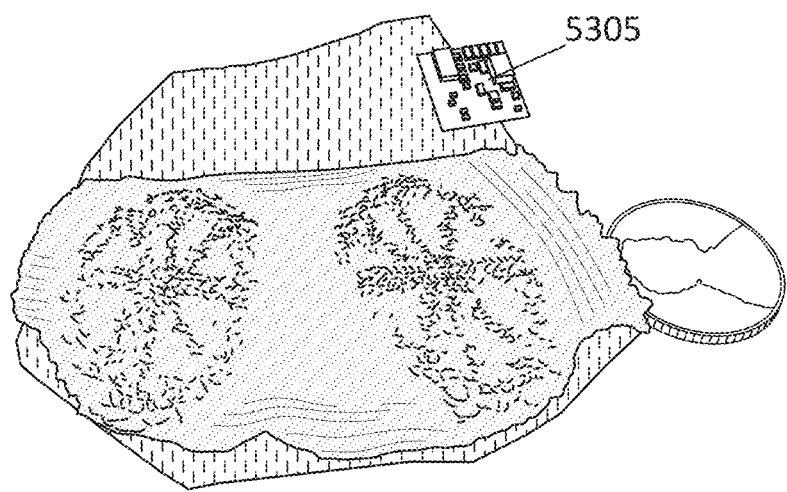
FIG. 53 is a prototype of an alternative design of a neuromodulator similar to that shown in FIG. 51, having electrodes formed one a woven substrate.

FIG. 53 is a prototype of an alternative design of a neuromodulator similar to that shown in FIG. 51, having electrodes formed one a woven substrate. In FIG. 53, the apparatus includes stainless steel wire and the electrode, woven into the nylon substrate. This design may be highly efficient, since the stainless wire is of very low resistance. The oxide layer on the stainless steel wire may provide a resistance in the Z-direction (direction out of the paper) to distribute the current evenly. A miniature control circuitry 5305 is pre-programed with a neural modulation waveform(s). The contiguous lead wire may extend out of plane and connect to the control circuitry through the back side.

Figure 54:
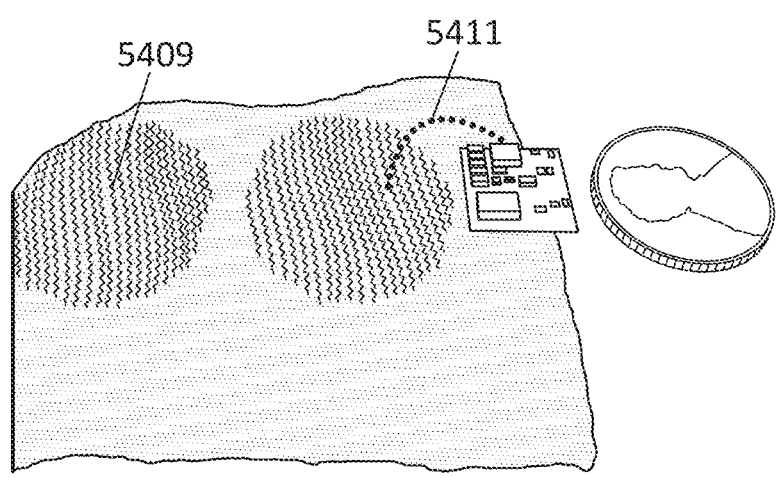
FIG. 54 is a prototype of an alternative design of a neuromodulator similar to that shown in FIG. 51, having electrodes formed one a woven substrate.

FIG. 54 is a prototype of an alternative design of a neuromodulator similar to that shown in FIG. 51, having electrodes formed one a woven substrate. The density of the weave may be adjusted to provide more conductivity where needed. In This example, a high density 5409 weave portion may provide a central conductor to distribute electrical current to lateral branches for X, Y plane distribution of electric current. A conductor is connect to the control circuitry 5411 out of the plane of the back side of the fabric.

Figure 55:
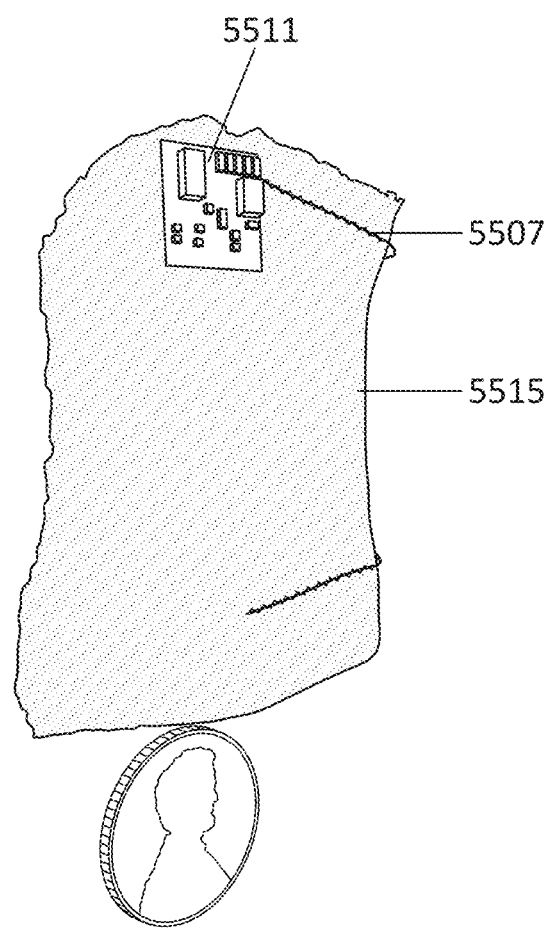
FIG. 55 is another example of a prototype of an alternative design of a neuromodulator having electrodes formed one a woven substrate, similar to that shown in FIG. 51.

FIG. 55 is another example of a prototype of an alternative design of a neuromodulator having electrodes formed one a woven substrate, similar to that shown in FIG. 51. The woven lead wire on the back side may be insulated by the fabric so that the user is not exposed to a voltage from the lead wire. The control circuitry 5511 may be placed on the back side of the apparatus without any additional routing of the lead wire to the back side. The woven lead wire 5507 may therefore be passed through the fabric 5515 serving as an insulator (electric insulator).

In general, the methods and apparatuses described herein may be used with or as part of one or more of: transdermal electric stimulation ("TES"), transcranial alternating current stimulation ("tACS"), transcranial direct current stimulation ("tDCS"), cranial electrotherapy stimulation ("CES"), transcranial random noise stimulation ("tRNS"), trigeminal nerve stimulation ("TNS"), and vagal nerve stimulation ("VNS"), amongst other forms known to those skilled in the art.

Memory Enhancement

Any of the apparatuses described herein may be used for enhancing memory.

Figure 56A:
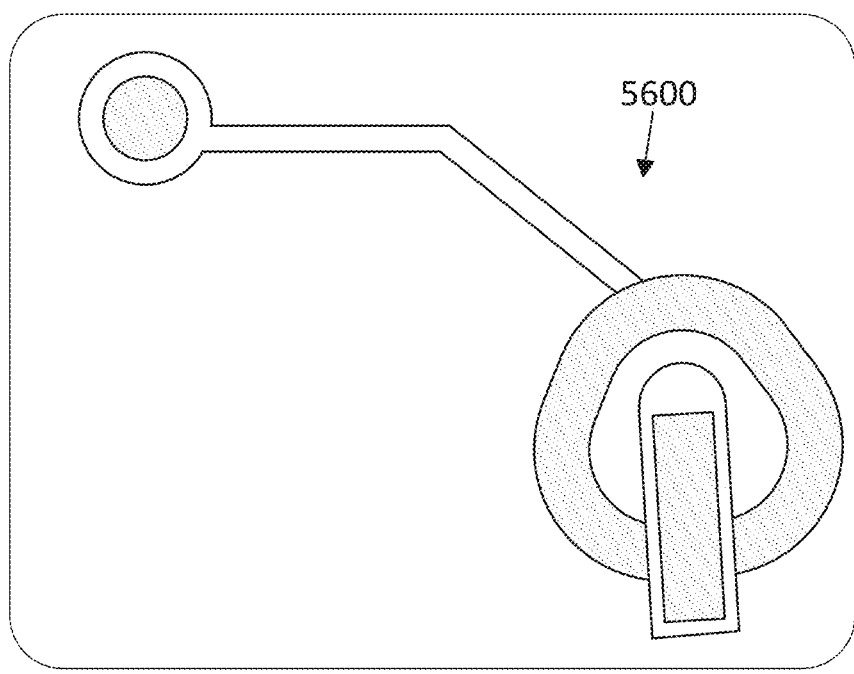
FIGS. 56A-56B is one example of a neuromodulator similar to those described above (e.g., in FIGS. 31A-31H and 32A-32H, configured to have a third electrode (e.g., cathode).
Figure 56B:
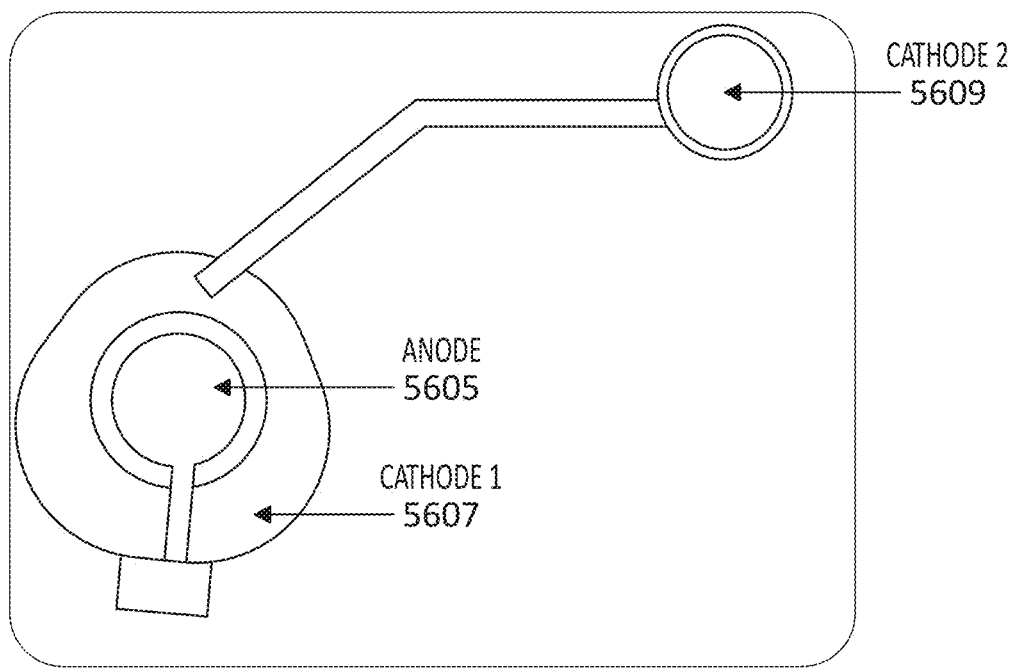

For example, FIGS. 56A-56B show one example of a neuromodulator similar to those described above (e.g., in FIGS. 31A-31H and 32A-32H) that are configured to have a third electrode (e.g., cathode) and may be used for improving a subject's cognitive state, and in particular, memory. For example, FIG. 56A shows a front view of a neuromodulator apparatus 5600 (showing the fabric cover wrapping around and covering the battery and control circuitry), while FIG. 56B shows the neuromodulator from the back view, showing the electrodes (including the hydrogel forming the electrodes).

The device may be worn by a subject and used to improve memory. The prototype apparatus shown in FIGS. 56A-56B includes three electrodes in a center-surround, source-sink pattern, configured as an anode 5605, first cathode 5607 and second cathode 5609. The device may be applied over E27/E29 (on the temples) and over E12 (midline of the forehead) as shown in FIG. 50. In this example, the electrode at E27 is the anode (this is the center circle in the annular design of the apparatus), while the electrode on E29 is the outer electrode (cathode) formed by the ring around the anode at E27. As shown in FIG. 57, this concentric electrode is placed at the temple, creating the electric field on the lower middle portion of the brain, as shown in FIG. 59. The third electrode, a cathode, is placed at the E12 position, shown in FIG. 27A-27C as the middle of the forehead. As shown in FIG. 59, the electrode at E12 creates the field at the frontal lobe (left side of the brain) 5909 from the second cathode, and synchronized fields at the temporal region 5911 from the first cathode. The waveform applied may include a theta-like wave (e.g., frequency of between 4-8 Hz) that may force these two brain region to be synchronized thereby enhancing the memory function of the brain. Two or more frequencies may be used for memory enhancements: the theta-like waves (low frequency), and a higher frequency component corresponding to Gamma waves.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wearable neuromodulator device, the device comprising:
    a flexible substrate;
    a first electrode and a second electrode on the flexible substrate;
    a first hydrogel layer in electrical communication with the first electrode and a second hydrogel layer in electrical communication with the second electrode;
    a third hydrogel layer in electrical communication with the first hydrogel layer;

a removable release layer, wherein the first hydrogel layer is separated from the third hydrogel layer by the release layer;
a battery;
a control circuitry; and
a circuit interrupt removably coupled with the control circuitry, wherein the circuit interrupt is interposed between the battery and the control circuitry so that removing the circuit interrupt powers the control circuitry,
further wherein the control circuitry is configured to deliver a first predefined waveform between the first and second electrodes after the circuit interrupt is removed, and a second predefined waveform between the first and second electrodes after the release layer is removed.

2. The device of claim 1, wherein the release layer is connected to or forms part of the circuit interrupt for activating or re-setting the control circuitry so that it enters into a standby mode and prepares to deliver the second predefined waveform when an electrical property detects the presence of skin contact.

3. The device of claim 1, wherein the release layer and the first hydrogel layer are removable to expose the third hydrogel layer.

4. The device of claim 3, wherein removing the first hydrogel layer removes the circuit interrupt and allows activation of the second predefined waveform that is different from the first predefined waveform.

5. The device of claim 4, wherein the second predefined waveform has an amplitude that is between about 10-30% lower amplitude compared to the first predefined waveform.

6. The device of claim 1, wherein one or more of the first, second and third hydrogel layers have a thickness of less than about 2 mm.

7. The device of claim 1, wherein the release layer is made of a non-conductive material and has openings through which the first and third hydrogel layers are in contact.

8. The device of claim 1, wherein the first and/or second predefined waveform has a frequency of between about 100 Hz and 15 KHz and a charge per phase of between 0.1-10 microCoulombs.

9. A wearable neuromodulator device, the device comprising:
a flexible substrate;
a first electrode and a second electrode on the flexible substrate;
a first hydrogel layer in electrical communication with the first electrode and a second hydrogel layer in electrical communication with the second electrode;
a third hydrogel layer in electrical communication with the first hydrogel layer;
a fourth hydrogel layer in electrical communication with the second hydrogel layer;
a removable release layer, wherein the first and second hydrogel layers are separated from the third and fourth hydrogel layers by the release layer;
a battery;
a control circuitry; and
a pull tab removably coupled with the control circuitry, wherein the pull tab is interposed between the battery and the control circuitry so that removing the pull tab powers the control circuitry,
further wherein the control circuitry is configured to deliver a first predefined waveform between the first and second electrodes after the pull tab is removed, and a second predefined waveform between the first and second electrodes after the release layer is removed, wherein the second predefined waveform has an intensity that is 5-50% lower than the first predefined waveform.

10. The device of claim 9, wherein the release layer is made of a non-conductive material and has openings through which the first and third hydrogel layers and the second and fourth hydrogel layers are in contact.

11. The device of claim 9, wherein the release layer is connected to or forms part of the pull tab for activating or re-setting the control circuitry so that it enters into a standby mode and prepares to deliver the second predefined waveform when an electrical property detects the presence of skin contact.

12. The device of claim 1, wherein the release layer and the first and second hydrogel layers are removable to expose the third and fourth hydrogel layers.

13. The device of claim 12, wherein removing the first and second hydrogel layers removes the pull tab and allows activation of the second predefined waveform.

14. The device of claim 9, wherein one or more of the first, second, third and fourth hydrogel layers have a thickness of less than about 2 mm.

15. The device of claim 9, wherein the release layer is made of a non-conductive material and has openings through which the first and third hydrogel layers are in contact and the second and fourth hydrogel layers are in contact.

16. The device of claim 9, wherein one or both of the first and second predefined waveforms has a frequency of between about 100 Hz and 15 KHz and a charge per phase of between 0.1-10 microCoulombs.

* * * * *